(12) United States Patent
Fischer et al.

(10) Patent No.: US 6,500,817 B1
(45) Date of Patent: Dec. 31, 2002

(54) THIAZOLYL UREA DERIVATIVES AND THEIR UTILIZATION AS ANTIVIRAL AGENTS

(75) Inventors: Rüdiger Fischer, Pulheim (DE); Gerald Kleymann, Wuppertal (DE); Judith Baumeister, Wuppertal (DE); Wolfgang Bender, Wuppertal (DE); Ulrich Betz, Wuppertal (DE); Peter Eckenberg, Wuppertal (DE); Gabriele Handke, Wülfrath (DE); Martin Hendrix, Köln (DE); Udo Schneider, Leverkusen (DE); Olaf Weber, Woodbridge, CT (US); Kerstin Henninger, Wuppertal (DE); Axel Jensen, Velbert (DE); Jörg Keldenich, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/914,554

(22) PCT Filed: Feb. 24, 2000

(86) PCT No.: PCT/EP00/01498

§ 371 (c)(1),
(2), (4) Date: Aug. 31, 2001

(87) PCT Pub. No.: WO00/53591

PCT Pub. Date: Sep. 14, 2000

(30) Foreign Application Priority Data

Mar. 8, 1999 (DE) .......................... 199 10 245
Dec. 13, 1999 (DE) .......................... 199 59 958

(51) Int. Cl.[7] .................... A61K 31/426; A61K 31/427; C07D 277/54; C07D 417/12; C07D 487/04

(52) U.S. Cl. ................. 514/210.2; 514/217.1; 514/227.8; 514/229.2; 514/236.8; 514/254.04; 514/326; 514/342; 514/364; 514/369; 540/603; 544/60; 544/65; 544/124; 544/133; 544/367; 546/209; 546/270.7; 548/131; 548/181; 548/185

(58) Field of Search ................. 548/181, 185, 548/131; 544/133, 60, 65, 124, 367; 546/209, 270.7; 540/603; 514/210.2, 217.1, 227.8, 229.2, 236.8, 254.04, 326, 342, 364, 369

(56) References Cited

U.S. PATENT DOCUMENTS 3,658,830 A * 4/1972 Pilgram et al. .......... 260/306.8
3,717,651 A    2/1973 Pilgram et al. .......... 260/306.8
3,847,588 A   11/1974 Pilgram et al. ................ 71/90

FOREIGN PATENT DOCUMENTS

| DE | 2101640 | 7/1971 |
| WO | 9724343 | 7/1997 |
| WO | 9937291 | 7/1999 |
| WO | 9942455 | 8/1999 |
| WO | 9947507 | 9/1999 |

OTHER PUBLICATIONS

Ziegler, C., Kuhl, E., Sprague, J., "2–Aminothiazolesulfonamides", J. Organ. Chem., 25:1454–1455 (1960).

* cited by examiner

Primary Examiner—Laura L. Stockton
(74) Attorney, Agent, or Firm—Jerrie L. Chiu

(57) ABSTRACT

The present invention relates to thiazolylurea derivatives, a process for their preparation, and their use as pharmaceuticals, in particular as antiviral pharmaceuticals.

18 Claims, No Drawings

THIAZOLYL UREA DERIVATIVES AND THEIR UTILIZATION AS ANTIVIRAL AGENTS

This application is a 371 of PCT/EP00/01498 filed Feb. 24, 2000.

The present invention relates to thiazolylurea derivatives, a process for their preparation, and their use as pharmaceuticals, in particular as antiviral pharmaceuticals.

The publication by C. Ziegler et al., J. Org. Chem. 25, 1960, 1454–1455 discloses 2-aminothiazole-5-sulphonamides. In addition, Gennan Offenlegungsschrift 2101640 describes N-thiazol-2-ylamides and -ureas with a herbicidal action.

WO 97/24343 relates to phenylthiazole derivatives with anti-herpes virus properties.

WO 99/42455 likewise relates to phenylthiazole derivatives with anti-herpes virus properties.

WO 99/47507 relates to 1,3,4-thiadiazole derivatives with anti-herpes virus properties.

The present invention relates to thiazolylurea derivatives of the general formula (I)

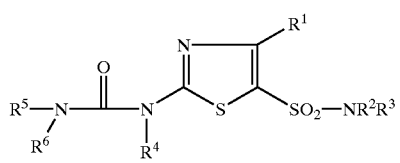

in which
$R^1$ represents hydrogen, halogen, $(C_1-C_6)$-alkyl, $(C_1-C_6)$-alkoxy, amino$(C_1-C_6)$alkyl or halogeno$(C_1-C_6)$alkyl,
$R^2$ and $R^3$ are identical or different and represent hydroten, $(C_3-C_8)$-cycloalkyl or biphenylylaminocarbonyl, or
represent $(C_1-C_6)$-alkyl which is optionally substituted by 1 to 3 substituents selected from the group consisting of $(C_3-C_6)$-cycloalkyl, $(C_1-C_6)$-alkoxy, halogen, hydroxyl, radicals of the formula

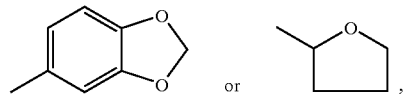

a 5- to 6-membered aromatic heterocycle with up to 3 heteroatoms from the series S, N and/or O, it also being possible for a nitrogen-containing heterocycle to be bonded via the nitrogen atom,
a 3- to 8-membered saturated or unsaturated, nonaromatic heterocycle which has up to 3 heteroatoms from the series S, N and/or O and is optionally bonded via a nitrogen atom, and $(C_6-C_{10})$-aryl which in turn may be substituted by hydroxyl or $(C_1-C_6)$-alkoxy, or
$R^2$ and $R^3$ form, together with the nitrogen atom, a 5- to 6-membered saturated heterocycle which may optionally also have an oxygen atom,
$R^4$ represents hydrogen, $(C_1-C_6)$-acyl, $(C_2-C_6)$-alkenyl, or
$R^4$ represents $(C_1-C_6)$-alkyl which can optionally be substituted by 1 to 3 substituents selected from the group consisting of halogen, hydroxyl, $(C_1-C_6)$-acyl, $(C_1-C_6)$-alkoxy, phenoxy $(C_6-C_{10})$-aryl and $-NR^7R^8$, in which $R^7$ and $R^8$ are identical or different and denote hydrogen, $(C_1-C_6)$-acyl, $(C_1-C_6)$-alkyl, carbamoyl, mono- or di$(C_1-C_6)$-alkylamino$(C_1-C_6)$alkyl, mono- or di$(C_1-C_6)$-alkyl-aminocarbonyl, $(C_6-C_{10})$-aryl or $(C_1-C_6)$-alkoxycarbonyl, or $R^7$ and $R^8$ form, together with the nitrogen atom, a 5- to 6-membered saturated heterocycle which may optionally contain another heteroatom from the series S or O or a radical of the formula $-NR^9$ and may be substituted by oxo, in which $R^9$ denotes hydrogen or $(C_1-C_4)$-alkyl, or $R^4$ represents $(C_1-C_6)$-alkyl which is substituted by a 5- to 6-membered aromatic, optionally benzo-fused heterocycle with up to 3 heteroatoms in the series S, N and/or O, it also being possible for a nitrogen-containing heterocycle to be bonded via the nitrogen atom, or is substituted by radicals of the formulae

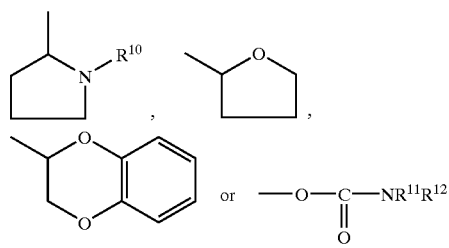

in which
$R^{10}$ denotes hydrogen or $(C_1-C_6)$-alkyl,
$R^{11}$ and $R^{12}$ are identical or different and denote hydrogen, $(C_1-C_6)$-alkyl or $(C_6-C_{10})$-aryl, it being possible for the aforementioned $(C_1-C_6)$-alkyl and $(C_6-C_{10})$-aryl optionally to be substituted by 1 to 3 substituents selected from the group consisting of hydroxyl, $(C_1-C_6)$-alkoxy and halogen,
$R^5$ represents hydrogen or $(C_1-C_6)$-alkyl,
$R^6$ represents a radical of the formula

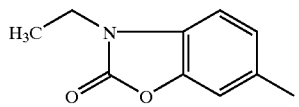

or $R^6$ represents phenyl which can optionally be substituted by one to three substituents selected from the group consisting of
halogen, $(C_6-C_{10})$-aryl which can optionally be substituted by 1 to 3 substituents selected from $(C_1-C_6)$ alkanoyl, $(C_1-C_6)$-alkoxy, $(C_1-C_6)$-alkyl, halogen, $(C_1-C_6)$alkoxycarbonyl, nitro, halogeno$(C_1-C_6)$ alkyl, halogeno$(C_1-C_6)$alkoxy, amino, $(C_1-C_6)$ alkylthio, hydroxyl, carboxyl, carbamoyl, mono- or di$(C_1-C_6)$alkylaminocarbonyl, mono- or di$(C_1-C_6)$ acylamino, $(C_1-C_6)$alkylsulphinyl, $(C_1-C_6)$ alkylsulphonyl, and/or cyano, or $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy with up to 6 fluorine atoms, radicals of the formulae

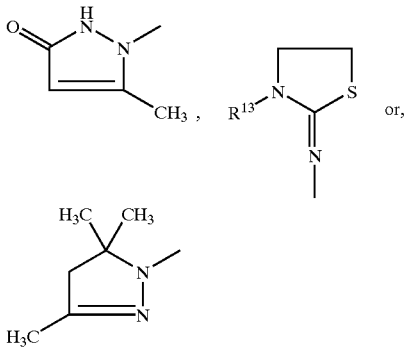

in which R¹³ denotes hydrogen or $(C_1-C_6)$-alkyl, $(C_1-C_6)$-alkyl which is optionally substituted by a radical of the formula

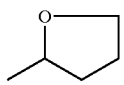

a 5- to 6-membered aromatic heterocycle which has up to 3 heteroatoms from the series S, N and/or O, is optionally bonded via a nitrogen atom and can optionally be substituted by 1 to 3 substituents selected from $(C_1-C_6)$alkanoyl, $(C_1-C_6)$-alkoxy, $(C_1-C_6)$-alkyl, halogen, $(C_1-C_6)$alkoxycarbonyl, nitro, halogeno$(C_1-C_6)$alkyl, halogeno$(C_1-C_6)$alkoxy, amino, $(C_1-C_6)$alkylthio, hydroxyl, carboxyl, carbamoyl, mono- or di$(C_1-C_6)$alkylaminocarbonyl, mono- or di$(C_1-C_6)$acylamino, $(C_1-C_6)$alkylsulphinyl, $(C_1-C_6)$alkylsulphonyl, and/or cyano, a 3- to 8-membered saturated or unsaturated, nonaromatic mono- or bicyclic heterocycle which has up to 3 heteroatoms from the series S, N and/or O, is optionally bonded via a nitrogen atom and may optionally be substituted by 1 to 3 substituents selected from oxo, halogen, hydroxyl, $(C_1-C_6)$-alkoxycarbonyl, $(C_1-C_6)$alkoxy-carbonylamino, $(C_1-C_6)$-alkyl, halogeno$(C_1-C_6)$-alkyl and hydroxy $(C_1-C_6)$-alkyl, and groups of the formulae —OR¹⁴, —NR¹⁵R¹⁶ or —CO—NR¹⁷R¹⁸, in which R¹⁴ denotes a radical of the formula

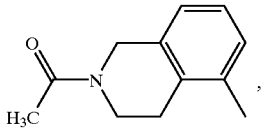

or denotes phenyl which in turn is optionally substituted by a group of the formula —NR¹⁹R²⁰, in which R¹⁹ and R²⁰ are identical or different and denote hydrogen, $(C_1-C_6)$-alkyl or $(C_1-C_6)$-acyl, or R¹⁴ denotes $(C_1-C_6)$-alkyl which is optionally substituted once to three times by hydroxyl, R¹⁵ and R¹⁶ are identical or different and denote hydrogen, carbamoyl, mono- or di$(C_1-C_6)$ alkylaminocarbonyl, phenyl, $(C_1-C_6)$-acyl or $(C_1-C_6)$-alkyl, where $(C_1-C_6)$-alkyl is optionally substituted by $(C_1-C_6)$-alkoxy, $(C_1-C_6)$-acyl, by phenyl or by a 5- to 6-membered aromatic heterocycle with up to 3 heteroatoms from the series S, N and/or O, where aforementioned phenyl and aforementioned aromatic heterocycle are optionally substituted once to three times, identically or differently, by halogen and/or hydroxyl, and R¹⁷ and R¹⁸ are identical or different and denote hydrogen or $(C_1-C_6)$-alkyl, and the salts thereof.

Physiologically acceptable salts of the compounds according to the invention may be salts of the substances according to the invention with mineral acids, carboxylic acids or sulphonic acids. Particularly preferred examples are salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts which may be mentioned are salts with conventional bases, such as, for example, alkali metal salts (for example sodium or potassium salts), alkaline earth metal salts (for example calcium or magnesium salts) or ammonium salts derived from ammonia or organic amines such as, for example, diethylamine, triethylamine, ethyldiisopropylamine, procaine, dibenzylamine, N-methylmorpholine, dihydroabietylamine, 1-ephenamine or methylpiperidine.

The invention also includes within its scope those compounds which are converted only in the body into the actual active substances of the formula (I) (called prodrugs).

The compounds according to the invention may, depending on the substitution pattern, exist in stereoisomeric forms which are either related as image and mirror image (enantiomers) or which are not related as image and mirror image (diastereomers). The invention relates both to the enantiomers or diastereomers or mixtures thereof in each case. The racemic forms can, just like the diastereomers, be separated into the stereoisomerically homogeneous components in a known manner.

$(C_1-C_6)$-Alkyl represents a straight-chain or branched alkyl radical with 1 to 6 carbon atoms. A straight-chain or branched alkyl radical with 1 to 4 carbon atoms $(C_1-C_4)$ is preferred. Examples which may be mentioned are: methyl, ethyl, n-propyl, isopropyl, n-butyl, sec-butyl, tert-butyl, n-pentyl and n-hexyl. A straight-chain or branched alkyl radical with 1 to 3 carbon atoms $(C_1-C_3)$alkyl) is particularly preferred.

Halogeno$(C_1-C_6)$-alkyl represents a $(C_1-C_6)$alkyl group which may be defined as above and which has 1 to 3 halogen atoms, namely F, Cl, Br and/or I, preferably chlorine or fluorine, as substituents; examples which may be mentioned are trifluoromethyl, fluoromethyl, etc.

Hydroxy$(C_1-C_6)$-alkyl represents a $(C_1-C_6)$alkyl group which may be defined as above and which has 1 to 3 hydroxyl groups as substituents; examples which may be mentioned are hydroxymethyl etc.

$(C_2-C_6)$-Alkenyl represents for the purposes of the invention a straight-chain or branched alkenyl radical with 2 to 6 carbon atoms. Examples which may be mentioned are: ethenyl, n-prop-2-en-1-yl and n-but-2-en-1-yl. A straight-chain or branched alkenyl radical with 2 to 4 carbon atoms is preferred.

$(C_1-C_6)$-Alkoxy represents a straight-chain or branched alkoxy radical with 1 to 6 carbon atoms. A straight-chain or branched alkoxy radical with 1 to 4 carbon atoms ($C_1$–$C_4$) is preferred. Examples which may be mentioned are: methoxy, ethoxy, n-propoxy, isopropoxy, tert-butoxy and n-pentoxy and n-hexoxy. A straight-chain or branched alkoxy radical with 1 to 3 carbon atoms ($C_1$–$C_3$) is particularly preferred.

Partially fluorinated ($C_1$–$C_6$)-alkoxy with up to 6 fluorine atoms represents a straight-chain or branched alkoxy radical which has 1 to 6 carbon atoms and which may be substituted by 1 to 6, preferably 1 to 4, more preferably 1 to 3, fluorine atoms. A straight-chain or branched alkoxy radical with 1 to 4 carbon atoms and 1 to 4 fluorine atoms is preferred. Examples which may be mentioned are: methoxy, ethoxy, n-propoxy, isopropoxy, tert-butoxy, n-pentoxy and n-hexoxy, each of which has 1 to 4 fluorine atoms. (1,3-Difluoroprop-2-yl)oxy and 1,1,2,2-tetrafluoroethoxy are particularly preferred.

($C_1$–$C_6$)-Alkylthio represents a straight-chain or branched alkylthio radical with 1 to 6 carbon atoms. A straight-chain or branched alkylthio radical with 1 to 4 carbon atoms ($C_1$–$C_4$) is preferred. Examples which may be mentioned are: methylthio, ethylthio, n-propylthio, isopropylthio, tert-butylthio, n-pentylthio and n-hexylthio. A straight-chain or branched alkylthio radical with 1 to 3 carbon atoms ($C_1$–$C_3$) alkylthio is particularly preferred.

($C_1$–$C_6$)-Alkoxycarbonyl represents a straight-chain or branched alkoxycarbonyl radical with 1 to 6 carbon atoms. A straight-chain or branched alkoxycarbonyl radical with 1 to 4 carbon atoms ($C_1$–$C_4$) is preferred. Examples which may be mentioned are: methoxycarbonyl, ethoxycarbonyl, n-propoxycarbonyl, isopropoxycarbonyl and tert-butoxycarbonyl. A straight-chain or branched alkoxycarbonyl radical with 1 to 3 carbon atoms ($C_1$–$C_3$) is particularly preferred.

Mono- or di($C_1$–$C_6$)alkylaminocarbonyl represents for the purposes of the invention expediently a carbamoyl group ($H_2N$—CO—) in which one or both hydrogen atoms are replaced by a ($C_1$–$C_6$)alkyl group. Concerning the definition of the ($C_1$–$C_6$)alkyl group, reference may be made to the above explanation of ($C_1$–$C_6$)alkyl. Examples which may be mentioned are methylaminocarbonyl, dimethylaminocarbonyl etc.

Mono- or di-($C_1$–$C_6$)acylamino represents for the purposes of the invention expediently an amino group ($H_2N$—) in which one or both hydrogen atoms are replaced by a ($C_1$–$C_6$)acyl group. Concerning the definition of the ($C_1$–$C_6$) acyl group, reference may be made to the explanation of ($C_1$–$C_6$)acyl below. Examples which may be mentioned are ($C_1$–$C_6$)alkanoyl as mentioned in the definition of ($C_1$–$C_6$) acyl.

($C_1$–$C_6$)Alkylsulphinyl expediently represents a ($C_1$–$C_6$) alkyl-S(=O) group and, concerning the ($C_1$–$C_6$)alkyl group, reference may be made to the definition concerning this above.

($C_1$–$C_6$)Alkylsulphonyl expediently represents a ($C_1$–$C_6$) alkyl-$SO_2$ group and, concerning the ($C_1$–$C_6$)alkyl group, reference may be made to the definition concerning this above.

($C_6$–$C_{10}$)-Aryl generally represents an aromatic radical with 6 to 10 carbon atoms. Preferred aryl radicals are phenyl and naphthyl.

($C_1$–$C_6$)-Acyl represents for the purposes of the invention expediently a straight-chain or branched acyl radical with 1 to 6 carbon atoms. Examples which may be mentioned are: formyl, acetyl, ethylcarbonyl, propylcarbonyl, isopropylcarbonyl, butylcarbonyl, isobutylcarbonyl, pentylcarbonyl and hexylcarbonyl. A straight-chain or branched acyl radical with 1 to 4 carbon atoms is preferred. Acetyl and ethylcarbonyl are particularly preferred.

($C_3$–$C_8$)-Cycloalkyl represents for the purposes of the invention expediently cyclopropyl, cyclopentyl, cyclobutyl, cyclohexyl, cycloheptyl or cyclooctyl. Those which may preferably be mentioned are: cyclopropyl, cyclopentyl and cyclohexyl. The meaning of ($C_3$–$C_6$)cycloalkyl accordingly expediently represents cyclopropyl, cyclopentyl, cyclobutyl, cyclohexyl.

Halogen generally represents for the purposes of the invention fluorine, chlorine, bromine and iodine. Fluorine, chlorine and bromine are preferred. Fluorine and chlorine are particularly preferred.

A 5- to 6-membered aromatic heterocycle with up to 3 heteroatoms from the series S, O and/or N represents, for example, pyridyl, pyrimidyl, thienyl, furyl, pyrrolyl, thiazolyl, N-triazolyl, oxazolyl or imidazolyl. Pyridyl, furyl, thiazolyl and N-triazolyl are preferred.

A 5- to 6-membered aromatic benzo-fused heterocycle with up to 3 heteroatoms from the series S, O and/or N represents, for example, benzimidazolyl.

A 5- to 6-membered saturated heterocycle which is bonded via a nitrogen atom, which can be formed from two substituent groups together with the nitrogen atom to which they are bonded, and which may optionally contain another heteroatom from the series S or O or a radical of the formula —$NR^9$ in which $R^9$ is as defined above, generally represents for the purposes of the invention morpholinyl, piperidinyl, piperazinyl, methylpiperazinyl, thiomorpholinyl or pyrrolidinyl. Morpholinyl, piperidinyl, pyrrolidinyl and thiomorpholinyl are particularly preferred.

A 3- to 8-membered saturated or unsaturated, nonaromatic heterocycle which is optionally bonded via a nitrogen atom and which has up to 3 heteroatoms from the series S, N and/or O includes, for example, the abovementioned 5- to 6-membered saturated heterocycles which are bonded via a nitrogen atom, as well as 3-, 7- and 8-membered heterocycles such as, for example, aziridines (for example 1-azacyclopropan-1-yl), azetidines (for example 1-azacyclobutan-1-yl) and azepines (for example 1-azepan-1-yl). The unsaturated representatives may contain 1 to 2 double bonds in the ring.

In a preferred embodiment, the invention relates to compounds of the general formula (I) in which $R^6$ represents phenyl which may optionally be substituted by one to three substituents selected from the group consisting of halogen, ($C_6$–$C_{10}$)-aryl which can optionally be substituted by 1 to 3 substituents selected from ($C_1$–$C_6$)alkanoyl, ($C_1$–$C_6$)-alkoxy, ($C_1$–$C_6$)-alkyl, halogen, ($C_1$–$C_6$)alkoxycarbonyl, nitro, halogeno ($C_1$–$C_6$)alkyl, halogeno($C_1$–$C_6$)alkoxy, amino, ($C_1$–$C_6$)alkylthio, hydroxyl, carboxyl, carbamoyl, mono- or di($C_1$–$C_6$)alkylaminocarbonyl, mono- or di($C_1$–$C_6$)acylamino, ($C_1$–$C_6$)alkylsulphinyl, ($C_1$–$C_6$) alkylsulphonyl, and/or cyano, or of ($C_1$–$C_6$)-alkoxy, ($C_1$–$C_6$)-alkoxycarbonyl, ($C_1$–$C_6$)-alkylthio, hydroxyl, carboxyl, partially fluorinated ($C_1$–$C_6$)-alkoxy with up to 6 fluorine atoms, ($C_1$–$C_6$)-alkyl, a 5- to 6-membered aromatic heterocycle which has up to 3 heteroatoms from the series S, N and/or O, is optionally bonded via a nitrogen atom and may optionally be substituted by 1 to 3 substituents selected from ($C_1$–$C_6$)alkanoyl, ($C_1$–$C_6$)-alkoxy, ($C_1$–$C_6$)-alkyl, halogen, ($C_1$–$C_6$) alkoxycarbonyl, nitro, halogeno($C_1$–$C_6$)alkyl, halogeno($C_1$–$C_6$)alkoxy, amino, ($C_1$–$C_6$)alkylthio, hydroxyl, carboxyl, carbamoyl, mono- or di($C_1$–$C_6$) alkylaminocarbonyl, mono- or di($C_1$–$C_6$)acylamino, ($C_1$–$C_6$)alkylsulphinyl, ($C_1$–$C_6$)alkylsulphonyl, and/or cyano, or of a 3to 8-membered saturated or unsaturated, nonaromatic, mono- or bicyclic heterocycle which has up to 3 heteroatoms from the series S, N and/or O, is optionally bonded via a nitrogen atom and can optionally be substituted by 1 to 3 substituents selected from oxo, halogen, hydroxyl, $(C_1-C_6)$-alkoxycarbonyl, $(C_1-C_6)$alkoxy-carbonylamino, $(C_1-C_6)$-alkyl, halogeno$(C_1-C_6)$-alkyl and hydroxy$(C_1-C_6)$-alkyl, and groups of the formulae $-OR^{14}$, $-NR^{15}R^{16}$ or $-CO-NR^{17}R^{18}$, in which $R^{14}$ is phenyl, which in turn is optionally substituted by a group of the formula $-NR^{19}R^{20}$,
in which
$R^{19}$ and $R^{20}$ are identical or different and denote hydrogen, $(C_1-C_6)$-alkyl or $(C_1-C_6)$-acyl,
or
$R^{14}$ denotes $(C_1-C_6)$-alkyl which is optionally substituted once to three times by hydroxyl,
$R^{15}$ and $R^{16}$ are identical or different and denote hydrogen, carbamoyl, mono- or di$(C_1-C_6)$ alkylaminocarbonyl, phenyl, $(C_1-C_6)$-acyl or $(C_1-C_6)$-alkyl,
where $(C_1-C_6)$-alkyl is optionally substituted by $(C_1-C_6)$-alkoxy, $(C_1-C_6)$-acyl, by phenyl or by a 5- to 6-membered aromatic heterocycle with up to 3 heteroatoms from the series S, N and/or O,
where aforementioned phenyl and aforementioned aromatic heterocycle are optionally substituted once to three times, identically or differently, by halogen and/or hydroxyl, and
$R^{17}$ and $R^{18}$ are identical or different and denote hydrogen or $(C_1-C_6)$-alkyl,
and the salts thereof.

In another preferred embodiment, the invention relates to compounds of the general formula (I) in which
$R^6$ represents phenyl which may optionally be substituted by one to three substituents selected from the group consisting of halogen, $(C_6-C_{10})$-aryl which may optionally be substituted by 1 to 3 substituents selected from $(C_1-C_6)$alkanoyl, $(C_1-C_6)$-alkoxy, $(C_1-C_6)$-alkyl, halogen, $(C_1-C_6)$alkoxycarbonyl, nitro, halogeno$(C_1-C_6)$alkyl, halogeno$(C_1-C_6)$alkoxy, amino, $(C_1-C_6)$alkylthio, hydroxyl, carboxyl, carbamoyl, mono- or di$(C_1-C_6)$alkylaminocarbonyl, mono- or di$(C_1-C_6)$acylamino, $(C_1-C_6)$alkylsulphinyl, $(C_1-C_6)$ alkylsulphonyl, and/or cyano, or $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy with up to 6 fluorine atoms and $(C_1-C_6)$-alkyl,
and the salts thereof.

In another embodiment, the invention relates to compounds of the formula (I), in which
$R^1$ represents hydrogen, halogen or represents $(C_1-C_6)$-alkyl,
$R^2$ and $R^3$ are identical or different and represent hydrogen or $(C_3-C_8)$-cycloalkyl, or
represent $(C_1-C_6)$-alkyl which is optionally substituted by 1 to 3 substituents selected from the group consisting of $(C_3-C_6)$-cycloalkyl, $(C_1-C_6)$-alkoxy, halogen, hydroxyl, radicals of the formula

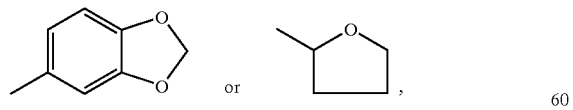

a 5- to 6-membered aromatic heterocycle with up to 3 heteroatoms from the series S, N and/or O, it also being possible for a nitrogen-containing heterocycle to be bonded via the nitrogen atom, and
$(C_6-C_{10})$-aryl which in turn can be substituted by hydroxyl or $(C_1-C_6)$-alkoxy, or $R^2$ and $R^3$ form, together with the nitrogen atom, a 5- to 6-membered saturated heterocycle which may optionally also have an oxygen atom,
$R^4$ represents hydrogen, $(C_1-C_6)$-acyl, $(C_2-C_6)$-alkenyl or
$R^4$ represents $(C_1-C_6)$-alkyl which can optionally be substituted by 1 to 3 substituents selected from the group consisting of halogen, hydroxyl, $(C_1-C_6)$-acyl, $(C_1-C_6)$-alkoxy, phenoxy, $(C_6-C_{10})$-aryl and $-NR^7R^8$,
in which $R^7$ and $R^8$ are identical or different and denote hydrogen, $(C_1-C_6)$-acyl, $(C_1-C_6)$-alkyl, carbamoyl, mono- or di$(C_1-C_6)$-alkylaminocarbonyl or $(C_1-C_6)$-alkoxycarbonyl, or $R^7$ and $R^8$ form, together with the nitrogen atom, a 5- to 6-membered saturated heterocycle which may optionally contain another heteroatom from the series S or O or a radical of the formula $-NR^9$,
in which $R^9$ denotes hydrogen or $(C_1-C_4)$-alkyl, or
$R^4$ represents $(C_1-C_6)$-alkyl which is substituted by a 5- to 6-membered aromatic, optionally benzo-fused heterocycle with up to 3 heteroatoms from the series S, N and/or O, it being possible for a nitrogen-containing heterocycle also to be bonded via the nitrogen atom, or is substituted by radicals of the formulae

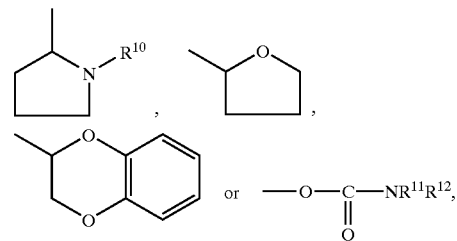

in which
$R^{10}$ denotes hydrogen or $(C_1-C_6)$-alkyl,
$R^{11}$ and $R^{12}$ are identical or different and denote hydrogen, $(C_1-C_6)$-alkyl or $(C_6-C_{10})$-aryl, where aforementioned $(C_1-C_6)$-alkyl and
$(C_6-C_{10})$-aryl can optionally be substituted by 1 to 3 substituents selected from the group consisting of hydroxyl, $(C_1-C_6)$-alkoxy and halogen,
$R^5$ represents hydrogen or $(C_1-C_6)$-alkyl,
$R^6$ represents a radical of the formula

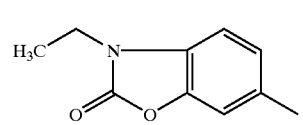

or
$R^6$ represents phenyl which can optionally be substituted by one to two substituents selected from the group consisting of
halogen, $(C_6-C_{10})$-aryl, $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy with up to 6 fluorine atoms, radicals of the formulae

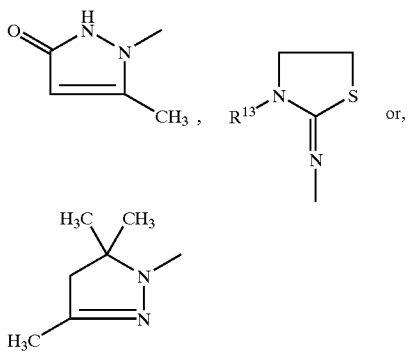

in which $R^{13}$ denotes hydrogen or $(C_1-C_6)$-alkyl,
$(C_1-C_6)$-alkyl, which is optionally substituted by a radical of the formula

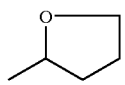

a 5- to 6-membered aromatic heterocycle which has up to 3 heteroatoms from the series S, N and/or O, is optionally bonded via a nitrogen atom and can optionally be substituted by one to three halogen atoms, a 3- to 8-membered, saturated or unsaturated, nonaromatic heterocycle which has up to 3 heteroatoms from the series S, N and/or O, is optionally bonded via a nitrogen atom and can optionally be substituted by 1 to 3 substituents selected from oxo, halogen, hydroxyl, $(C_1-C_6)$-alkoxycarbonyl, $(C_1-C_6)$-alkyl, halogeno$(C_1-C_6)$-alkyl and hydroxy$(C_1-C_6)$-alkyl,
and groups of the formulae —$OR^{14}$, —$NR^{15}R^{16}$ or —CO—$NR^{17}R^{18}$,
in which
$R^{14}$ denotes a radical of the formula

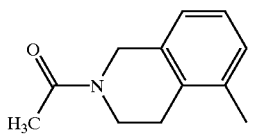

or phenyl which in turn is optionally substituted by a group of the formula —$NR^{19}R^{20}$,
in which
$R^{19}$ and $R^{20}$ are identical or different and denote hydrogen, $(C_1-C_6)$-alkyl or $(C_1-C_6)$-acyl,
or
$R^{14}$ denotes $(C_1-C_6)$-alkyl which is optionally substituted once to three times by hydroxyl,
$R^{15}$ and $R^{16}$ are identical or different and denote hydrogen, carbamoyl, mono- or di($C_1-C_6$) alkylaminocarbonyl, phenyl, $(C_1-C_6)$-acyl or $(C_1-C_6)$-alkyl,
where $(C_1-C_6)$-alkyl is optionally substituted by $(C_1-C_6)$-alkoxy, $(C_1-C_6)$-acyl, by phenyl or by a 5- to 6-membered aromatic heterocycle with up to 3 heteroatoms from the series S, N and/or O,
where aforementioned phenyl and aforementioned aromatic heterocycle are optionally substituted once to three times, identically or differently, by halogen and/or hydroxyl, and
$R^{17}$ and $R^{18}$ are identical or different and denote hydrogen or $(C_1-C_6)$-alkyl,
and the salts thereof.

Preference is given to compounds of the general formula (I), in which
$R^1$ represents hydrogen, chlorine or represents $(C_1-C_3)$-alkyl,
$R^2$ and $R^3$ are identical or different and represent hydrogen or cyclopropyl or cyclopentyl, or
represent $(C_1-C_3)$-alkyl which is optionally substituted by 1 to 3 substituents selected from the group consisting of cyclopropyl, cyclopentyl, $(C_1-C_3)$-alkoxy, chlorine, fluorine, hydroxyl, radicals of the formula

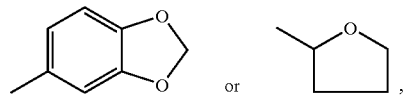

and pyridyl, furyl, thienyl, imidazolyl, N-triazolyl or pyrrolyl, phenyl which in turn may be substituted by hydroxyl or $(C_1-C_3)$-alkoxy, or
$R^2$ and $R^3$ form, together with the nitrogen atom, a morpholine, piperidine or pyrrolidine ring,
$R^4$ represents hydrogen, $(C_1-C_3)$-acyl, $(C_2-C_3)$-alkenyl, or
$R^4$ represents $(C_1-C_6)$-alkyl which can optionally be substituted by 1 to 3 substituents selected from the group consisting of chlorine, fluorine, hydroxyl, $(C_1-C_3)$-acyl, $(C_1-C_3)$-alkoxy, phenoxy, phenyl and —$NR^7R^8$,
in which $R^7$ and $R^8$ are identical or different and denote hydrogen, $(C_1-C_4)$-acyl, $(C_1-C_4)$-alkyl, carbamoyl, mono- or di($C_1-C_3$)-alkylaminocarbonyl or $(C_1-C_4)$-alkoxycarbonyl, or $R^7$ and $R^8$ form, together with the nitrogen atom, a morpholino, piperidinyl or pyrrolidinyl ring, or
$R^4$ represents $(C_1-C_6)$-alkyl which is substituted by a 5- to 6-membered aromatic, optionally benzo-fused heterocycle with up to 3 heteroatoms from the series S, N and/or O, it also being possible for a nitrogen-containing heterocycle to be bonded via the nitrogen atom, or is substituted by radicals of the formulae

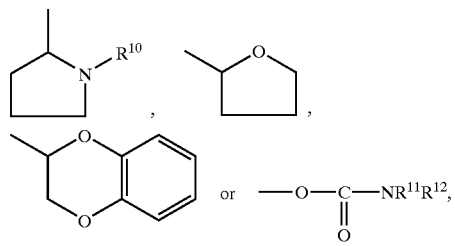

in which
$R^{10}$ denotes hydrogen or $(C_1-C_4)$-alkyl,
$R^{11}$ and $R^{12}$ are identical or different and denote hydrogen, $(C_1-C_3)$-alkyl or phenyl, where aforementioned $(C_1-C_3)$-alkyl and phenyl can optionally be substituted by 1 to 3 substituents selected from the group consisting of hydroxyl, $(C_1-C_3)$-alkoxy, chlorine and fluorine,
$R^5$ represents hydrogen or $(C_1-C_3)$-alkyl, $R^6$ represents phenyl which may optionally be substituted by one to two substituents selected from the group consisting of
chlorine, fluorine, phenyl, $(C_1-C_4)$-alkoxy, $(C_1-C_4)$-alkoxycarbonyl, $(C_1-C_3)$-alkylthio, hydroxyl, carboxyl, partially fluorinated $(C_1-C_4)$-alkoxy with up to 5 fluorine atoms,
radicals of the formulae

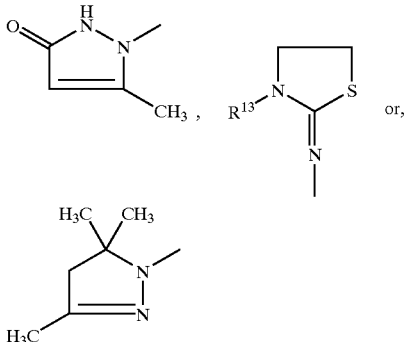

in which $R^{13}$ denotes hydrogen or $(C_1-C_3)$-alkyl, $(C_1-C_6)$-alkyl which is optionally substituted by a radical of the formula

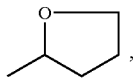

triazolyl,
morpholino, thiomorpholino, piperidinyl, pyrrolidinyl, azacycloheptanyl, azacyclobutany, each of which may optionally be substituted by 1 to 2 substituents selected from oxo, chlorine, fluorine, hydroxyl, $(C_1-C_4)$-alkoxycarbonyl, $(C_1-C_3)$-alkyl, chloro- or fluoro$(C_1-C_3)$-alkyl and hydroxy$(C_1-C_4)$-alkyl,

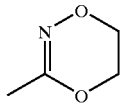

and groups of the formulae —$OR^{14}$, —$NR^{15}R^{16}$ or —CO—$NR^{17}R^{18}$,
in which
$R^{14}$ denotes a radical of the formula

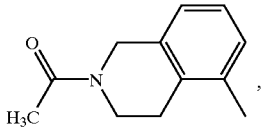

or phenyl which is in turn optionally substituted by a group of the formula —$NR^{19}R^{20}$,
in which
$R^{19}$ and $R^{20}$ are identical or different and denote hydrogen, $(C_1-C_3)$-alkyl or $(C_1-C_3)$-acyl,
or
$R^{14}$ denotes $(C_1-C_4)$-alkyl which is optionally substituted once to three times by hydroxyl,
$R^{15}$ and $R^{16}$ are identical or different and denote hydrogen, carbamoyl, mono- or di$(C_1-C_3)$ alkylaminocarbonyl, phenyl, $(C_1-C_3)$-acyl or $(C_1-C_3)$-alkyl, where $(C_1-C_3)$-alkyl is optionally substituted by $(C_1-C_3)$-alkoxy, $(C_1-C_3)$-acyl, by phenyl or pyridyl,
where aforementioned phenyl and aforementioned pyridyl are optionally substituted once to twice, identically or differently, by chlorine, fluorine and/or hydroxyl, and
$R^{17}$ and $R^{18}$ are identical or different and denote hydrogen or $(C_1-C_4)$-alkyl,
and the salts thereof.

In a preferred embodiment of the invention, $R^5$ in the compounds of the general formula (I) is hydrogen.

In another preferred embodiment of the invention, $R^2$ and $R^3$ in the compounds of the general formula (I) are hydrogen.

In another preferred embodiment of the invention, $R^6$ in the compounds of the general formula (I) is a para-substituted phenyl group which may optionally have another substituent. That is to say the compounds have the formula

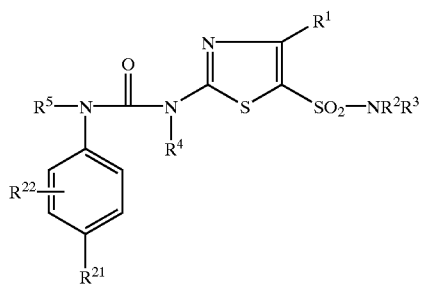

in which
$R^1$ to $R^5$ are each as defined above, and $R^{21}$ represents:
halogen, $(C_6-C_{10})$-aryl which may optionally be substituted by 1 to 3 substituents selected from $(C_1-C_6)$ alkanoyl, $(C_1-C_6)$-alkoxy, $(C_1-C_6)$-alkyl, halogen, $(C_1-C_6)$alkoxycarbonyl, nitro, halogeno$(C_1-C_6)$ alkyl, halogeno$(C_1-C_6)$alkoxy, amino, $(C_1-C_6)$ alkylthio, hydroxyl, carboxyl, carbamoyl, mono- or di$(C_1-C_6)$alkylaminocarbonyl, mono- or di$(C_1-C_6)$ acylamino, $(C_1-C_6)$alkylsulphinyl, $(C_1-C_6)$ alkylsulphonyl, and/or cyano, or $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy with up to 6 fluorine atoms,
radicals of the formulae

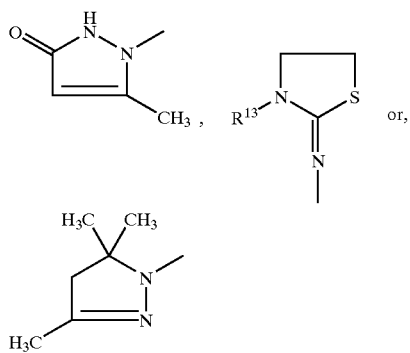

in which $R^{13}$ denotes hydrogen or $(C_1-C_6)$-alkyl, $(C_1-C_6)$-alkyl which is optionally substituted by a radical of the formula

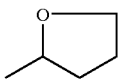

a 5- to 6-membered aromatic heterocycle which has up to 3 heteroatoms from the series S, N and/or O, is optionally bonded via a nitrogen atom and can optionally be substituted by 1 to 3 substituents selected from $(C_1-C_6)$alkanoyl, $(C_1-C_6)$-alkoxy, $(C_1-C_6)$-alkyl, halogen, $(C_1-C_6)$alkoxycarbonyl, nitro, halogeno$(C_1-C_6)$alkyl, halogeno$(C_1-C_6)$alkoxy, amino, $(C_1-C_6)$alkylthio, hydroxyl, carboxyl, carbamoyl, mono- or di$(C_1-C_6)$alkylaminocarbonyl, mono- or di$(C_1-C_6)$acylamino, $(C_1-C_6)$alkylsulphinyl, $(C_1-C_6)$alkylsulphonyl, and/or cyano, a 3- to 8-membered saturated or unsaturated, nonaromatic mono- or bicyclic heterocycle which has up to 3 heteroatoms from the series S, N and/or O, is optionally bonded via a nitrogen atom and may optionally be substituted by 1 to 3 substituents selected from oxo, halogen, hydroxyl, $(C_1-C_6)$-alkoxycarbonyl, $(C_1-C_6)$-alkoycarbonylamino, $(C_1-C_6)$-alkyl, halogeno$(C_1-C_6)$-alkyl and hydroxy $(C_1-C_6)$-alkyl, and groups of the formulae $-OR^{14}$, $-NR^{15}R^{16}$ or $-CO-NR^{17}R^{18}$, in which $R^{14}$ denotes a radical of the formula

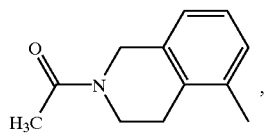

or denotes phenyl which in turn is optionally substituted by a group of the formula $-NR^{19}R^{20}$, in which $R^{19}$ and $R^{20}$ are identical or different and denote hydrogen, $(C_1-C_6)$-alkyl or $(C_1-C_6)$-acyl, or $R^{14}$ denotes $(C_1-C_6)$-alkyl which is optionally substituted once to three times by hydroxyl, $R^{15}$ and $R^{16}$ are identical or different and denote hydrogen, carbamoyl, mono- or di$(C_1-C_6)$alkylaminocarbonyl, phenyl, $(C_1-C_6)$-acyl or $(C_1-C_6)$-alkyl, where $(C_1-C_6)$-alkyl is optionally substituted by $(C_1-C_6)$-alkoxy, $(C_1-C_6)$-acyl, by phenyl or by a 5- to 6-membered aromatic heterocycle with up to 3 heteroatoms from the series S, N and/or O, where aforementioned phenyl and aforementioned aromatic heterocycle are optionally substituted once to three times, identically or differently, by halogen and/or hydroxyl, and $R^{17}$ and $R^{18}$ are identical or different and denote hydrogen or $(C_1-C_6)$-alkyl, and salts thereof $R^{22}$ can in this case have the above meaning of $R^{21}$ and be identical to or different from the latter, or may represent hydrogen, that is to say the phenyl radical is substituted only in the para position. $R^{22}$ is preferably hydrogen.

In another preferred embodiment, the invention relates to compounds which have the following formula

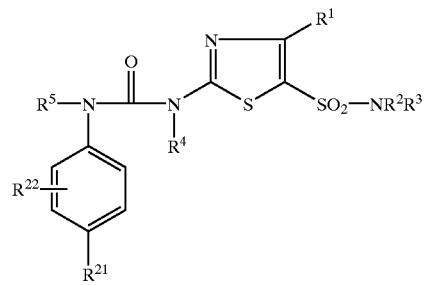

in which $R^1$ to $R^5$ are as defined above and $R^{21}$ represents halogen, $(C_6-C_{10})$-aryl, $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy with up to 6 fluorine atoms, radicals of the formulae

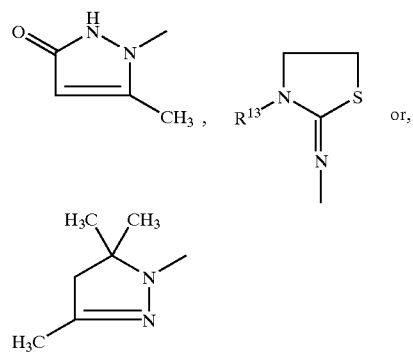

in which $R^{13}$ denotes hydrogen or $(C_1-C_6)$-alkyl, $(C_1-C_6)$-alkyl which is optionally substituted by a radical of the formula

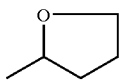

a 5- to 6-membered aromatic heterocycle which has up to 3 heteroatoms from the series S, N and/or O, is optionally bonded via a nitrogen atom and may optionally be substituted by one to three halogen atoms, a 3- to 8-membered saturated or unsaturated, nonaromatic heterocycle which has up to 3 heteroatoms from the series S, N and/or O, is optionally bonded via a nitrogen atom and may optionally be substituted by 1 to 3 substituents selected from oxo, halogen, hydroxyl, $(C_1-C_6)$-alkoxycarbonyl, $(C_1-C_6)$-alkyl, halogeno$(C_1-C_6)$-alkyl and hydroxy $(C_1-C_6)$-alkyl, or represents groups of the formulae $-OR^{14}$, $-NR^{15}R^{16}$ or $-CO-NR^{17}R^{18}$, in which $R^{14}$ denotes a radical of the formula

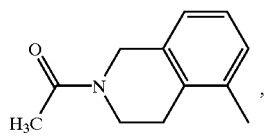

or denotes phenyl which in turn is optionally substituted by a group of the formula —$NR^{19}R^{20}$,
in which
$R^{19}$ and $R^{20}$ are identical or different and denote hydrogen, ($C_1$–$C_6$)-alkyl or ($C_1$–$C_6$)-acyl, or $R^{14}$ denotes ($C_1$–$C_6$)-alkyl which is optionally substituted once to three times by hydroxyl, $R^{15}$ and $R^{16}$ are identical or different and denote hydrogen, carbamoyl, mono- or di($C_1$–$C_6$) alkylaminocarbonyl, phenyl, ($C_1$–$C_6$)-acyl or ($C_1$–$C_6$)-alkyl, where ($C_1$–$C_6$)-alkyl is optionally substituted by ($C_1$–$C_6$)-alkoxy, ($C_1$–$C_6$)-acyl, by phenyl or by a 5- to 6-membered aromatic heterocycle with up to 3 heteroatoms from the series S, N and/or O, where aforementioned phenyl and aforementioned aromatic heterocycle are optionally substituted once to three times, identically or differently, by halogen and/or hydroxyl, and $R^{17}$ and $R^{18}$ are identical or different and denote hydrogen or ($C_1$–$C_6$)-alkyl, and $R^{22}$ may have the above meaning of $R^{21}$ and may be identical to or different from the latter, or $R^{22}$ is hydrogen.

$R^{22}$ can in this case have the above meaning of $R^{21}$ and be identical to or different from the latter, or may represent hydrogen, that is to say the phenyl radical is substituted only in the para position. $R^{22}$ is preferably hydrogen.

$R^{21}$ preferably represents phenyl, ($C_1$–$C_4$)-alkoxy or a 3- to 8-membered saturated or unsaturated, nonaromatic heterocycle which has up to 3 heteroatoms from the series S, N and/or O, is optionally bonded via a nitrogen atom and may optionally be substituted by 1 to 3 substituents selected from oxo, halogen, hydroxyl, ($C_1$–$C_6$)-alkoxycarbonyl, ($C_1$–$C_6$)-alkyl, halogeno($C_1$–$C_6$)-alkyl and hydroxy($C_1$–$C_6$)-alkyl.

The invention further relates to intermediates for preparing the compounds of the general formula (I), which have the formula (II):

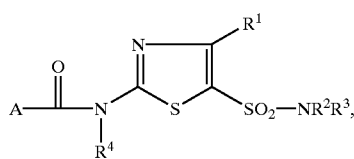

(II)

in which $R^1$, $R^2$, $R^3$ and $R^4$ have the meaning indicated above, and A represents a halogen atom.

A process for preparing the compounds according to the invention of the general formula (I) has additionally been found and is characterized in that

[A] compounds of the general formula (II)

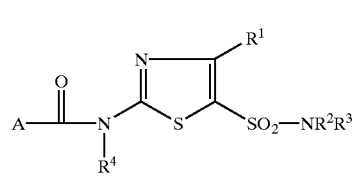

(II)

in which
$R^1$, $R^2$, $R^3$ and $R^4$ have the meaning indicated above, and
A represents halogen, preferably represents chlorine, are reacted with amines of the general formula (III)

 (III)

in which
$R^5$ and $R^6$ have the meaning indicated above,
in inert solvents, where appropriate in the presence of a base and/or aid, or

[B] isocyanates of the general formula (IV)

 (IV)

in which
$R^6$ has the meaning indicated above,
are reacted with thiazolylamines of the general formula (V)

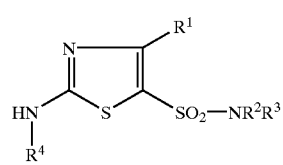

(V)

in which
$R^1$, $R^2$, $R^3$ and $R^4$ have the meaning indicated above,
in inert solvents and, in the case where $R^5$ is different from hydrogen, an alkylation is carried out by conventional processes.

The processes according to the invention can be illustrated by way of example by the following formula diagrams:

[A]

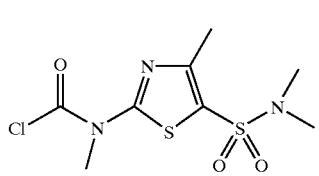

triethylamine
dioxane

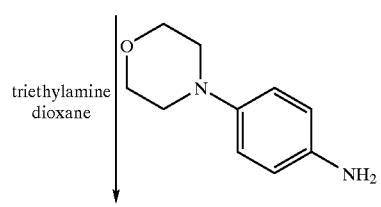

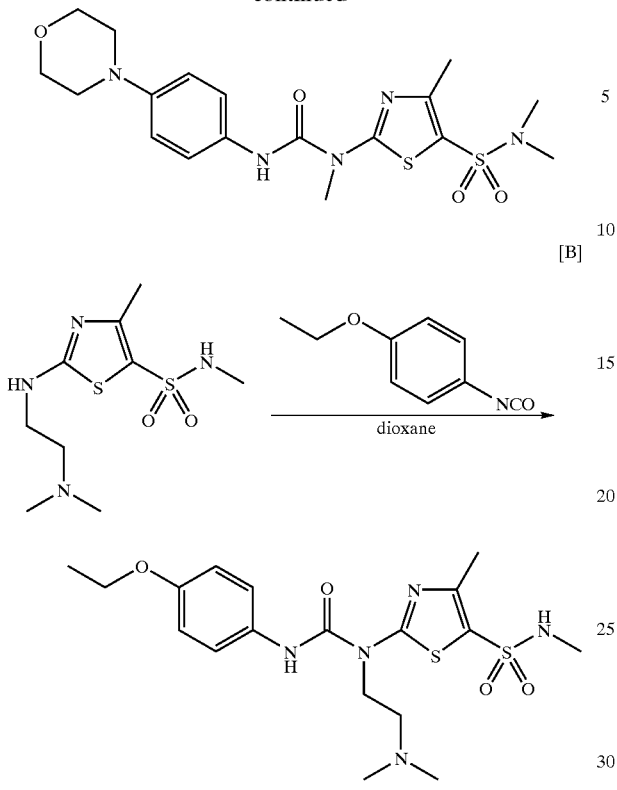

[B]

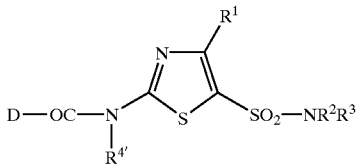

(VI)

in which
R¹, R² and R³ have the meaning indicated above, and
D represents (C₁–C₄)-alkyl, preferably represents methyl, being converted initially by an alkylation with compounds of the general formula (VII)

R⁴'—I (VII)

in which
R⁴' has the meaning indicated above for R⁴ but does not represent hydrogen,
in inert solvents and in the presence of a base into the compounds of the general formula (VIII)

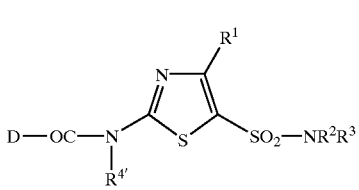

(VIII)

in which
R¹, R², R³, R⁴' and D have the meaning indicated above,
in another step by reaction with hydrochloric acid the compounds of the general formula (IX)

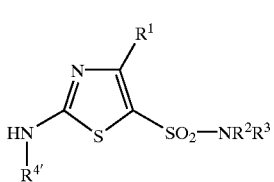

(IX)

in which
R¹, R², R³ and R⁴' have the meaning indicated above, being prepared and finally converted into ethers with trichloromethyl chloroformate.

Suitable solvents for processes [A] and [B] are conventional organic solvents which are not changed under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, dimethyl sulphoxide, dimethylformamide or acetonitrile. It is likewise possible to use mixtures of the solvents mentioned. Dioxane is preferred.

The bases which can be employed for process [A] according to the invention are in general inorganic or organic bases. These preferably include organic amines (trialkyl($C_1$–$C_6$) amines) such as triethylamine, or heterocycles such as 1,4-diaza-bicyclo[2.2.2]octane (DABCO), 1,8-diazabicyclo [5.4.0]undec-7-ene (DBU), pyridine, diaminopyridine, methylpiperidine or morpholine. Triethylamine is preferred.

The base is generally employed in an amount of 0.05 mol to 10 mol, preferably of 1 mol to 2 mol, based on 1 mol of the compound of the formula (II).

The processes according to the invention are generally carried out in a temperature range from −50° C. to +100° C., preferably from −30° C. to +60° C.

The processes according to the invention are generally carried out under atmospheric pressure. However, it is also possible to carry out the process under elevated pressure or under reduced pressure (for example in a range from 0.5 to 5 bar).

The compounds of the general formula (II) are novel and can be prepared by compounds of the general formula (VI)

Solvents suitable for the alkylation are conventional organic solvents which are not changed under the reaction conditions. These preferably include ethers such as diethyl ether, dioxane, tetrahydrofuran, glycol dimethyl ether or hydrocarbons such as benzene, toluene, xylene, hexane, cyclohexane or petroleum fractions or halogenohydrocarbons such as dichloromethane, trichloromethane, tetrachloromethane, dichloroethylene, trichloroethylene or chlorobenzene or ethyl acetate or triethylamine, pyridine, dimethyl sulphoxide, dimethylformamide, acetonitrile, acetone or nitromethane. It is likewise possible to use mixtures of the solvents mentioned. Dichloromethane, dimethyl sulphoxide and dimethylformamide are preferred.

Bases which can be employed for the process according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates, such as sodium carbonate, potassium carbonate or cesium carbonate, alkaline earth metal carbonates such as calcium carbonate, or alkali metal or alkaline earth metal alcoholates such as sodium or potassium methanolate, sodium or potassium ethanolate or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals such as sodium or their hydrides such as sodium hydride as bases. Sodium hydride is preferred.

The alkylation generally takes place in one of the solvents listed above, preferably in dimethylformamide in a temperature range from 0° C. to +70° C., preferably from 0° C. to 30° C. and atmospheric pressure.

The base is generally employed in an amount of 0.05 mol to 10 mol, preferably of 1 mol to 2 mol, based on 1 mol of the compound of the formula (VI).

The compounds of the general formula (IX) are prepared at the reflux temperature under atmospheric pressure.

Solvents suitable for the reaction with trichloromethyl chloroformate are in general ethers such as diethyl ether, dioxane, tetrahydrofuran or glycol dimethyl ether. Dioxane is preferred.

The reaction of compounds of the general formula (IX) with trichloromethyl chloroformate takes place initially at room temperature and subsequently at the reflux temperature of the particular ether.

The reaction is generally carried out under atmospheric pressure. However, it is also possible to carry out the process under elevated pressure or under reduced pressure (for example in a range from 0.5 to 5 bar).

The compounds of the general formula (VI) are known per se [compare DE 748376] or can be prepared by the methods published therein.

The compounds of the general formula (VII) are known.

The compounds of the general formulae (VIII) and (IX) are novel and can be prepared as described above.

The compounds of the general formula (V) are novel and can be prepared, for example, by compounds of the general formula (X)

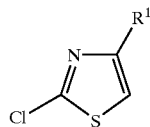

(X)

in which
$R^1$ has the meaning indicated above,
being converted by reaction with the chlorosulphonic acid/$SOCl_2$ system into the compounds of the general formula (XI)

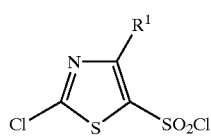

(XI)

in which $R^1$ has the meaning indicated above,
subsequently using amines of the general formula (XII)

$HNR^2R^3$ (XII)

in which
$R^2$ and $R^3$ have the meaning indicated above,
in inert solvents to prepare the compounds of the general formula (XIII)

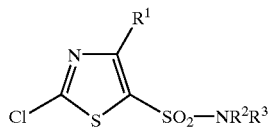

(XIII)

in which
$R^1$, $R^2$ and $R^3$ have the meaning indicated above,
and in a final step carrying out a reaction with amines of the general formula (XIV)

$H_2N$—$R^{4''}$ (XIV)

in which
$R^{4''}$ has the meaning indicated above for $R^{4'}$ and is identical to or different from the latter,
in inert solvents and in the presence of a base.

The reaction with chlorosulphonic acid/$SOCl_2$ takes place initially at room temperature and subsequently at the reflux temperature of the particular ether.

The reaction is generally carried out under atmospheric pressure. However, it is also possible to carry out the process under elevated pressure or under reduced pressure (for example in a range from 0.5 to 5 bar).

Solvents suitable for the reaction with amines of the general formula (XII) are alcohols such as, for example, methanol, ethanol, propanol and isopropanol. Methanol is preferred.

The reaction with the amines of the general formula (XIII) takes place initially at room temperature and subsequently at the reflux temperature of the particular ether.

The reaction is generally carried out under atmospheric atmospheric. However, it is also possible to carry out the process under elevated pressure or under reduced pressure (for example in a range from 0.5 to 5 bar).

The reaction with the compounds of the general formula (XIV) takes place in ethers such as, for example, diethyl ether, dioxane, tetrahydrofuran or glycol dimethyl ether. Dioxane is preferred.

Bases which can be employed are in general inorganic or organic bases. These preferably include organic amines (trialkyl($C_1$–$C_6$)amines) such as triethylamine, or heterocycles such as 1,4-diazabicyclo[2.2.2]octane (DABCO), 1,8-diazabicyclo-[5.4.0]undec-7-ene (DBU), pyridine, diaminopyridine, methylpiperidine or morpholine. Triethylamine is preferred.

The base is generally employed in an amount of 0.05 mol to 10 mol, preferably of 1 mol to 2 mol, based on 1 mol of the compound of the formula (XIII).

The compounds of the general formula (X) are in some cases known or can be prepared by conventional methods [compare Hantzsch, Chem. Ber. 1927, 60, 2544].

The compounds of the general formula (XI) and (XIII) are novel and can be prepared as described above.

The amines of the general formulae (XII) and (XIV) are known.

The compounds of the general formulae (III) and (IV) are disclosed in the literature.

Biphenylylamine derivatives of the formula (III) from which it is possible also to prepare the corresponding isocyanates (IV) can be prepared by known transition metal-catalysed coupling reactions such as, for example, the Suzuki or Stille coupling. The following reaction diagram illustrates by way of example the synthesis of a biphenylylamine derivative by the palladium-catalysed Suzuki coupling reaction, which is known per se, of a halogenoaromatic compound with the respective boronic acid.

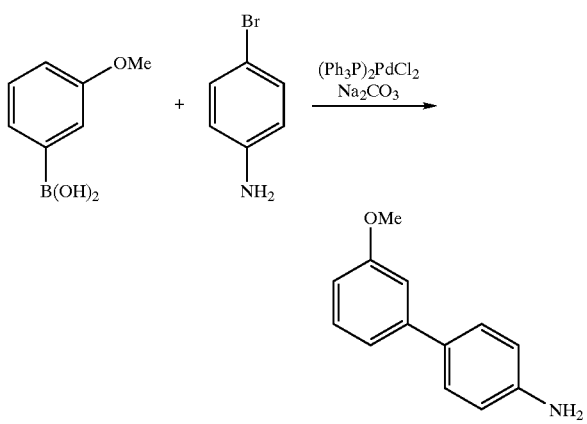

The pyridylphenylamine derivatives of the formula (III) are disclosed in the literature.

The invention further relates to the use of the 2-[(aminocarbonyl)amino]-1,3-thiazole-5-sulphonamide derivatives for preparing pharmaceuticals. 2-[(Aminocarbonyl)amino]-1,3-thiazole-5-sulphonamide derivatives are compounds derived from 2-[(aminocarbonyl)amino]-1,3-thiazole-5-sulphonamide by replacement of one or more hydrogen atoms. The 2-[(aminocarbonyl)amino]-1,3-thiazole-5-sulphonamide derivatives are preferably used to produce compositions for the treatment and/or prevention of viral infections in humans or animals, particularly preferably to produce compositions for the treatment and/or prevention of infections in humans or animals by herpes viruses.

The compounds according to the invention of the general formulae (I etc.) show a surprising range of effects which could not have been predicted. They show an antiviral effect on representatives of the Herpesyiridae group, in particular on herpes simplex viruses (HSV). They are thus suitable for the treatment and prophylaxis of disorders caused by herpes viruses, in particular disorders caused by herpes simplex viruses in humans or animals.

In Vitro Activity

Virus and Cells

HSV (HSV-1 Walki, HSV-1F or HSV-2G) was replicated on Vero cells (ATCC CCL-81) under the following conditions: the cells were grown in M199 medium (5% fetal calf serum, 2 mM glutamine, 100 IU/ml penicillin, 100 µg/ml streptomycin) in cell culture bottles at 37° C. and 5% $CO_2$. The cells were split 1:4 on each of two occasions each week. For the infection, the medium was removed, and the cells were washed with Hank's solution, detached with 0.05% trypsin, 0.02% EDTA (Seromed L2143) and incubated at a density of $4\times10^5$ cells per ml under the conditions mentioned above for 24 hours. The medium was then removed, and the virus solution was added at an m.o.i. of <0.05 in a volume of 2 ml per 175 cm² of surface area. After incubation under the conditions mentioned for one hour, the medium was made up to a volume of 50 ml per 175 cm² bottle. 3 days after the infection the cultures showed clear signs of a cytopathic effect. The virus was released by freezing (–80° C.) and thawing (37° C.) twice. The cell debris was removed by centrifugation (300 g, 10 min, 4° C.) and the supernatant was frozen in aliquots at –80° C.

The virus titre was determined by a plaque assay. For this purpose, Vero cells were seeded in a density of $4\times10^5$ cells per well in 24-well plates and, after incubation (37° C., 5% $CO_2$) for 24 hours, infected with dilutions of the virus stock of from $10^{-2}$ to $10^{-12}$ (100 µl inoculum). 1 hour after the infection, the medium was removed and the cells were covered with 1 ml of overlay medium (0.5% methylcellulose, 0.225 M sodium bicarbonate, 2 mM glutamine, 100 IU/ml penicillin, 100 µg/ml streptomycin, 5% fetal calf serum in MEM Eagle Medium with Earles Salts) and incubated for 3 days. The cells were subsequently fixed with 4% formalin for 1 hour, washed with water, stained with Giemsa (Merck) for 30 min and subsequently washed and dried. The virus titre was determined using a plaque viewer. The virus stocks used for the experiments had a titre of $1\times10^6$/ml–$1\times10^8$/ml.

The anti-HSV effect was determined in a screening test system in 96-well microtitre plates with the assistance of various cell lines of neuronal, lymphoid and epithelial origin, such as, for example, Vero (African green monkey kidney cell line), MEF (murine embryonic fibroblasts), HELF (human embryonic fibroblasts), NT2 (human neuronal cell line) or Jurkat (human lymphoid T-cell line). The effect of the substances on the extent of the cytopathogenic effect was determined by comparison with the reference substance aciclovir sodium (Zovirax$^R$), a clinically approved anti-herpes chemotherapeutic agent.

The substances dissolved (50 mM) in DMSO (dimethyl sulphoxide) are investigated on microtitre plates (for example 96-well MTP) in final concentrations of 250–0.5 µM (micromolar) in duplicate determinations (4 substances/plate). For potent substances, the dilutions are continued over several plates as far as 0.5 pM (picomolar). Toxic and cytostatic effects of the substance are also recorded. After the appropriate dilutions of the substance (1:2) on the microtitre plate, a suspension of cells ($1\times10^4$ cells per well) such as, for example, Vero cells in M199 (medium 199) with 5% fetal calf serum, 2 mM glutamine and optionally 100 IU/ml penicillin and 100 µg/ml streptomycin or MEF cells in EMEM (Eagle's minimum essential medium) with 10% fetal calf serum, 2 mM glutamine and optionally 100 IU/ml penicillin and 100 µg/ml streptomycin, or HELF cells in EMEM with 10% fetal calf serum, 2 mM glutamine and optionally 100 IU/ml penicillin and 100 µg/ml streptomycin, or NT2 and Jurkat cells in DMEM (4.5 mg/l glucose plus pyridoxine) with 10% fetal calf serum, 2 mM glutamine, 1 mM sodium pyruvate, nonessential amino acids and optionally 100 IU/ml penicillin and 100 µg/ml streptomycin is put in each well, and the cells in the relevant wells are infected with an appropriate amount of virus (HSV-1 F or HSV-2 G with an m.o.i (multiplicity of infection) of 0.0025 for HELF, Vero and MEF cells and with an m.o.i of 0.1 for NT2 and Jurkat cells). The plates are then incubated at 37° C. in a $CO_2$ incubator (5% $CO_2$) for several days. After this time, the cell lawn of, for example, Vero cells in the substance-free virus controls, starting from 25 infectious centres, is completely lysed or destroyed (100% CPE) by the cytopathogenic effect of the HSV viruses. The plates are initially evaluated optically using a microscope and then analysed with a fluorescent dye. For this purpose, the cell culture supernatant is aspirated out of all the wells of the MTP and charged with 200 μl of PBS washing solution. The PBS is in turn aspirated out, and all the wells are charged with 200 μl of fluorescent dye solution (fluorescein diacetate, 10 μg/ml in PBS). After an incubation time of 30–90 min, the test plates are measured in a fluorimeter at an excitation wavelength of 485 nm and an emission wavelength of 538 nm.

The results for some compounds are summarized in the following table:

TABLE

| Example | $IC_{50}$ HSV-1 F/Vero | $IC_{50}$ HSV-2 G/Vero |
|---|---|---|
| 43 | 0.5 μM | 1.5 μM |
| 123 | 1 nM | 5 nM |
| 94 | 20 nM | 50 nM |
| 2 | 0.2 μM | 1 μM |
| Zovirax (Aciclovir sodium) | 1 μM | 3 μM |

$IC_{50}$ here means the half-maximum fluorescence intensity in relation to the uninfected cell control.

The 2-[(aminocarbonyl)amino]-1,3-thiazole-5-sulphonamide derivatives of the invention preferably have an $IC_{50}$ of less than 50 μM, preferably of less than 25 μM and very particularly preferably of less than 10 μM.

The compounds according to the invention thus represent valuable active substances for the treatment and prophylaxis of disorders caused by herpes virus, in particular herpes simplex virus. Areas of indication which may be mentioned by way of example are:

1) Treatment and prophylaxis of herpes infections, in particular herpes simplex infections, in patients with pathological states such as herpes labialis, herpes genitalis, and HSV-related keratitis, encephalitis, pneumonia, hepatitis etc.
2) Treatment and prophylaxis of herpes infections, in particular herpes simplex infections, in immunosuppressed patients (for example AIDS patients, cancer patients, patients with genetically related immunodeficiency, transplant patients)
3) Treatment and prophylaxis of herpes infections, in particular herpes simplex infections, in neonates and infants
4) Treatment and prophylaxis of herpes infections, in particular herpes simplex infections, in patients positive for herpes, and in particular for herpes simplex, to suppress recurrence (suppression therapy)

In Vivo Effect
Animals
6-week old female mice, strain BALB/cABom, were purchased from a commerical breeder (Bomholtgard Breeding and Research Centre Ltd.).
Infection
The animals were anaesthetized with diethyl ether (Merck) in a sealed glass vessel. 50 μl of a dilution of the virus stock (infectious dose $5 \times 10^4$ pfu) were introduced into the nose of the anaesthetized animals with an Eppendorf pipette. This infectious dose leads to death of 90–100% of the animals after an average of between 5 and 8 days due to a generalized infection with prominent respiratory and central nervous symptoms.
Treatment and Evaluation
6 hours after the infection, the animals were treated with doses of 0.1–100 mg/kg of body weight 3 times a day at 7.00 h, 14.00 h and 19 h over a period of 5 days. The substances were dissolved in DMSO and resuspended in Tylose/PBS (Hoechst) (final concentration 1.5% DMSO, 0.5% Tylose in PBS).

After the last administration, the animals were observed further and the times of death were recorded.

A comparison of the graphs of survival revealed that the compound of Example 43, for example, has an $ED_{50}$ of 30–40 mg/kg, where $ED_{50}$ means that 50% of the animals survive at this dose.

The novel active substances can be converted in a known manner into conventional formulations such as tablets, coated tablets, pills, granules, aerosols, syrups, emulsions, suspensions and solutions using inert, nontoxic, pharmaceutically suitable carriers and solvents. In these, the therapeutically active compound should in each case be present in a concentration of about 0.5 to 90% by weight of the complete mixture, that is to say in amounts which suffice to reach the dosage range indicated.

The formulations are produced, for example, by extending the active substances with solvents and/or carriers, where appropriate with use of emulsifiers and/or dispersants, it being possible for example in the case of use of water as diluent where appropriate to use organic solvents as auxiliary solvents.

Administration takes place in a conventional way, preferably orally, parenterally or topically, in particular perlingually or intravenously.

In the case of parenteral administration, solutions of the active substance using suitable liquid carrier materials can be employed.

It has generally proved advantageous in order to achieve effective results to administer amounts of about 0.001 to 20 mg/kg, preferably about 0.01 to 10 mg/kg of body weight on intravenous administration, and the dosage on oral administration is about 0.01 to 30 mg/kg, preferably 0.1 to 20 mg/kg of body weight.

It may, nevertheless, be necessary where appropriate to deviate from the amounts mentioned, in particular depending on the body weight and the nature of the administration route, on the individual behaviour and response to the medicament, the nature of the formulation and the time or interval over which administration takes place. Thus, in some cases, it may be sufficient to make do with less than the aforementioned minimum amount, where in other cases the upper limit mentioned must be exceeded. In the case of administration of larger amounts it may be advisable to divide these into a plurality of individual doses over the day.

It may, where appropriate, be worthwhile to combine the compounds according to the invention with other active substances.

Starting Compounds

EXAMPLE I

N-{5-[(Dimethylamino)sulphonyl]-4-methyl-1,3-thiazol-2-yl}-N-methylacetamide

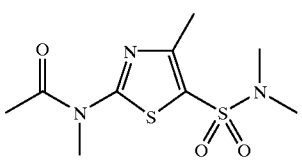

6.0 g of sodium hydride (60% dispersion in mineral oil, 0.151 mol) were added dropwise at 0° C. to a solution of 36.2 g (0.137 mol) of N-{5-[(dimethylamino)-sulphonyl]-4-methyl-1,3-thiazol-2-yl}acetamide in dimethylformamide. Then 21.4 g (0.151 mol) of methyl iodide were added dropwise from a syringe. After TLC showed complete conversion, the mixture was quenched by adding a saturated ammonium chloride solution. The mixture was evaporated to dryness, and the residue was taken up with water, stirred for 16 h and filtered off. After the residue had been dried in vacuo it was further purified by chromotography on silica gel with toluene/ethyl acetate (15–66% ethyl acetate) as mobile phase. 31.0 g of a white powder were obtained (Rf=0.43 (toluene/ethyl acetate=1/2), yield 74%).

EXAMPLE II

N,N,4-Trimethyl-2-(methylamino)-1,3-thiazole-5-sulphonamide

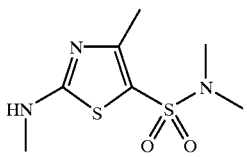

31 g (0.111 mol) of N-{5-[(Dimethylamino)sulphonyl]-4-methyl-1,3-thiazol-2-yl}-N-methylacetamide were suspended in 500 ml of 4N hydrochloric acid and heated to reflux until TLC (toluene/ethyl acetate 1/2) showed that the reaction was complete. The mixture was washed with dichloromethane, made basic by adding 20% strength sodium hydroxide solution and extracted with dichloromethane. The organic phase was then dried over sodium sulphate and concentrated. The crude product was further purified by chromatography on silica gel with toluene/ethyl acetate (50–85% ethyl acetate) as mobile phase. After the solvent had been distilled off, 22.9 g of a solid were obtained. (Rf=0.37 (toluene/ethyl acetate=1/2), yield 87.7%)

EXAMPLE III

5-[(Dimethylamino)sulphonyl]-4-methyl-1,3-thiazol-2-yl(methyl)carbamoyl chloride

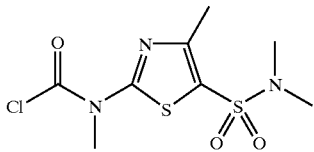

15.4 g (78 mmol) of trichloromethyl chloroformate ("diphosgene") were added at room temperature to a solution of 22.9 g (97 mmol) of N,N,4-trimethyl-2-(methylamino)-1,3-thiazole-5-sulphonamide in 360 ml of dioxane, and the mixture was heated to reflux until a homogeneous solution was obtained, and TLC showed that no starting material remained. After removal of the solvent in vacuo, 29.0 g of the product were obtained in the form of an oil. (Yield 100%, NMR (CDCl₃): 3.89 (3H), 2.81 (6H), 2.62 (3H) ppm).

EXAMPLE IV

2-Chloro-4-methyl-1,3-thiazole-5-sulphonyl chloride

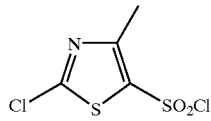

150 g (1.12 mol) of 2-chloro-4-methyl-1,3-thiazole are added dropwise at room temperature to a solution of 331 g (2.81 mmol) of thionyl chloride in 653 g (5.61 mmol) of chlorosulphonic acid. The solution is heated to reflux for 48 h. The mixture is then poured into 3 l of ice-water and extracted with 4×400 ml of dichloromethane. The combined organic phases are washed with 2.5 l of water, dried over sodium sulphate and concentrated. Distillation of the crude product results in 233.7 g of product in the form of an oil. (Boiling point 87–96° C., 0.7 mbar, yield 89.6%).

EXAMPLE V

2-Chloro-N,4-dimethyl-1,3-thiazole-5-sulphonamide

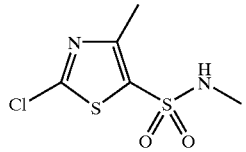

177 ml of a solution of methylamine in methanol (2 M, 0.354 mol) are added at 0° C. to a solution of 41 g (0.177 mol) of 2-chloro-4-methyl-1,3-thiazole-5-sulphonyl chloride in 360 ml of dichloromethane. The mixture is stirred at 0° C. for 30 min, 1.8 l of water are added, and the mixture is extracted 5 times with 400 ml of dichloromethane each time. The combined organic phases are dried over sodium sulphate, and the solvent is distilled off. 39.93 g of an oil, which solidifies on standing, are obtained (Rf=0.43 (toluene/ethyl acetate=2/1), yield 99.7%)

EXAMPLE VI

2-{[2-(Dimethylamino)ethyl]amino}-N,4-dimethyl-1,3-thiazole-5-sulphonamide

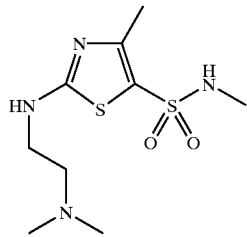

A solution of 5.0 g (22.1 mmol) of 2-chloro-N,4-dimethyl-1,3-thiazole-5-sulphonamide, 2.92 g (33.1 mmol) of 2-N,N-dimethylaminoethylamine and 6.10 ml of triethylamine in 6.65 ml of dioxane is stirred at 100° C. for 16 h. Then 20 ml of water are added and the mixture is extracted with 3×100 ml of dichloromethane. The combined organic phases are dried over sodium sulphate and concentrated. Chromatography of the crude product on silica gel with a mixture of chloroform and methanol as mobile phase (0–30% methanol) results in 3.05 g of an oil. (Rf=0.04 (chloroform/5% methanol), yield 49.7%).

Preparation Examples

EXAMPLE 1

N,N,4-Trimethyl-2-{methyl[4-morpholinoanilinocarbonyl]amino}-1,3-thiazole-5-sulphonamide

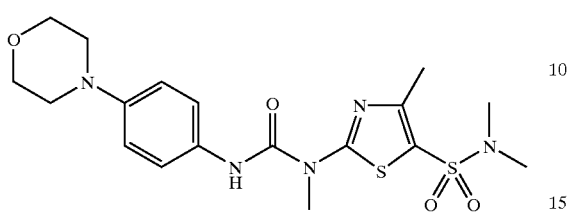

12.0 g (40.3 mmol) of 5-[(dimethylamino)sulphonyl]-4-methyl-1,3-thiazol-2-yl(methyl)carbamoyl chloride and 4.08 g (40.3 mmol) of triethylamine were dissolved in 150 ml of dioxane, and 7.18 g (40.3 mmol) of 4-morpholinoaniline, dissolved in 60 ml of dioxane, were added dropwise. The mixture was stirred at room temperature for 12 h, and the resulting precipitate was filtered off and dissolved in a dichloromethane/water (1:1) solvent mixture. The organic phase was separated off, dried over sodium sulphate and concentrated in vacuo.

Yield: 12.4 g (70%)

Melting point: 191° C.

EXAMPLE 2

2-{[2-(Dimethylamino)ethyl][(4-ethoxyanilino)carbonyl]amino}-N,4-dimethyl-1,3-thiazole-5-sulphonamide

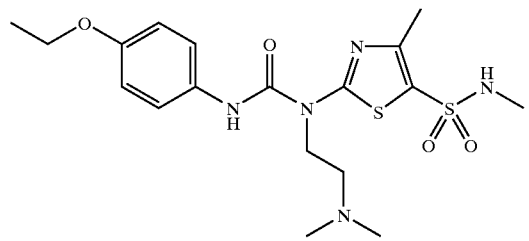

1.0 g (3.59 mmol) of 2-{[2-dimethylaminoethyl]amino}-N,4-dimethyl-1,3-thiazole-5-sulphonamide and 586 mg (3.59 mmol) of 4-ethoxyphenyl isocyanate are dissolved in 30 ml of dioxane and stirred at room temperature for 12 h. The mixture is then concentrated in vacuo, and the residue is recrystallized from 2-propanol.

Yield: 1.19 g (75%)

Melting point: 153° C.

The compounds listed in the following table are prepared analogously to the methods detailed above:

| Ex. No. | Structure | m.p. [° C.] | LC/MS method | Retention time | MS (M + H) | Molecular weight | Rf |
|---|---|---|---|---|---|---|---|
| 3 | 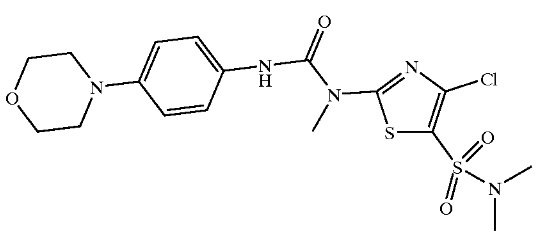 | 197 | | | | | |
| 4 | 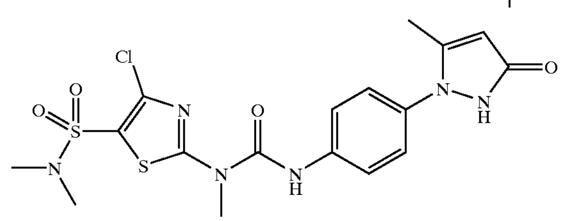 | | | | | | |
| 5 | 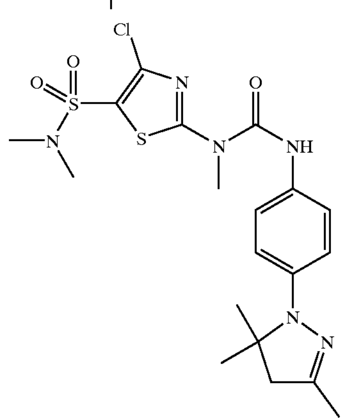 | | | | | | |

| Ex. No. | Structure | m.p. [° C.] | LC/MS method | Retention time | MS (M + H) | Molecular weight | Rf |
|---|---|---|---|---|---|---|---|
| 6 | 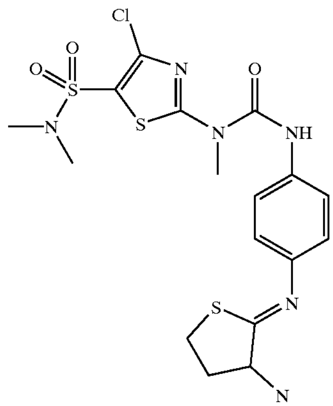 | | | | | | |
| 7 | 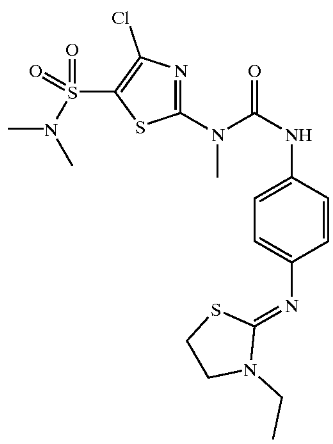 | | | | | | |
| 8 | 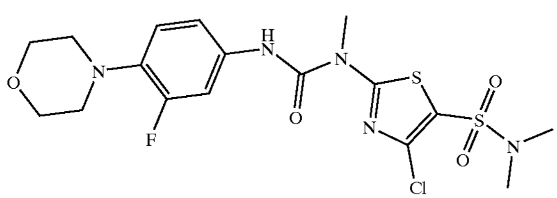 | 196 | | | | | |
| 9 | 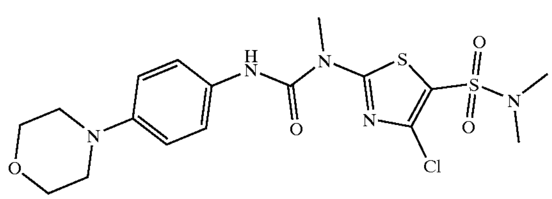 | 210 | | | | | |
| 10 | 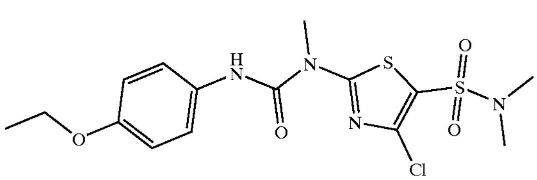 | 215 | | | | | |

| Ex. No. | Structure | m.p. [° C.] | LC/MS method | Retention time | MS (M + H) | Molecular weight | Rf |
|---|---|---|---|---|---|---|---|
| 11 | 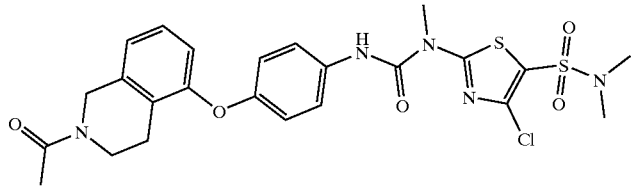 | 163 | | | | | |
| 12 | 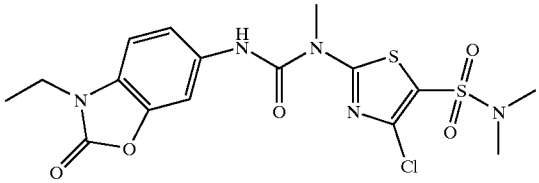 | 232 | | | | | |
| 13 | 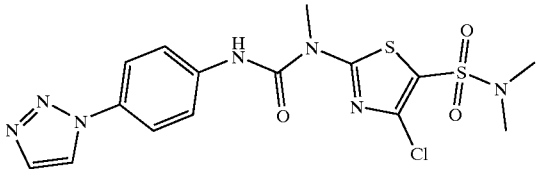 | 225 | | | | | |
| 14 | 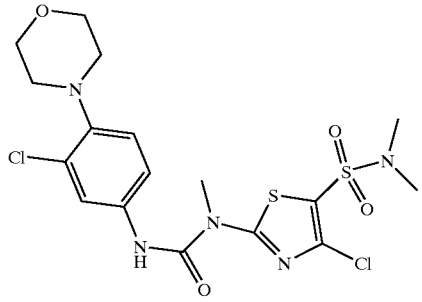 | 203 | | | | | |
| 15 | 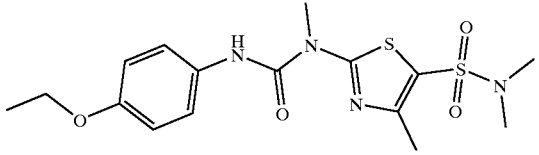 | 168 | | | | | |
| 16 | 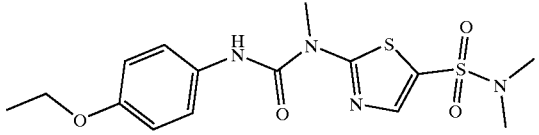 | 194 | | | | | |

-continued

| Ex. No. | Structure | m.p. [° C.] | LC/MS method | Retention time | MS (M + H) | Molecular weight | Rf |
|---|---|---|---|---|---|---|---|
| 17 | 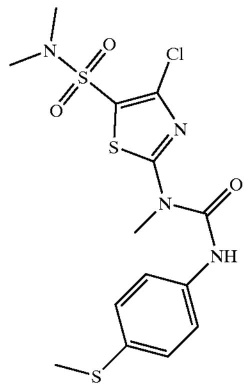 | 194 | | | | | |
| 18 | 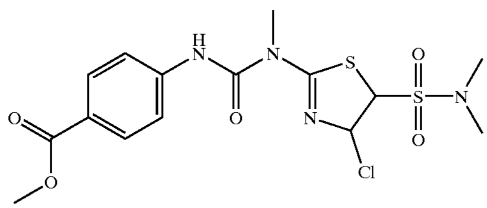 | 220 | | | | | |
| 19 | 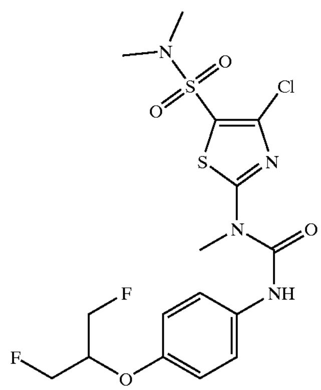 | 164 | | | | | |
| 20 | 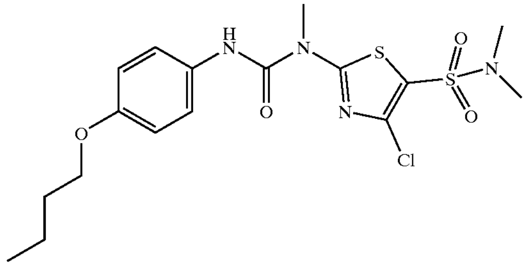 | 140 | | | | | |
| 21 | 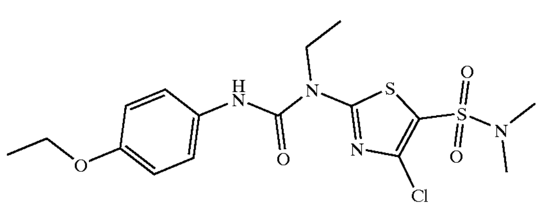 | | | | | | |

-continued

| Ex. No. | Structure | m.p. [° C.] | LC/MS method | Retention time | MS (M + H) | Molecular weight | Rf |
|---|---|---|---|---|---|---|---|
| 22 | 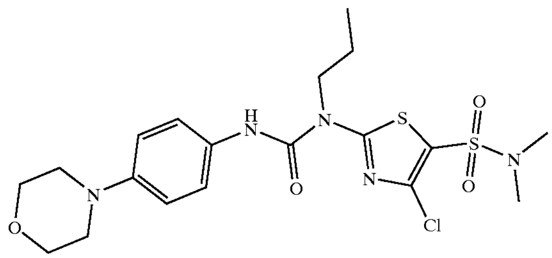 | | | | | | |
| 23 | 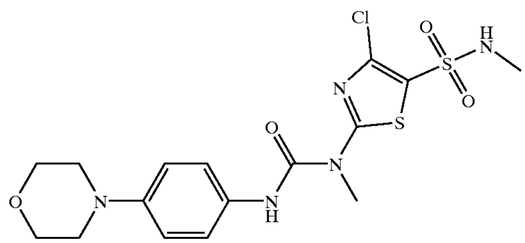 | 228 | | | | | |
| 24 | 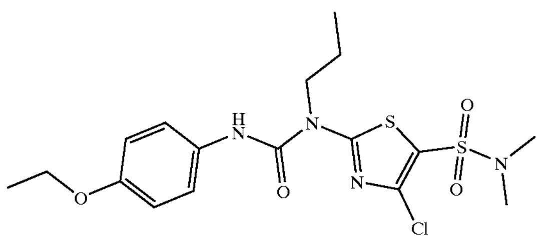 | 132 | | | | | |
| 25 | 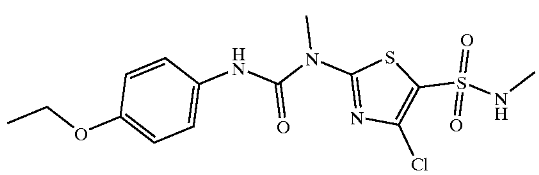 | 183 | | | | | |
| 26 | 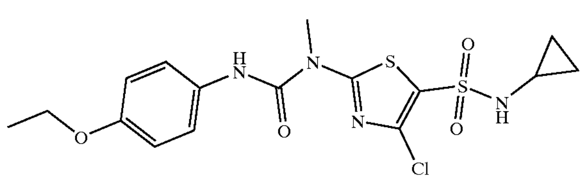 | 183 | | | | | |
| 27 | 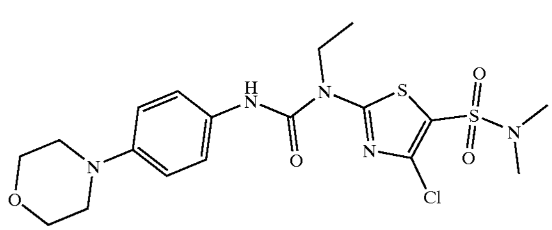 | 190 | | | | | |

-continued

| Ex. No. | Structure | m.p. [° C.] | LC/MS method | Retention time | MS (M + H) | Molecular weight | Rf |
|---|---|---|---|---|---|---|---|
| 28 | 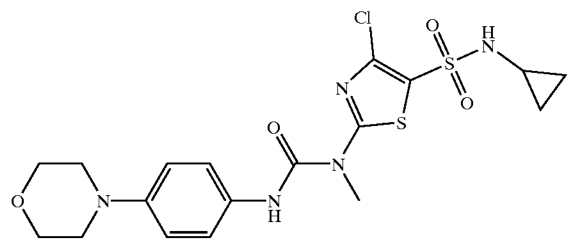 | 241 | | | | | |
| 29 | 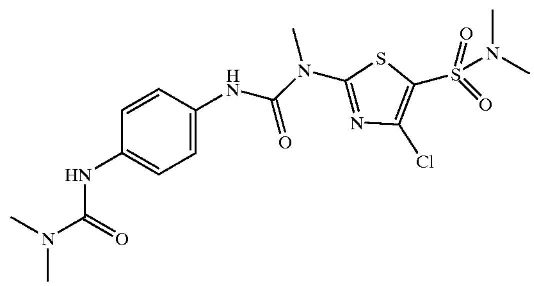 | 240 | | | | | |
| 30 | 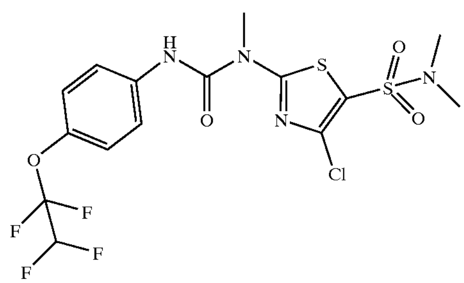 | 168 | | | | | |
| 31 | 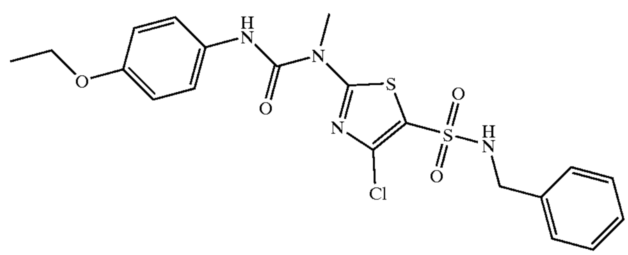 | 170 | | | | | |
| 32 | 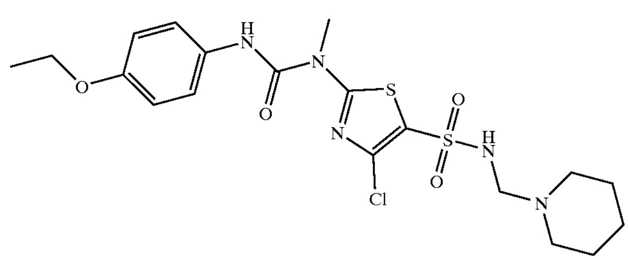 | 183 | | | | | |

-continued

| Ex. No. | Structure | m.p. [° C.] | LC/MS method | Retention time | MS (M + H) | Molecular weight | Rf |
|---|---|---|---|---|---|---|---|
| 33 | 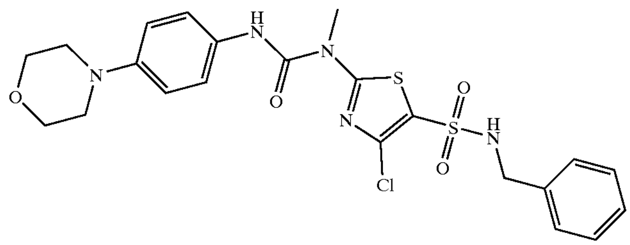 | 201 | | | | | |
| 34 | 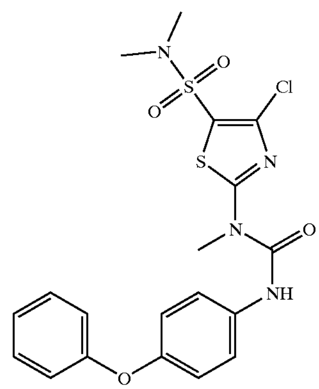 | 127 | | | | | |
| 35 | 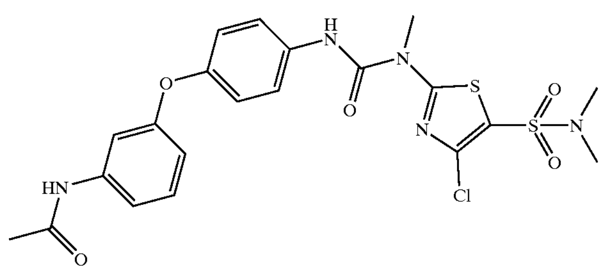 | 219 | | | | | |
| 36 | 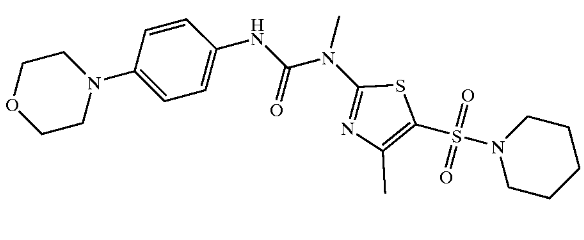 | 206 | | | | | |
| 37 | 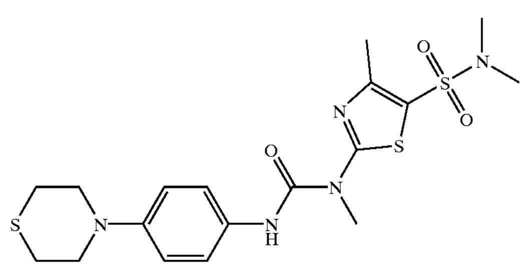 | 196 | | | | | |

-continued

| Ex. No. | Structure | m.p. [° C.] | LC/MS method | Retention time | MS (M + H) | Molecular weight | Rf |
|---|---|---|---|---|---|---|---|
| 38 | 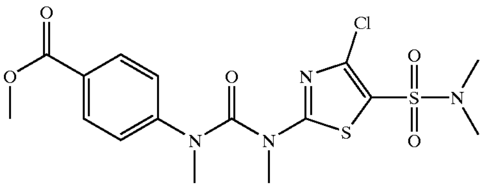 | 168 | | | | | |
| 39 | 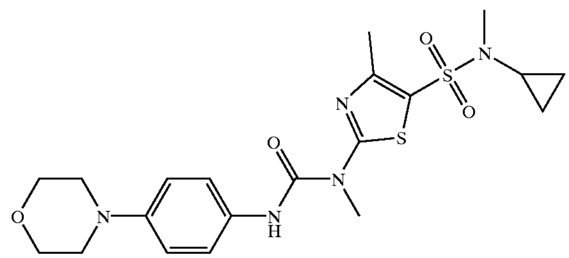 | 198 | | | | | |
| 40 | 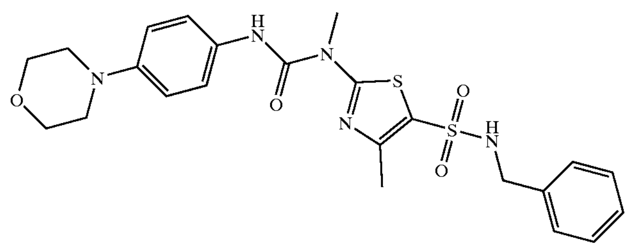 | 216 | | | | | |
| 41 | 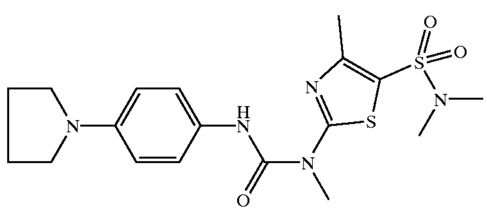 | | | | | | |
| 42 | 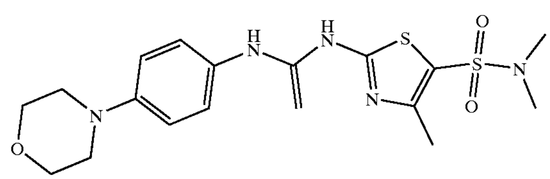 | 188 | | | | | |
| 43 | 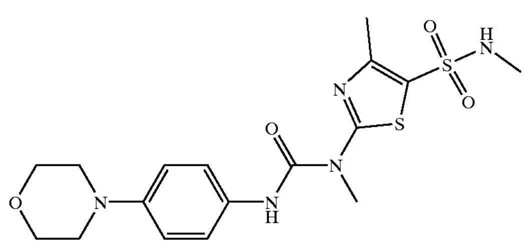 | 218 | | | | | |
| 44 | 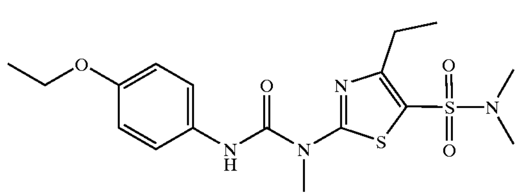 | 176 | | | | | |

-continued

| Ex. No. | Structure | m.p. [° C.] | LC/MS method | Retention time | MS (M + H) | Molecular weight | Rf |
|---|---|---|---|---|---|---|---|
| 45 | 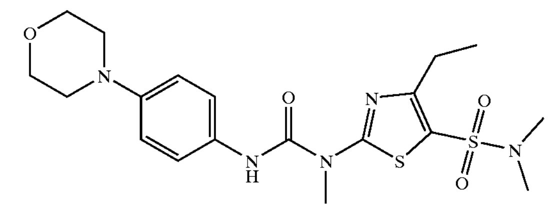 | 199 | | | | | |
| 46 | 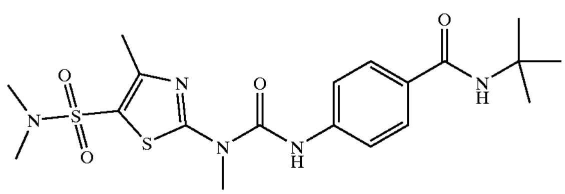 | | | | | | 0.17 (EP1) |
| 47 | 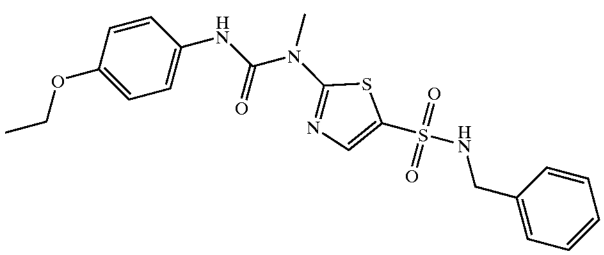 | 171 | | | | | |
| 48 | 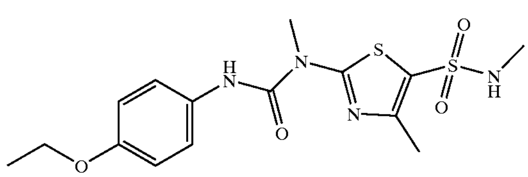 | 179 | | | | | |
| 49 | 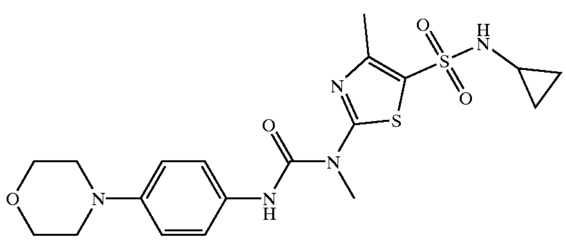 | 235 | | | | | |
| 50 | 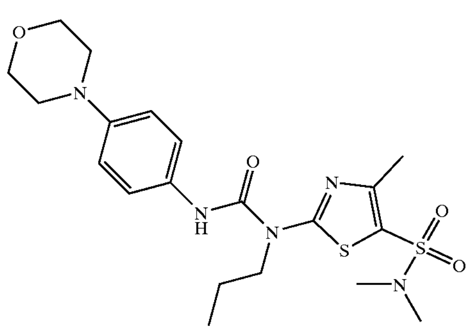 | 161 | | | | | |

-continued
| Ex. No. | Structure | m.p. [° C.] | LC/MS method | Retention time | MS (M + H) | Molecular weight | Rf |
|---|---|---|---|---|---|---|---|
| 51 | 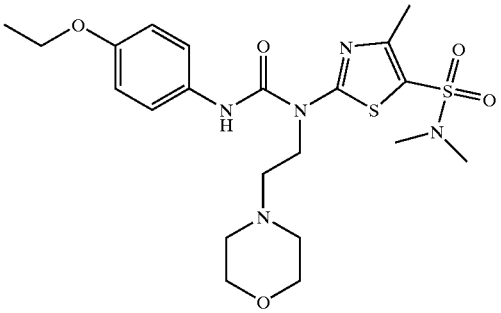 | 204 | | | | | |
| 52 | 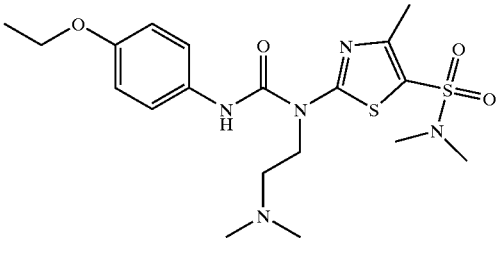 | 163 | | | | | |
| 53 | 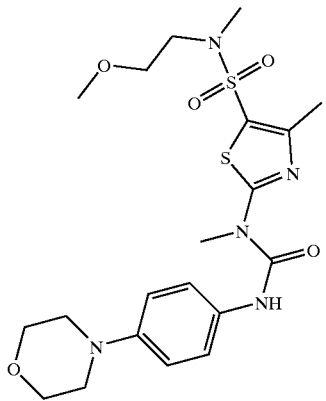 | 156 | | | | | |
| 54 | 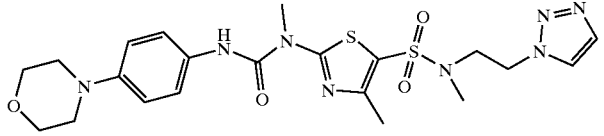 | 172 | | | | | |
| 55 | 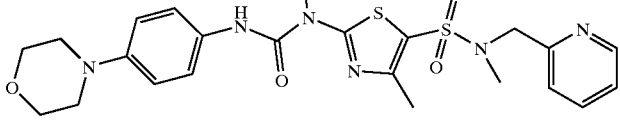 | 148 | | | | | |
| 56 | 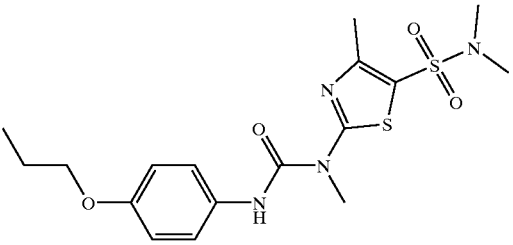 | 147 | | | | | |

| Ex. No. | Structure | m.p. [° C.] | LC/MS method | Retention time | MS (M + H) | Molecular weight | Rf |
|---|---|---|---|---|---|---|---|
| 57 | 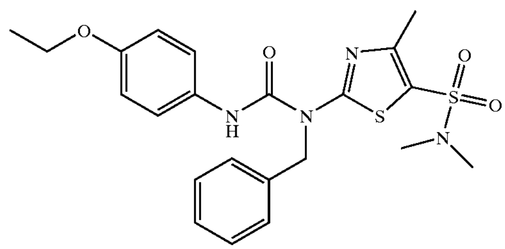 | 187 | | | | | |
| 58 | 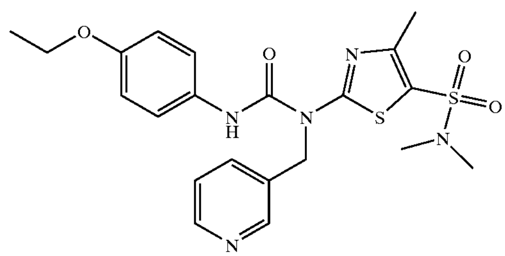 | 180 | | | | | |
| 59 | 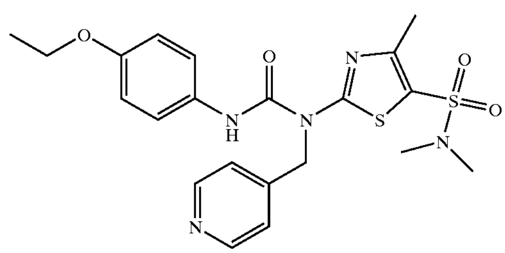 | 188 | | | | | |
| 60 | 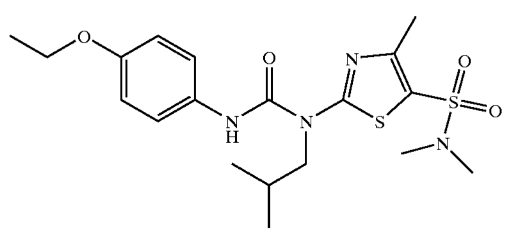 | 173 | | | | | |
| 61 | 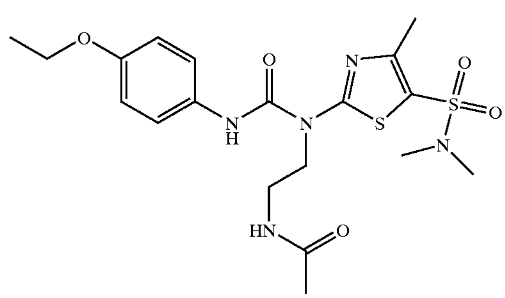 | 184 | | | | | |

-continued

| Ex. No. | Structure | m.p. [° C.] | LC/MS method | Retention time | MS (M + H) | Molecular weight | Rf |
|---|---|---|---|---|---|---|---|
| 62 | 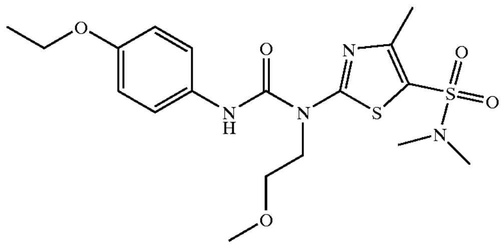 | 162 | | | | | |
| 63 | 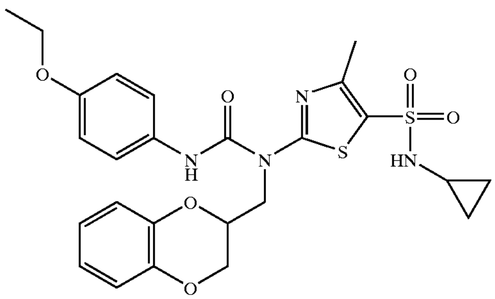 | 170 | | | | | |
| 64 | 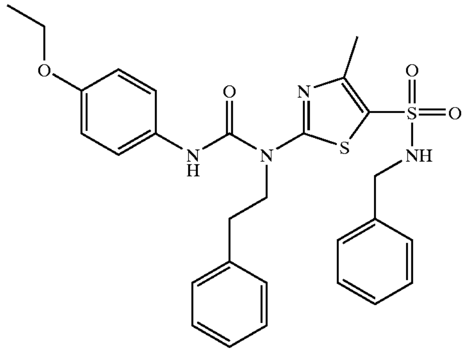 | 156 | | | | | |
| 65 | 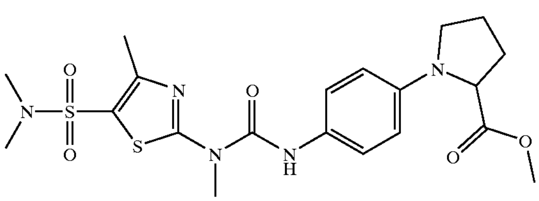 | | | | | | 0.54 (EP2) |
| 66 | 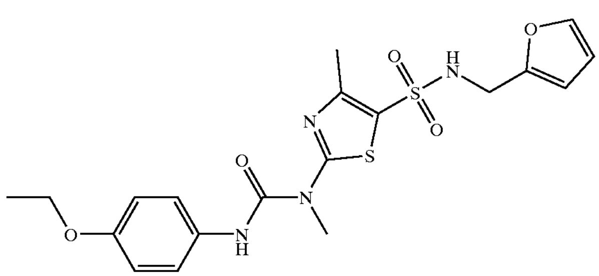 | 162 | | | | | |

-continued

| Ex. No. | Structure | m.p. [° C.] | LC/MS method | Retention time | MS (M + H) | Molecular weight | Rf |
|---|---|---|---|---|---|---|---|
| 67 | 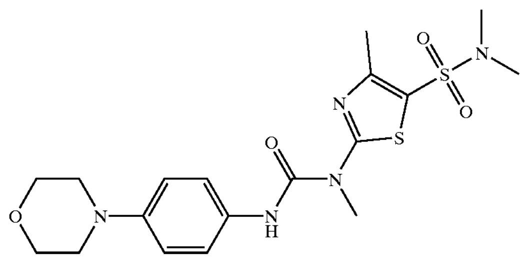 | 171 | | | | | |
| 68 | 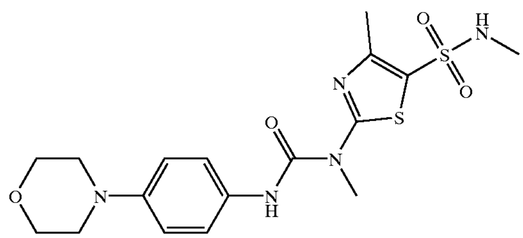 | 168 | | | | | |
| 69 | 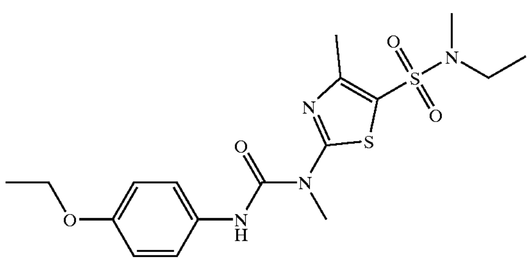 | 163 | | | | | |
| 70 | 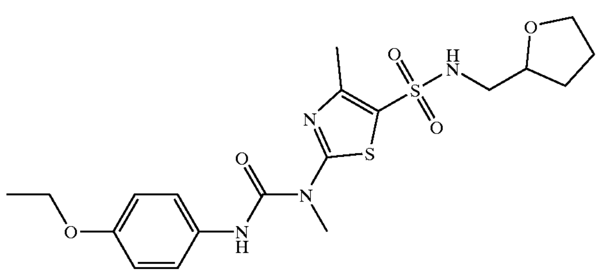 | 168 | | | | | |
| 71 | 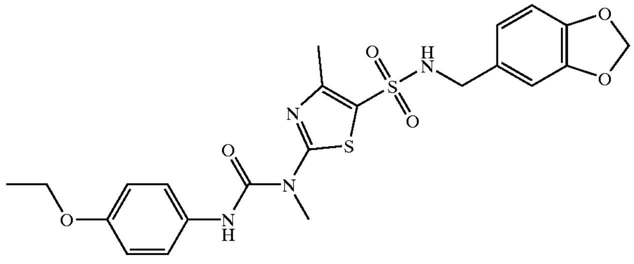 | 178 | | | | | |

| Ex. No. | Structure | m.p. [° C.] | LC/MS method | Retention time | MS (M + H) | Molecular weight | Rf |
|---|---|---|---|---|---|---|---|
| 72 | 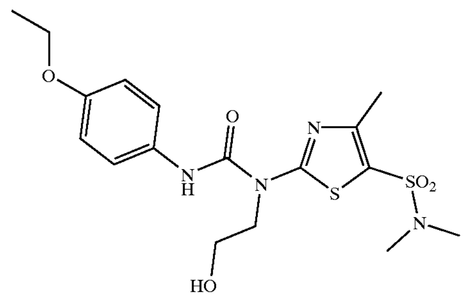 | 160 | | | | | |
| 73 | 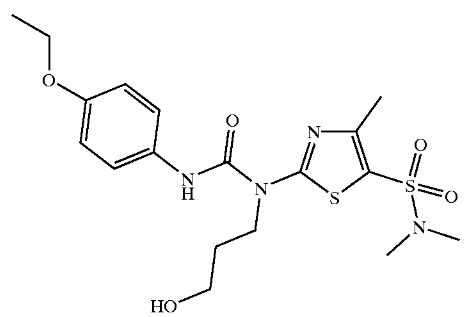 | 147 | | | | | |
| 74 | 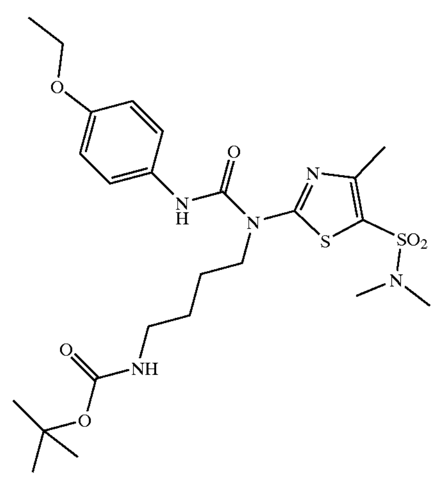 | 152 | | | | | |
| 75 | 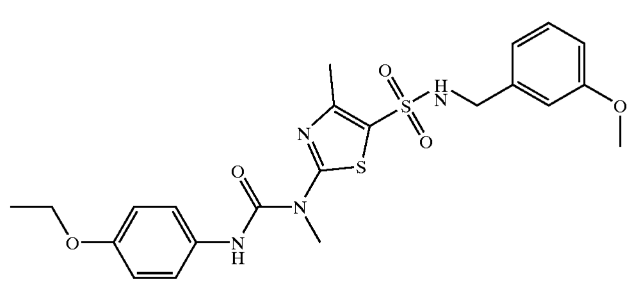 | 134 | | | | | |

-continued

| Ex. No. | Structure | m.p. [° C.] | LC/MS method | Retention time | MS (M + H) | Molecular weight | Rf |
|---|---|---|---|---|---|---|---|
| 76 | 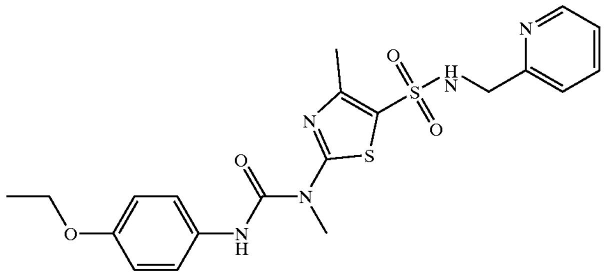 | 154 | | | | | |
| 77 | 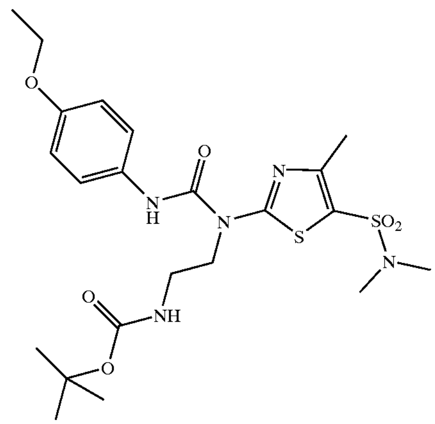 | 164 | | | | | |
| 78 | 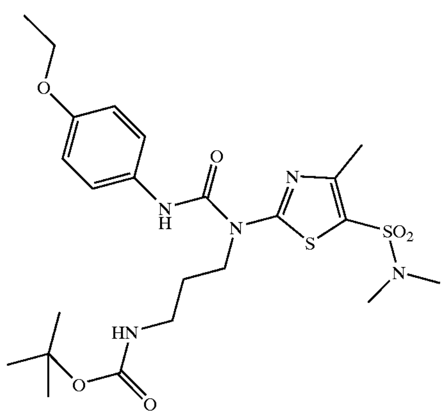 | 130 | | | | | |
| 79 | 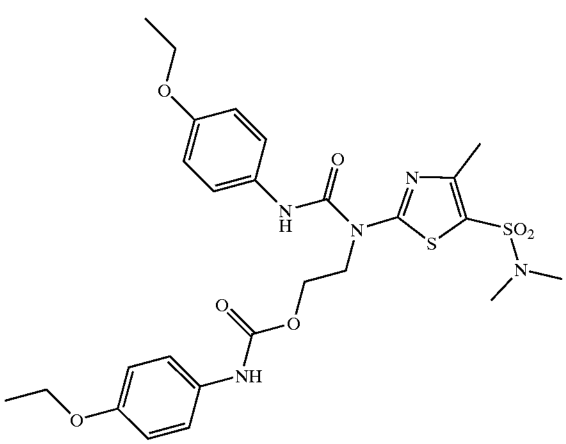 | 177 | | | | | |

-continued

| Ex. No. | Structure | m.p. [° C.] | LC/MS method | Retention time | MS (M + H) | Molecular weight | Rf |
|---|---|---|---|---|---|---|---|
| 80 | 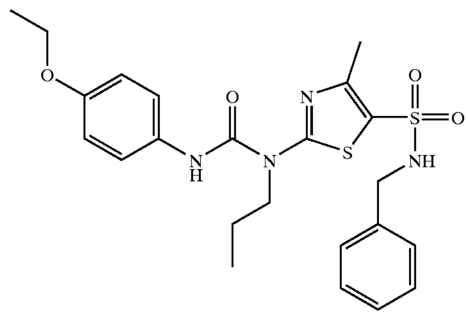 | 145 | | | | | |
| 81 | 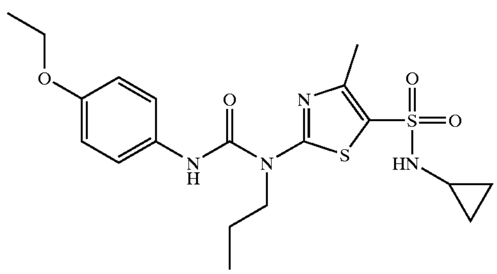 | 141 | | | | | |
| 82 | 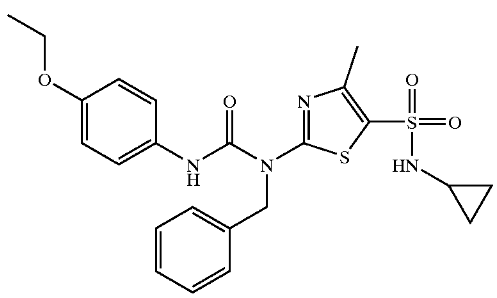 | 178 | | | | | |
| 83 | 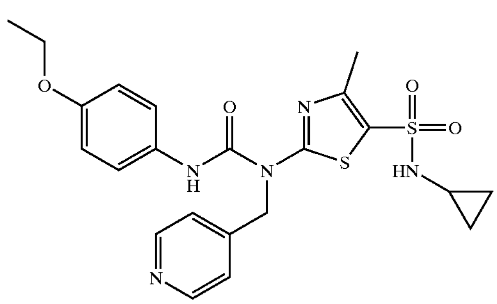 | 200 | | | | | |
| 84 | 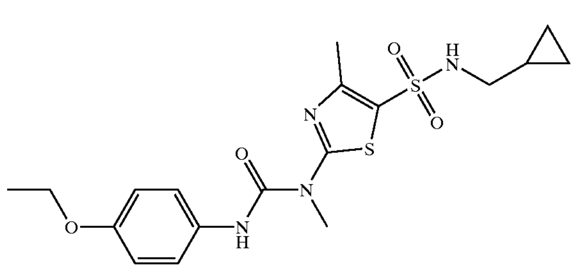 | 164 | | | | | |

-continued

| Ex. No. | Structure | m.p. [° C.] | LC/MS method | Retention time | MS (M + H) | Molecular weight | Rf |
|---|---|---|---|---|---|---|---|
| 85 | 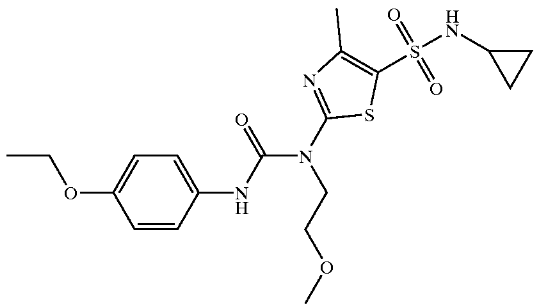 | 164 | | | | | |
| 86 | 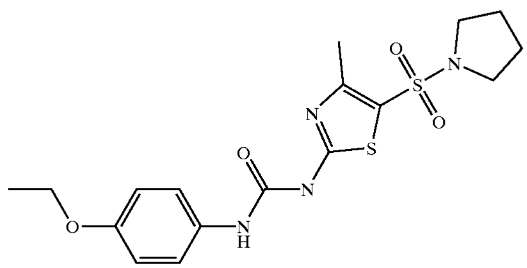 | 198 | | | | | |
| 87 | 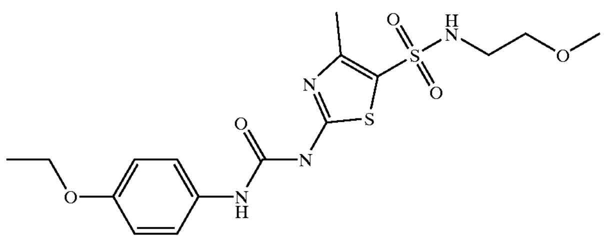 | 137 | | | | | |
| 88 | 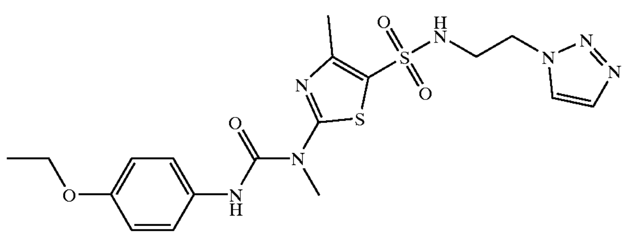 | 154 | | | | | |
| 89 | 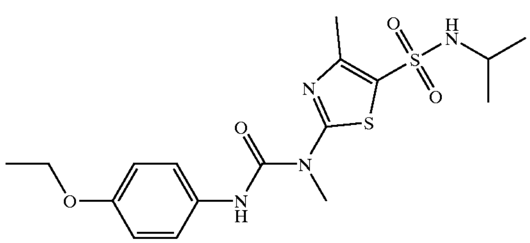 | 192 | | | | | |
| 90 | 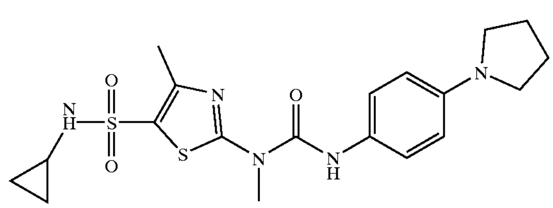 | | | | | | 0.50 (EP1) |

-continued

| Ex. No. | Structure | m.p. [° C.] | LC/MS method | Retention time | MS (M + H) | Molecular weight | Rf |
|---|---|---|---|---|---|---|---|
| 91 | 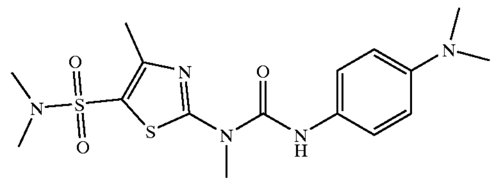 | | | | | | 0.22 (EP1) |
| 92 | 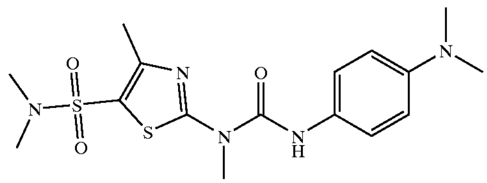 | | | | | | 0.41 (EP1) |
| 93 | 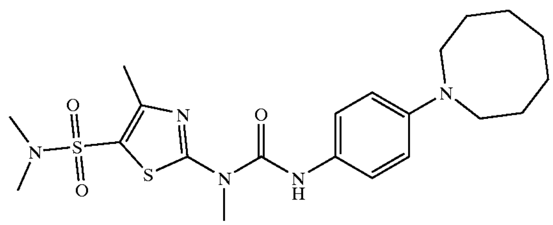 | | | | | | 0.57 (EP1) |
| 94 | 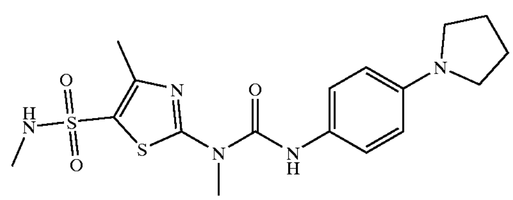 | | | | | | 0.66 (EP1) |
| 95 | 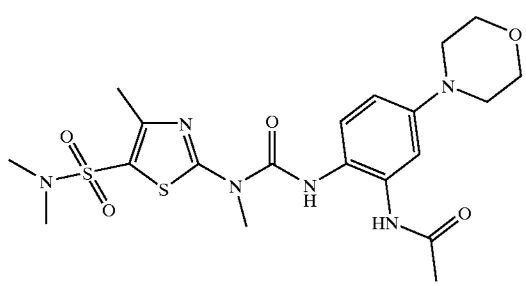 | | | | | | 0.06 (EP1) |
| 96 | 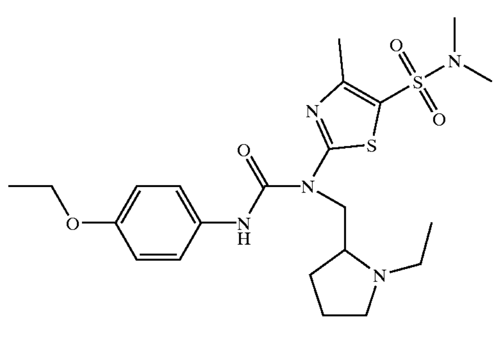 | 158 | | | | | |

-continued

| Ex. No. | Structure | m.p. [° C.] | LC/MS method | Retention time | MS (M + H) | Molecular weight | Rf |
|---|---|---|---|---|---|---|---|
| 97 | 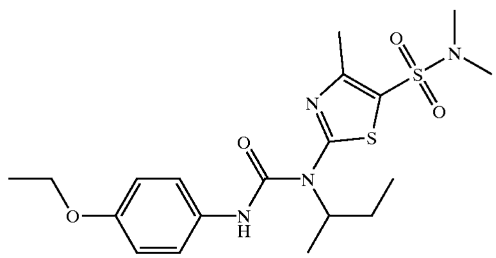 | 130 | | | | | |
| 98 | 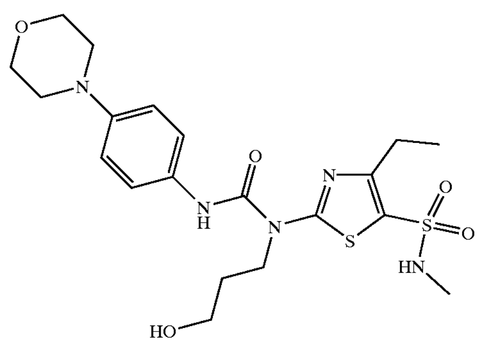 | 169 | | | | | |
| 99 | 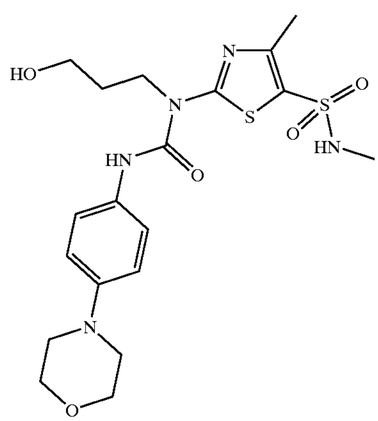 | 181 | | | | | |
| 100 | 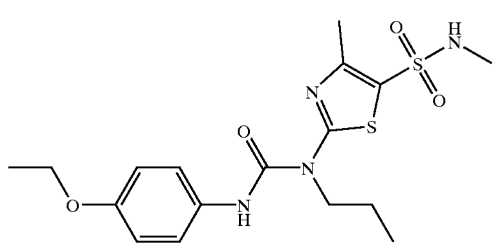 | 154 | | | | | |
| 101 | 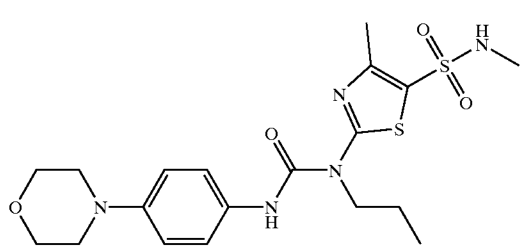 | 179 | | | | | |

-continued

| Ex. No. | Structure | m.p. [° C.] | LC/MS method | Retention time | MS (M + H) | Molecular weight | Rf |
|---|---|---|---|---|---|---|---|
| 102 | 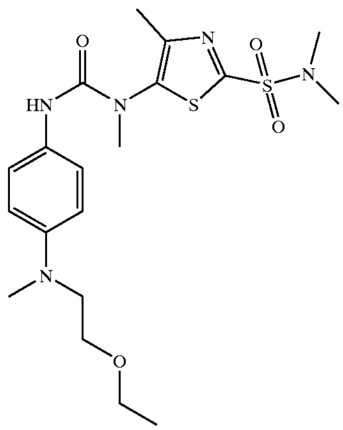 | | | | | | 0.21 (EP1) |
| 103 | 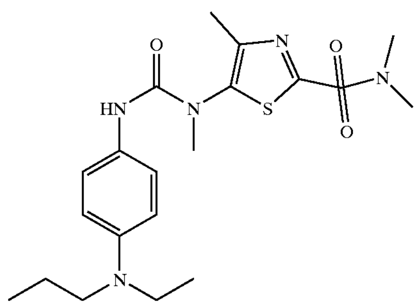 | | | | | | 0.55 (EP1) |
| 104 | 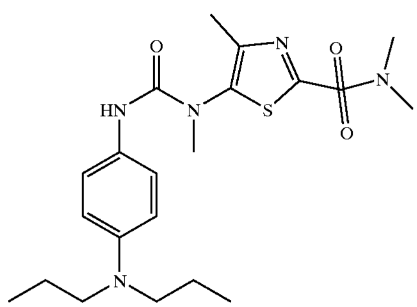 | | | | | | 0.65 (EP1) |
| 105 | 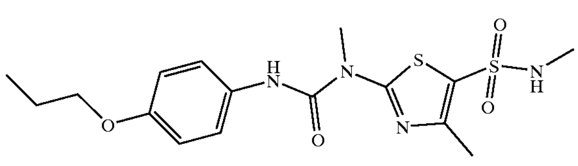 | 161 | | | | | |
| 106 | 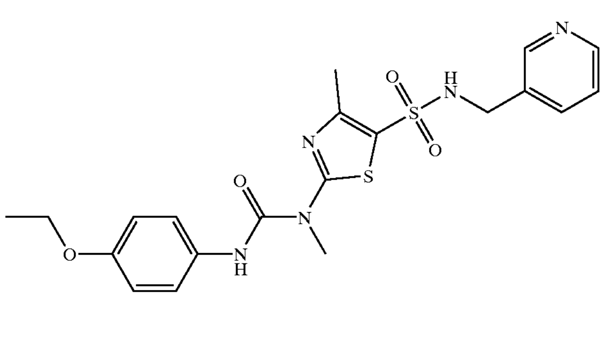 | 158 | | | | | |

-continued
| Ex. No. | Structure | m.p. [° C.] | LC/MS method | Retention time | MS (M + H) | Molecular weight | Rf |
|---|---|---|---|---|---|---|---|
| 107 | 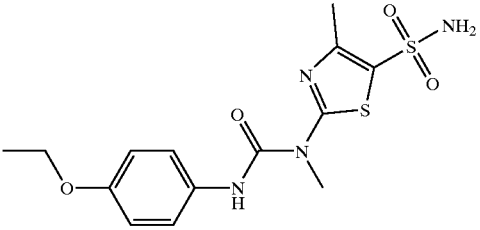 | 196 | | | | | |
| 108 | 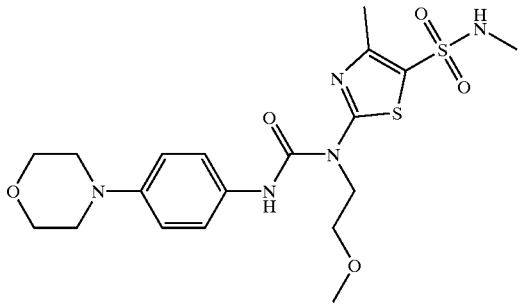 | 188 | | | | | |
| 109 | 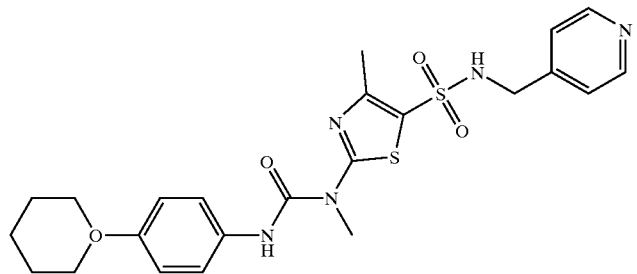 | 178 | | | | | |
| 110 | 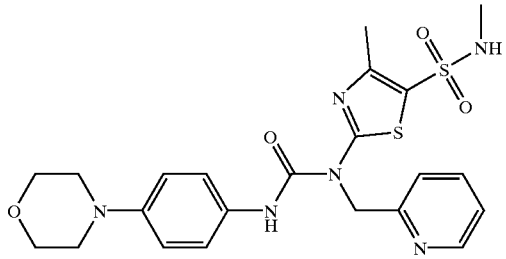 | 206 | | | | | |
| 111 | 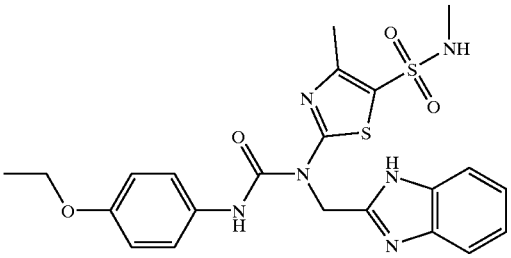 | 197 | | | | | |

-continued

| Ex. No. | Structure | m.p. [° C.] | LC/MS method | Retention time | MS (M + H) | Molecular weight | Rf |
|---|---|---|---|---|---|---|---|
| 112 | 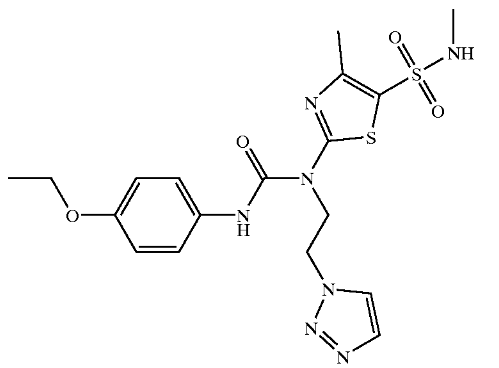 | 188 | | | | | |
| 113 | 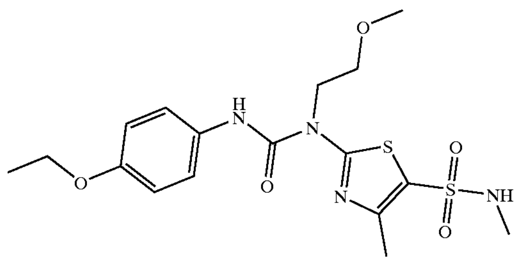 | 159 | | | | | |
| 114 | 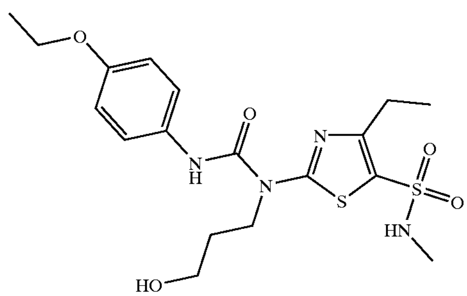 | | | | | | |
| 115 | 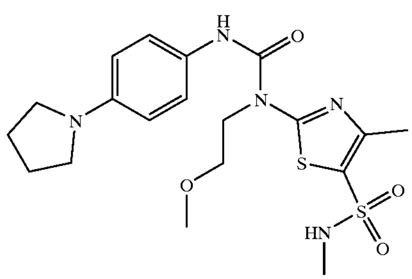 | | | | | | |
| 116 | 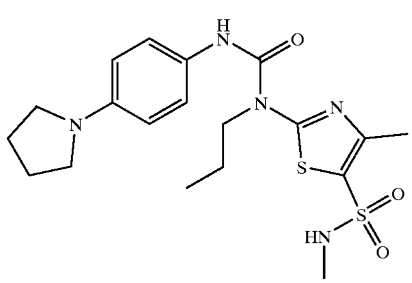 | | | | | | |

-continued
| Ex. No. | Structure | m.p. [°C.] | LC/MS method | Retention time | MS (M + H) | Molecular weight | Rf |
|---|---|---|---|---|---|---|---|
| 117 | 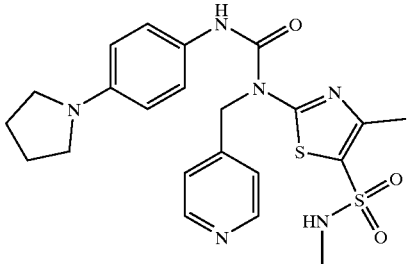 | 208 | | | | | |
| 118 | 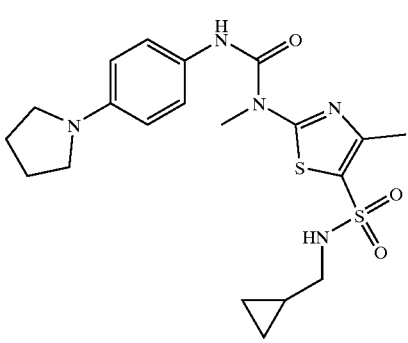 | 205 | | | | | |
| 119 | 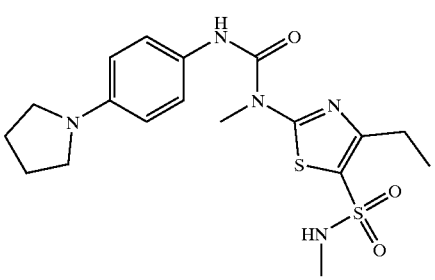 | 217 | | | | | |
| 120 | 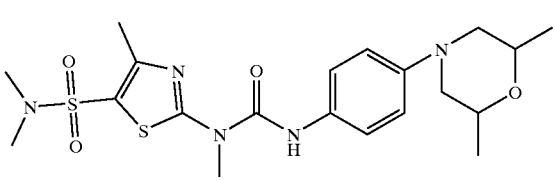 | | | | | | 0.18 (EP1) |
| 121 | 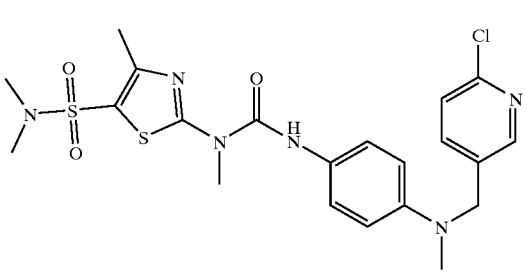 | | | | | | 0.16 (EP1) |

-continued

| Ex. No. | Structure | m.p. [° C.] | LC/MS method | Retention time | MS (M + H) | Molecular weight | Rf |
|---|---|---|---|---|---|---|---|
| 122 | 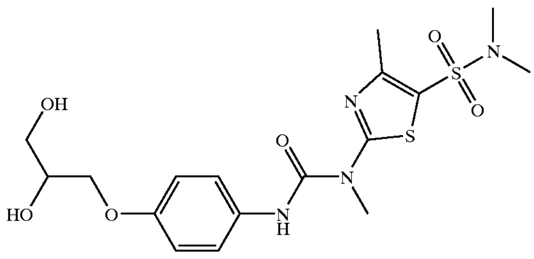 | 156 | | | | | |
| 123 | 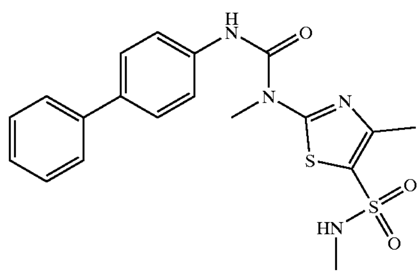 | 210 | | | | | |
| 124 | 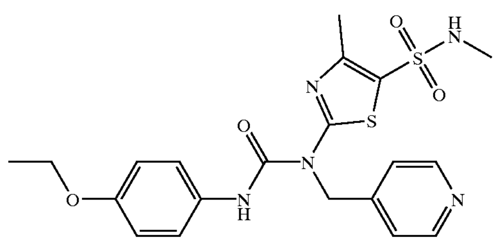 | 198 | | | | | |
| 125 | 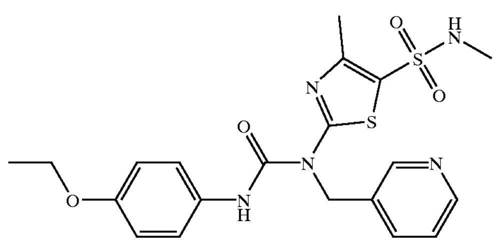 | 212 | | | | | |
| 126 | 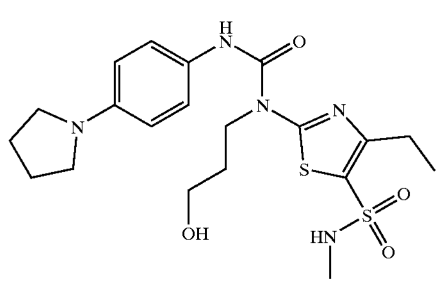 | 161 | | | | | |

| Ex. No. | Structure | m.p. [° C.] | LC/MS method | Retention time | MS (M + H) | Molecular weight | Rf |
|---|---|---|---|---|---|---|---|
| 127 | 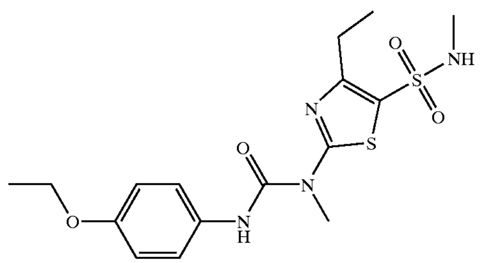 | 210 | | | | | |
| 128 | 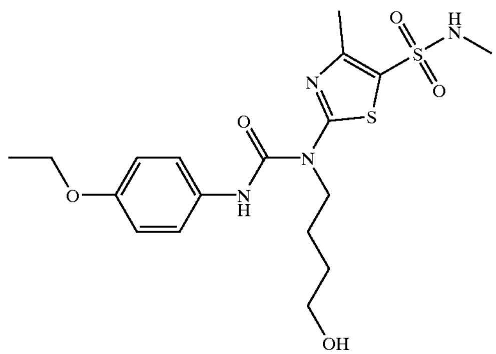 | 164 | | | | | |
| 129 | 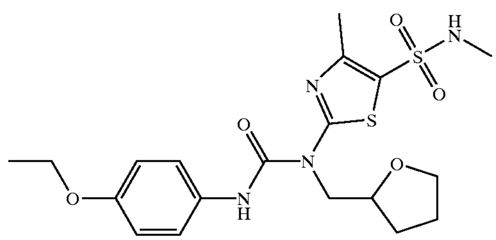 | 150 | | | | | |
| 130 | 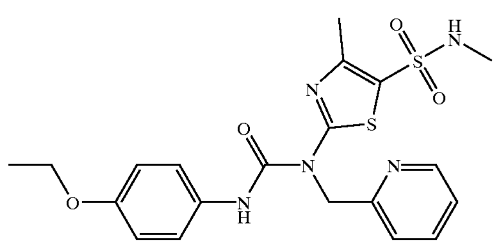 | 194 | | | | | |
| 131 | 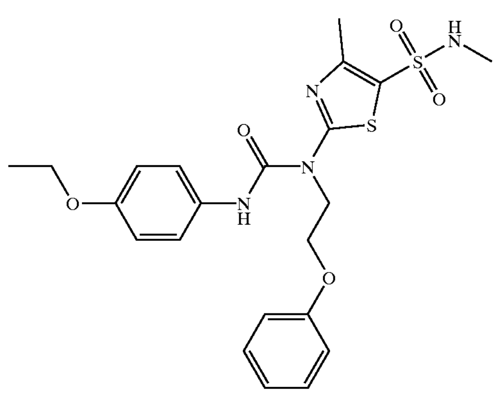 | 158 | | | | | |

-continued

| Ex. No. | Structure | m.p. [° C.] | LC/MS method | Retention time | MS (M + H) | Molecular weight | Rf |
|---|---|---|---|---|---|---|---|
| 132 | 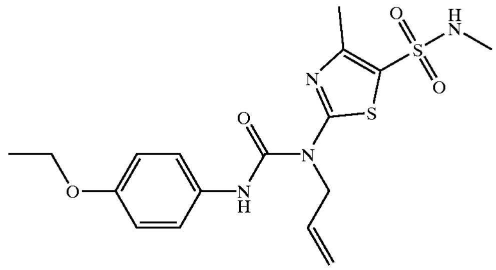 | 162 | | | | | |
| 133 | 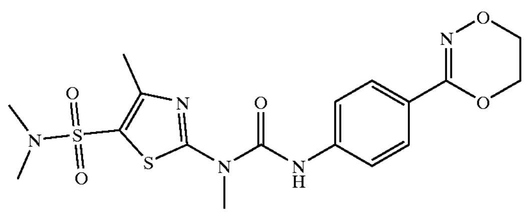 | | | | | | 0.30 (EP2) |
| 134 | 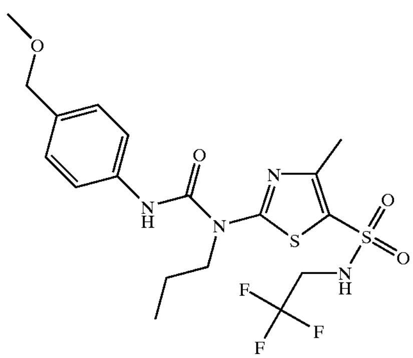 | 143 | | | | | |
| 135 | 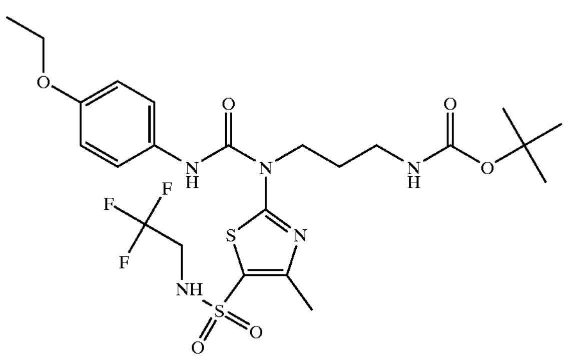 | 161 | | | | | |
| 136 | 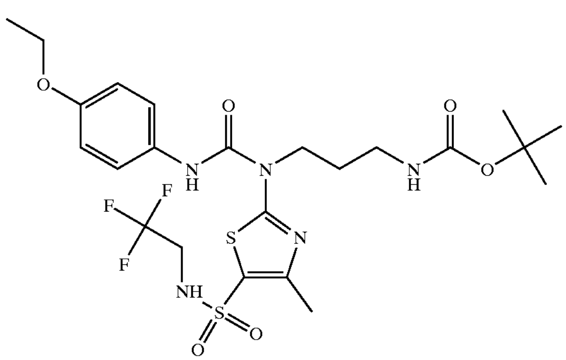 | 150 | | | | | |

| Ex. No. | Structure | m.p. [° C.] | LC/MS method | Retention time | MS (M + H) | Molecular weight | Rf |
|---|---|---|---|---|---|---|---|
| 137 | 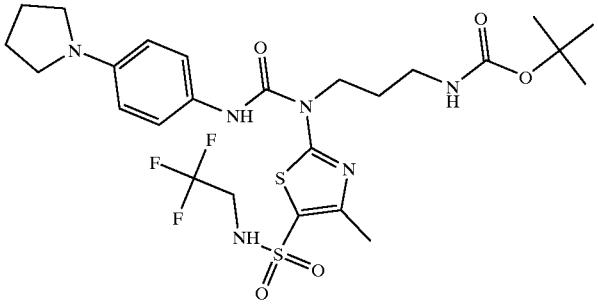 | | SMKL-N1-1 | 4.58 | 621 | 620.7 | |
| 138 | 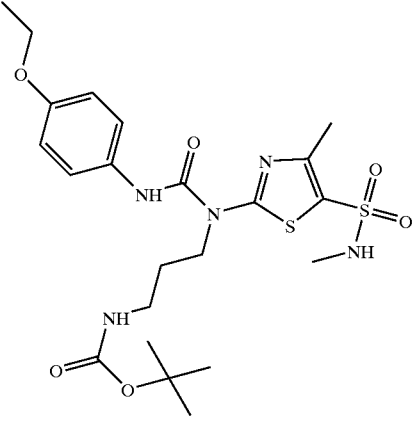 | 146 | | | | | |
| 139 | 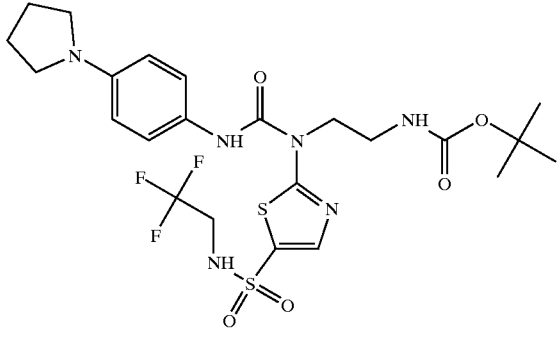 | | SMKL-N1-1 | 4.63 | 607 | 606.7 | |
| 140 | 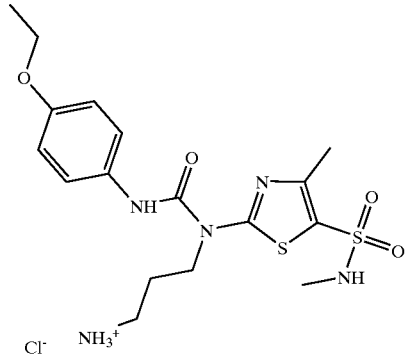 | 150 | | | | | |

| Ex. No. | Structure | m.p. [° C.] | LC/MS method | Retention time | MS (M + H) | Molecular weight | Rf |
|---|---|---|---|---|---|---|---|
| 141 | 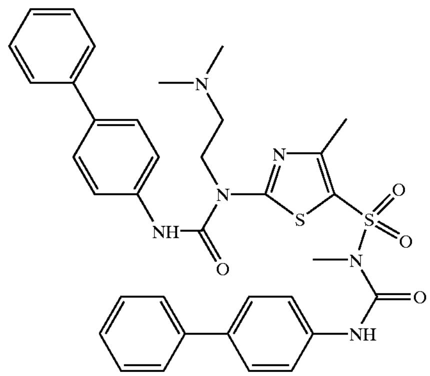 | 190 | | | | | |
| 142 | 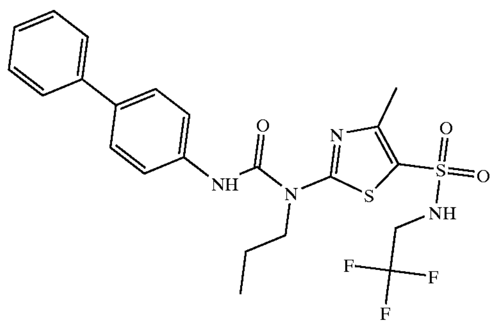 | 146 | | | | | |
| 143 | 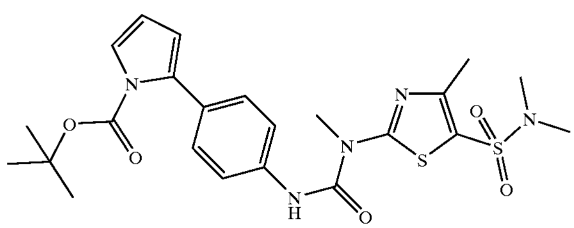 | 84 | | | | | |
| 144 | 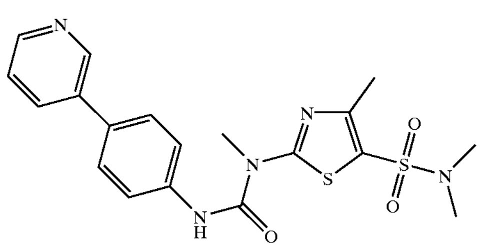 | | | | | | 0.38 (EE) |
| 145 | 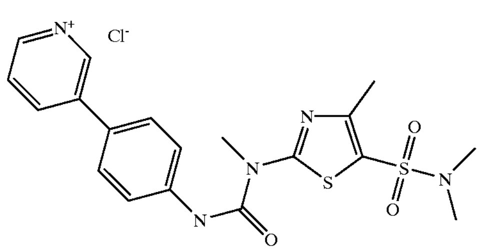 | | | | | | 0.02 (EE) |

-continued

| Ex. No. | Structure | m.p. [° C.] | LC/MS method | Retention time | MS (M + H) | Molecular weight | Rf |
|---|---|---|---|---|---|---|---|
| 146 | 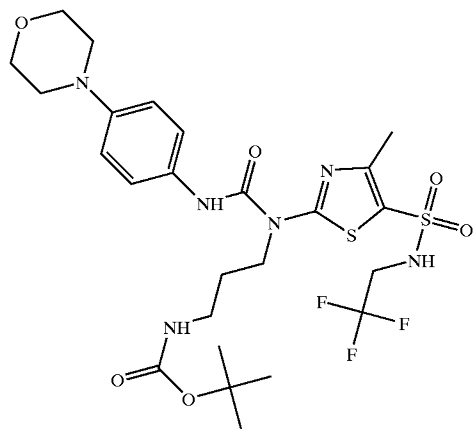 | | SMKL-N1-1 | 4.28 | 637 | 636.7 | |
| 147 | 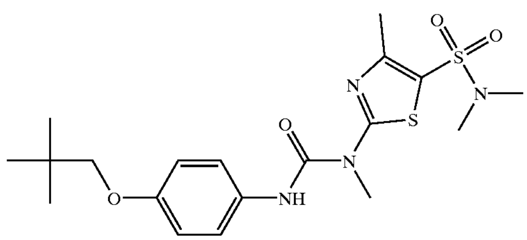 | 158 | | | | | |
| 148 | 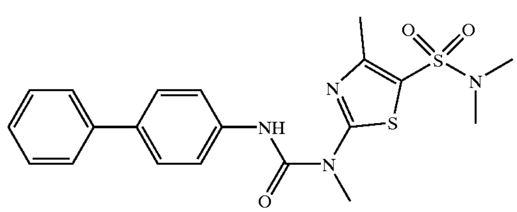 | 228 | | | | | |
| 149 | 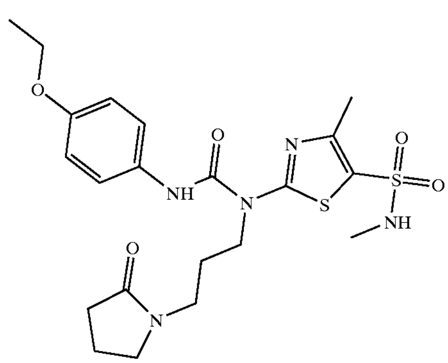 | 188 | | | | | |

| Ex. No. | Structure | m.p. [° C.] | LC/MS method | Retention time | MS (M + H) | Molecular weight | Rf |
|---|---|---|---|---|---|---|---|
| 150 | 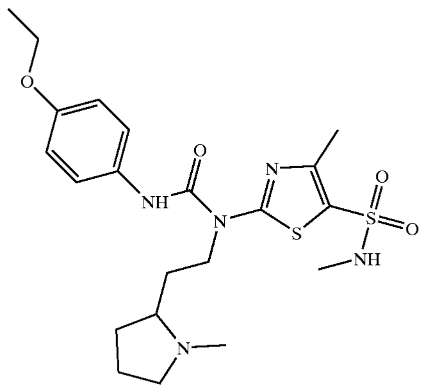 | 141 | | | | | |
| 151 | 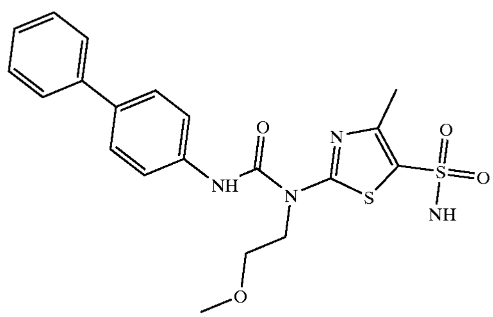 | 167 | | | | | |
| 152 | 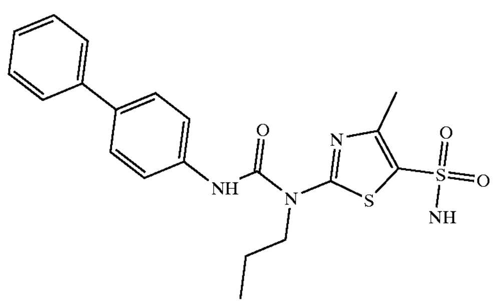 | 144 | | | | | |
| 153 | 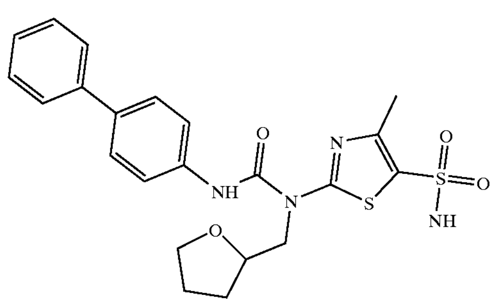 | 165 | | | | | |

| Ex. No. | Structure | m.p. [° C.] | LC/MS method | Retention time | MS (M + H) | Molecular weight | Rf |
|---|---|---|---|---|---|---|---|
| 154 | 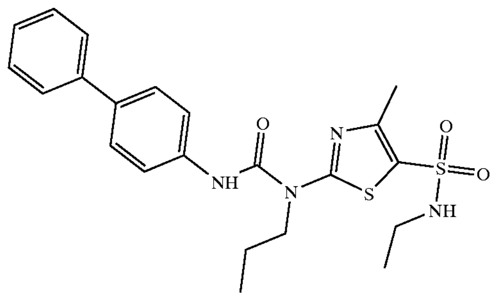 | 160 | | | | | |
| 155 | 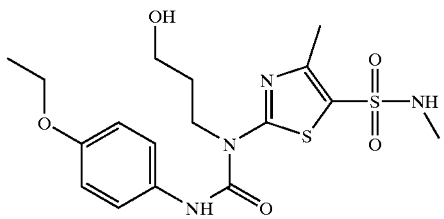 | 161 | | | | | |
| 156 | 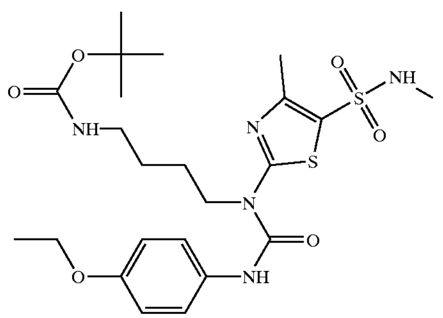 | 148 | | | | | |
| 157 | 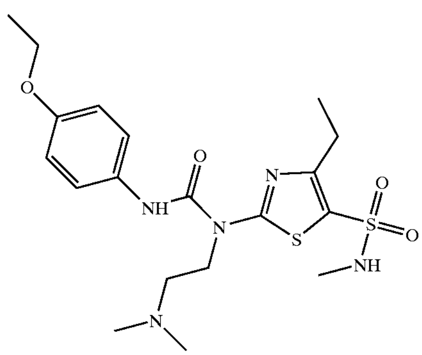 | 208 | | | | | |
| 158 | 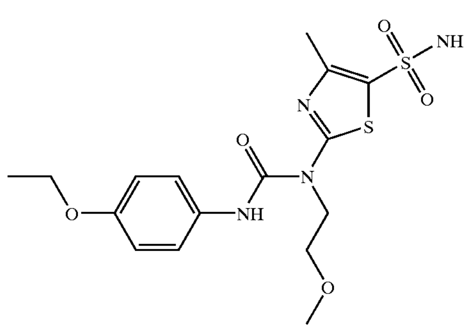 | 171 | | | | | |

-continued

| Ex. No. | Structure | m.p. [° C.] | LC/MS method | Retention time | MS (M + H) | Molecular weight | Rf |
|---|---|---|---|---|---|---|---|
| 159 | 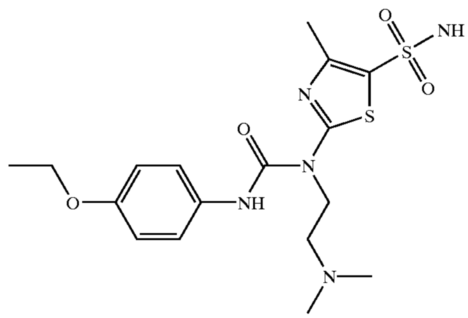 | 162 | | | | | |
| 160 | 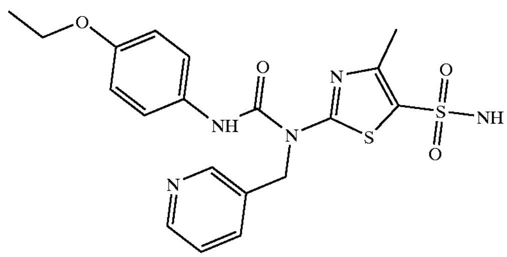 | 193 | | | | | |
| 161 | 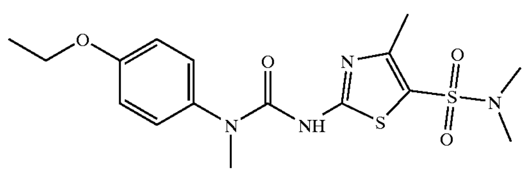 | 118 | | | | | |
| 162 | 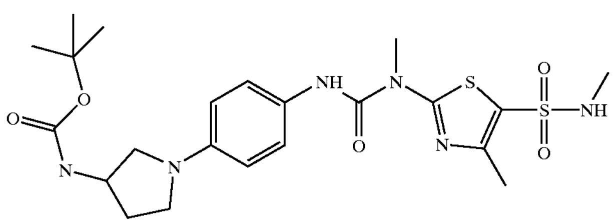 | 188–189 decomp. | | | | | |
| 163 | 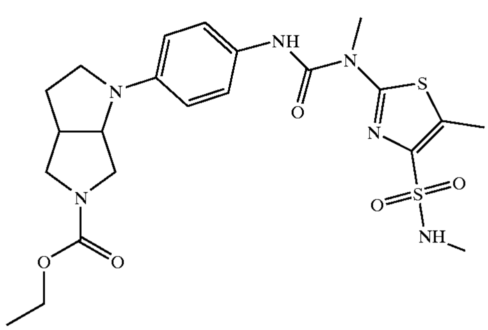 | 153–154 | | | | | |

| Ex. No. | Structure | m.p. [° C.] | LC/MS method | Retention time | MS (M + H) | Molecular weight | Rf |
|---|---|---|---|---|---|---|---|
| 164 | 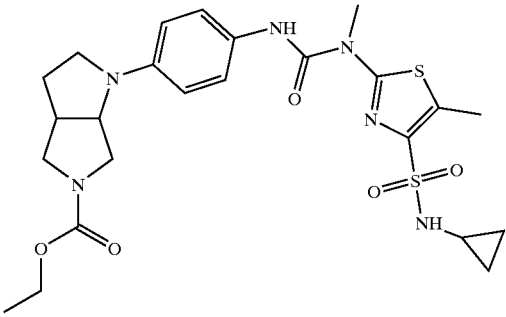 | 140 | | | | | |
| 165 | 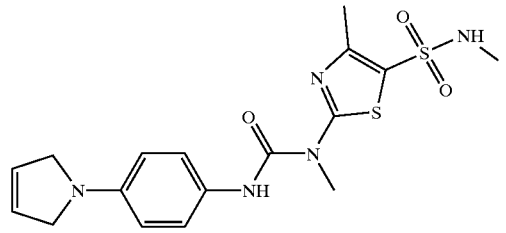 | 208–209 | | | | | |
| 166 | 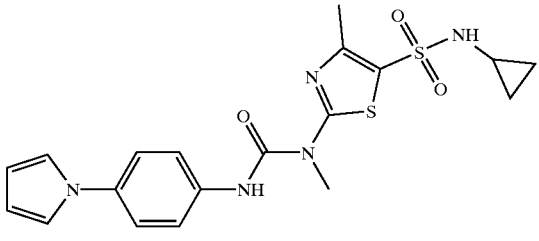 | 194 | | | | | |
| 167 | 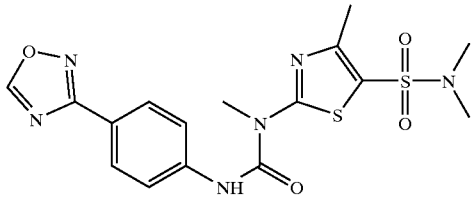 | 184–186 | | | | | |
| 168 | 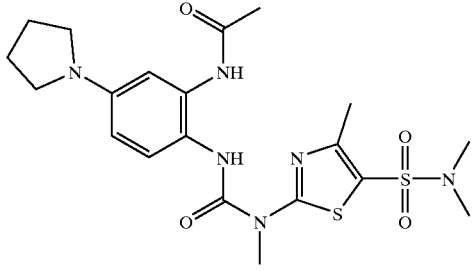 | 185–187 decomp. | | | | | |

-continued

| Ex. No. | Structure | m.p. [° C.] | LC/MS method | Retention time | MS (M + H) | Molecular weight | Rf |
|---|---|---|---|---|---|---|---|
| 169 | 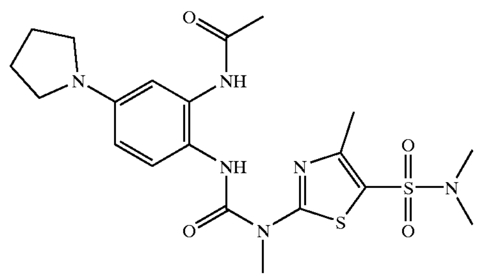 | 162–163 | | | | | |
| 170 | 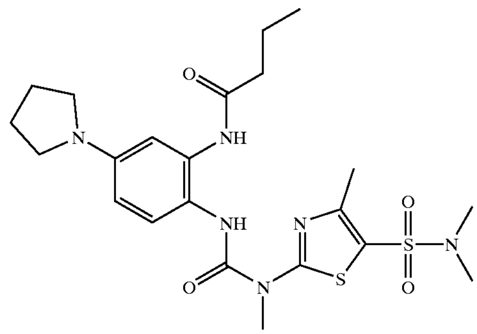 | 164 | | | | | |
| 171 | 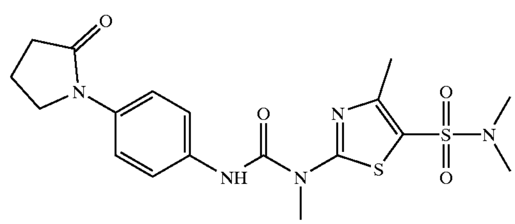 | 195 decomp. | | | | | |
| 172 | 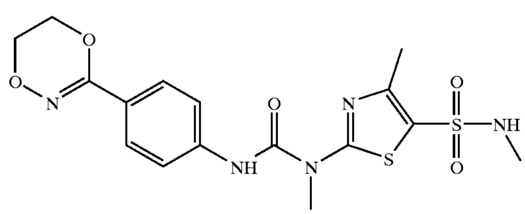 | 192–194 | | | | | |
| 173 | 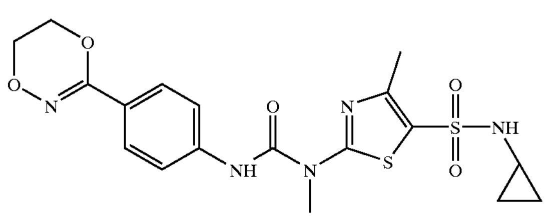 | >225 | | | | | |
| 174 | 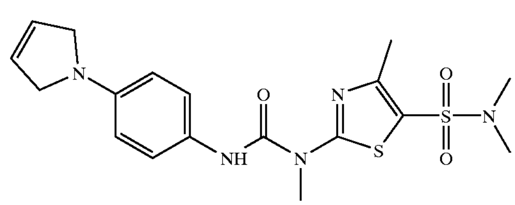 | 185 | | | | | |

-continued

| Ex. No. | Structure | m.p. [° C.] | LC/MS method | Retention time | MS (M + H) | Molecular weight | Rf |
|---|---|---|---|---|---|---|---|
| 175 | 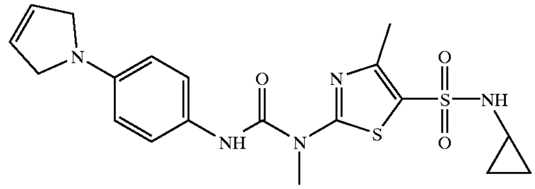 | 186–187 | | | | | |
| 176 | 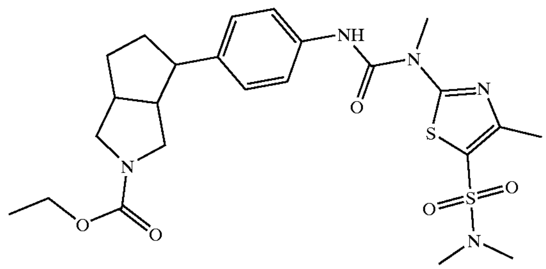 | 136–137 | | | | | |
| 177 | 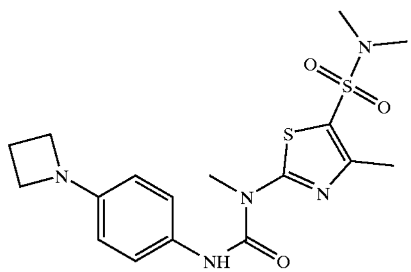 | 193–195 | | | | | |
| 178 | 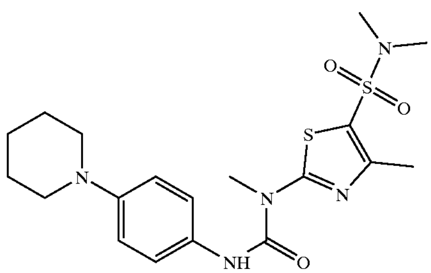 | 185 | | | | | |
| 179 | 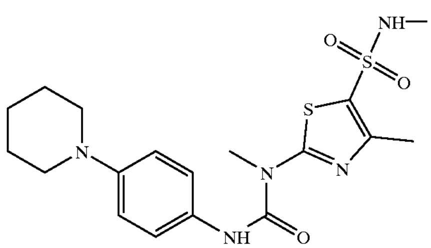 | 157–160 decomp. | | | | | |
| 180 | 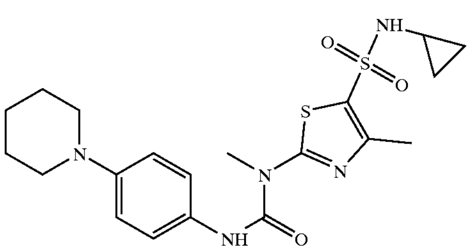 | 198 | | | | | |

-continued

| Ex. No. | Structure | m.p. [° C.] | LC/MS method | Retention time | MS (M + H) | Molecular weight | Rf |
|---|---|---|---|---|---|---|---|
| 181 | 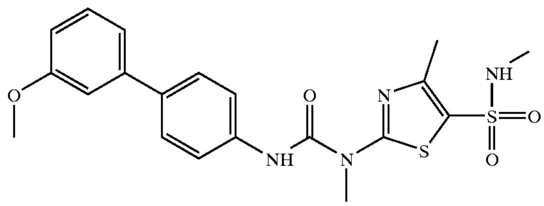 | 178 | | | | | |
| 182 | 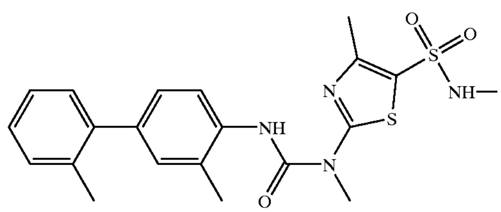 | 148 | | | | | |
| 183 | 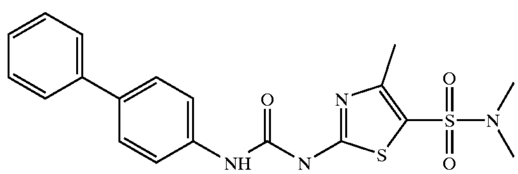 | >250 | | | | | |
| 184 | 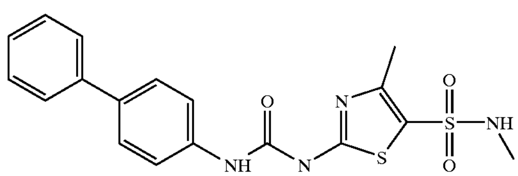 | 199 | | | | | |
| 185 | 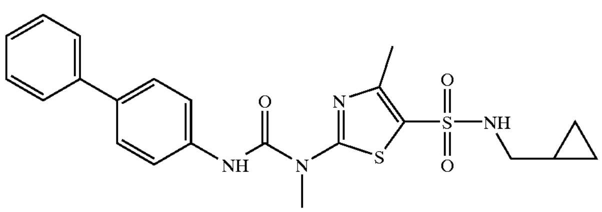 | 176 | | | | | |
| 186 | 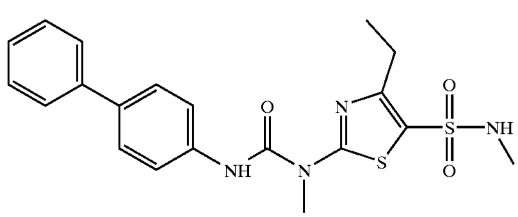 | 204 | | | | | |
| 187 | 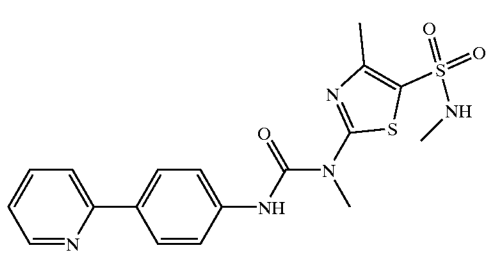 | | | | | | 0.56 (EE) |

-continued

| Ex. No. | Structure | m.p. [° C.] | LC/MS method | Retention time | MS (M + H) | Molecular weight | Rf |
|---|---|---|---|---|---|---|---|
| 188 | 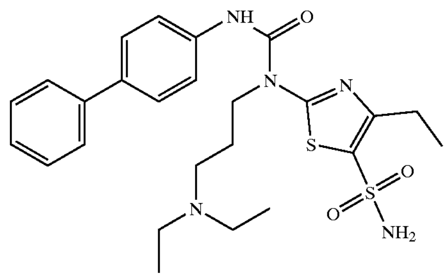 | 177 | | | | | |
| 189 | 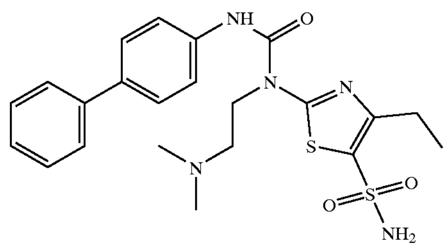 | | | | | | 0.70 (EE) |
| 190 | 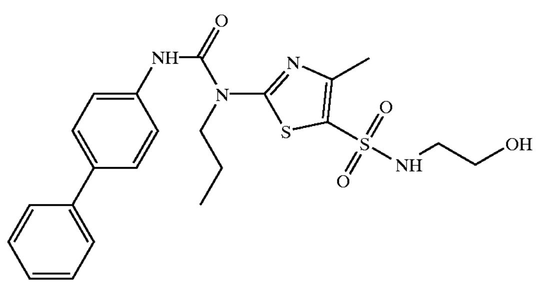 | 156 | | | | | |
| 191 | 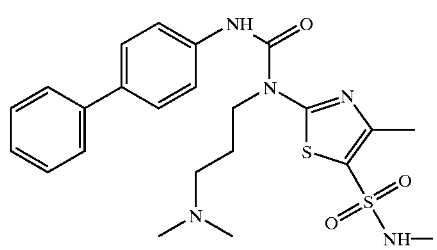 | 196 | | | | | |
| 192 | 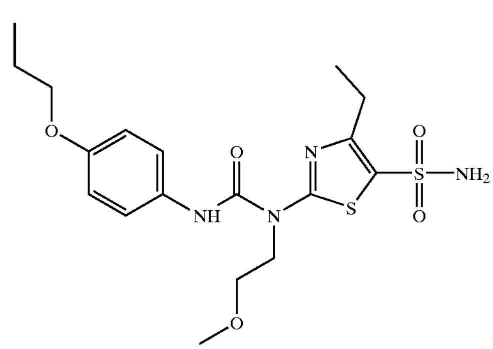 | 163 | | | | | |

| Ex. No. | Structure | m.p. [° C.] | LC/MS method | Retention time | MS (M + H) | Molecular weight | Rf |
|---|---|---|---|---|---|---|---|
| 193 | 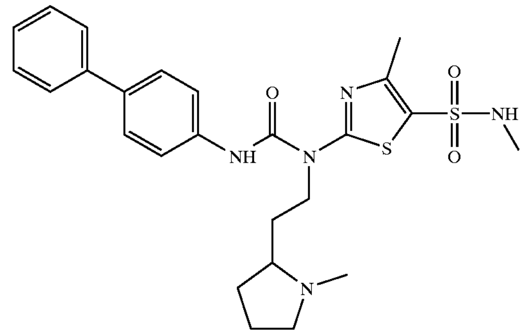 | | | | | | |
| 194 | 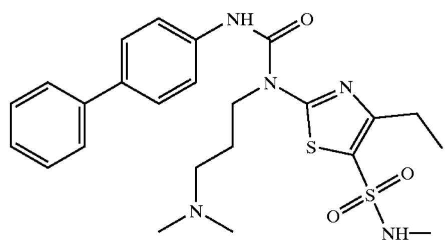 | | | | | | 0.10 (EE) |
| 195 | 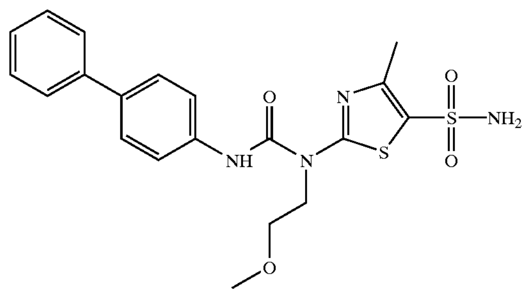 | 193 | | | | | |
| 196 | 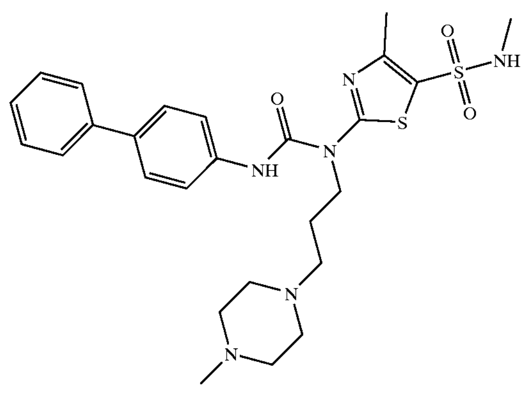 | 188 | | | | | |
| 197 | 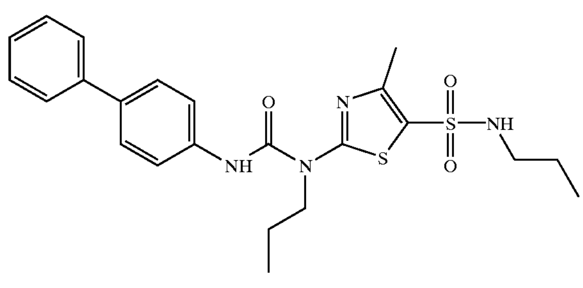 | 137 | | | | | |

-continued

| Ex. No. | Structure | m.p. [° C.] | LC/MS method | Retention time | MS (M + H) | Molecular weight | Rf |
|---|---|---|---|---|---|---|---|
| 198 | 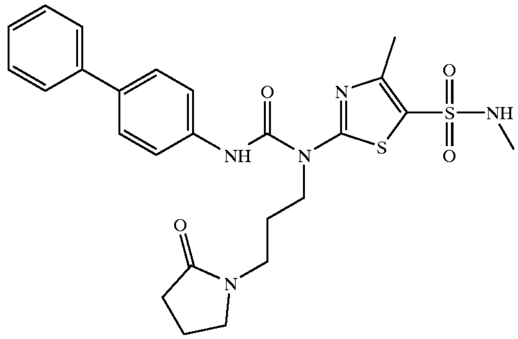 | 148 | | | | | |
| 199 | 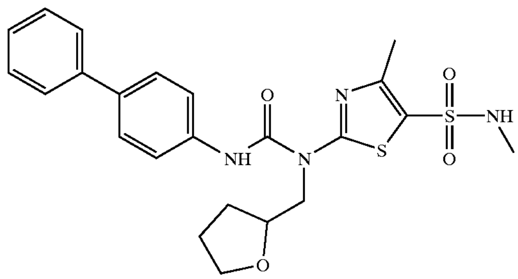 | 178 | | | | | |
| 200 | 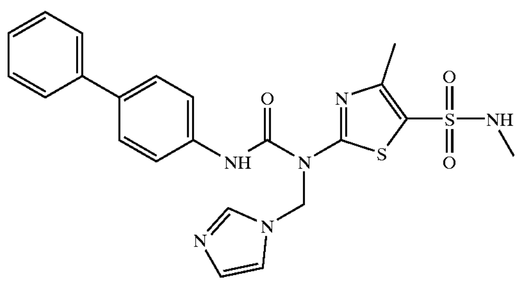 | 205 | | | | | |
| 201 | 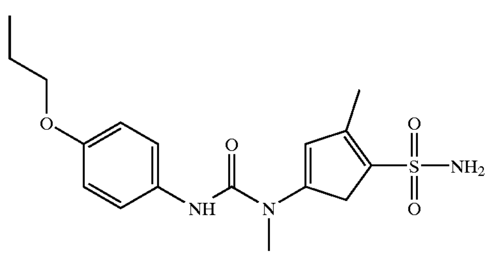 | 200 | | | | | |
| 202 | 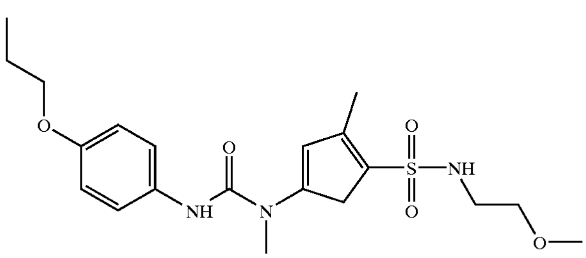 | 97 | | | | | |

| Ex. No. | Structure | m.p. [° C.] | LC/MS method | Retention time | MS (M + H) | Molecular weight | Rf |
|---|---|---|---|---|---|---|---|
| 203 | 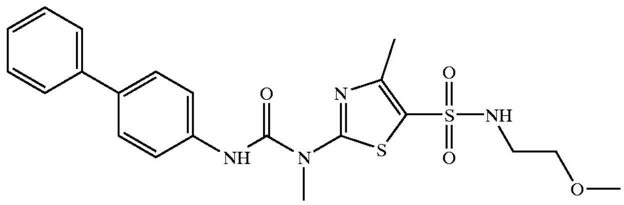 | 157 | | | | | |
| 204 | 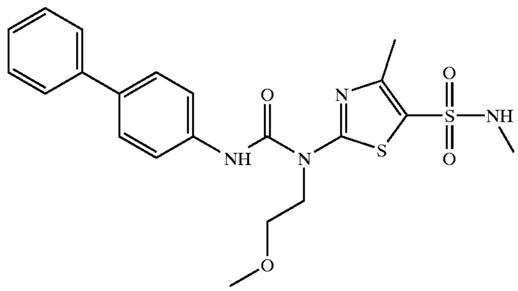 | 170 | | | | | |
| 205 | 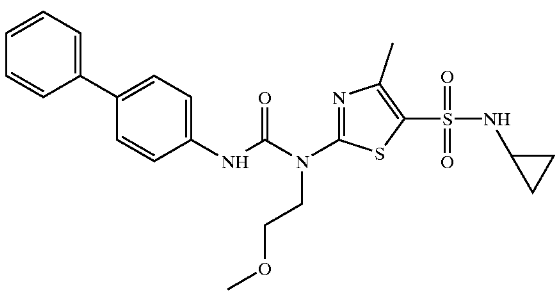 | 160 | | | | | |
| 206 | 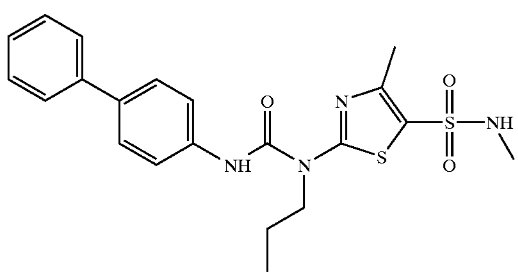 | 156 | | | | | |
| 207 | 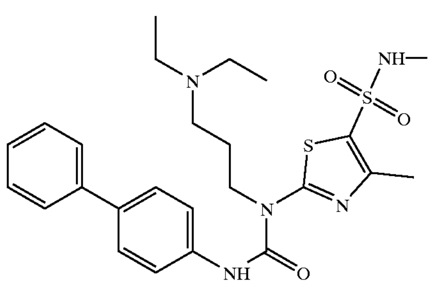 | | | | | | 0.13 (EE) |

-continued

| Ex. No. | Structure | m.p. [° C.] | LC/MS method | Retention time | MS (M + H) | Molecular weight | Rf |
|---|---|---|---|---|---|---|---|
| 208 | 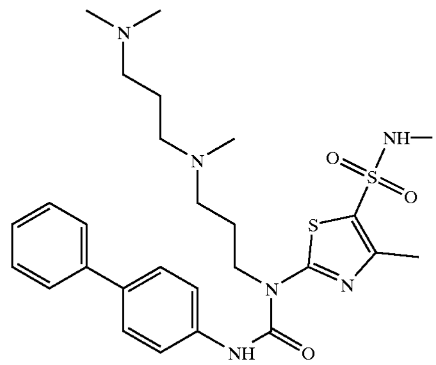 | | | | | | |
| 209 | 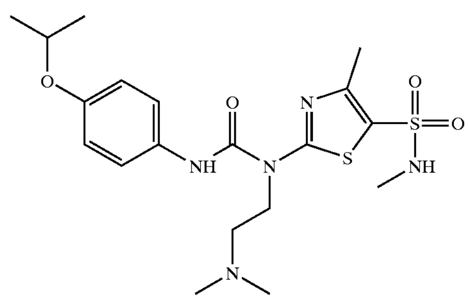 | | | | | | 0.38 (EE) |
| 210 | 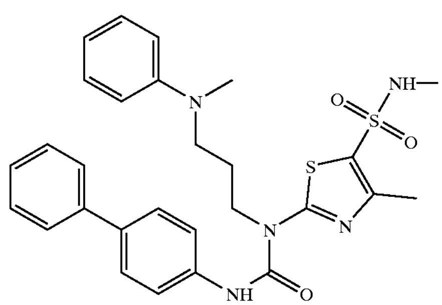 | 148 | | | | | |
| 211 | 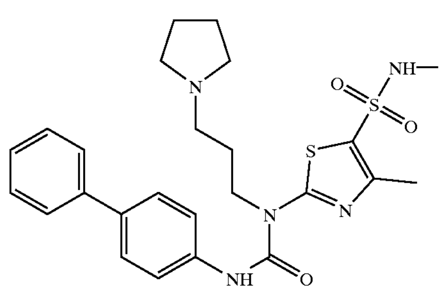 | | | | | | 0.06 (EE) |

-continued

| Ex. No. | Structure | m.p. [° C.] | LC/MS method | Retention time | MS (M + H) | Molecular weight | Rf |
|---|---|---|---|---|---|---|---|
| 212 | 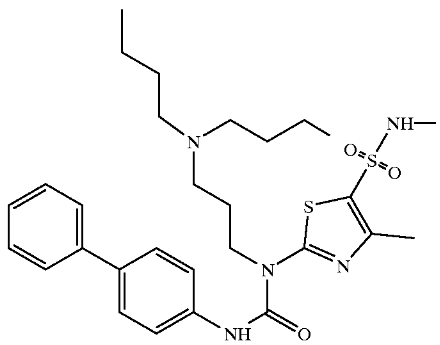 | | | | | | 0.31 (EE) |
| 213 | 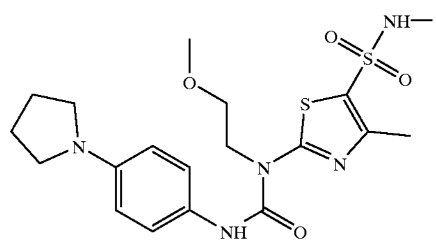 | 184 | | | | | |
| 214 | 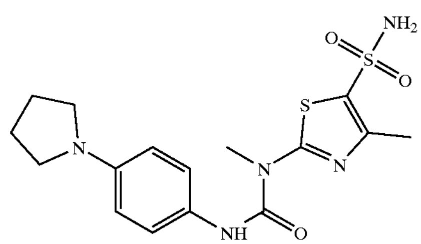 | 209 | | | | | |
| 215 | 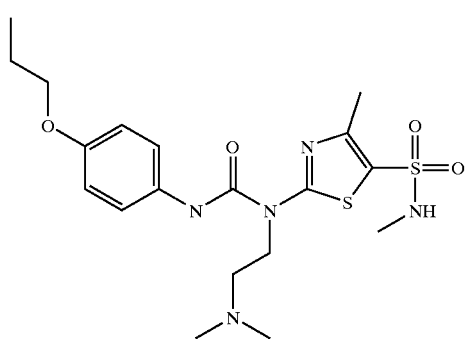 | 165 | | | | | |
| 216 | 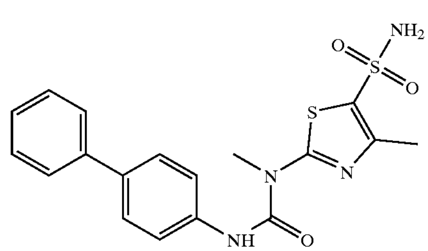 | 221 | | | | | |

-continued
| Ex. No. | Structure | m.p. [° C.] | LC/MS method | Retention time | MS (M + H) | Molecular weight | Rf |
|---|---|---|---|---|---|---|---|
| 217 | 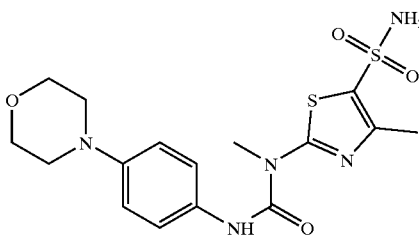 | 225 | | | | | |
| 218 | 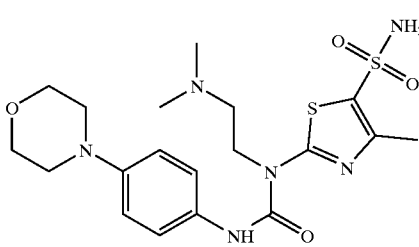 | 123 | | | | | |
| 219 | 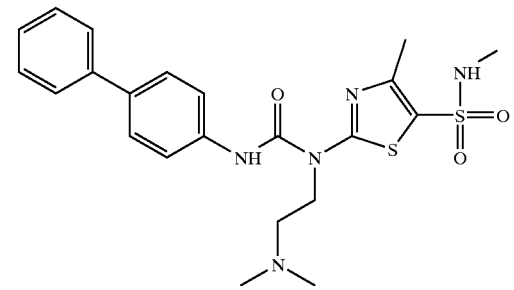 | 154 | | | | | |
| 220 | 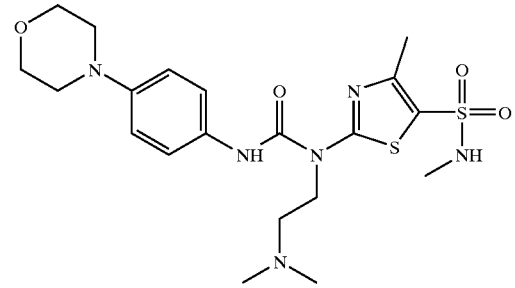 | 196 | | | | | |
| 221 | 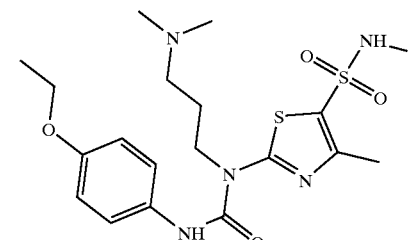 | 185 | | | | | |

-continued

| Ex. No. | Structure | m.p. [° C.] | LC/MS method | Retention time | MS (M + H) | Molecular weight | Rf |
|---|---|---|---|---|---|---|---|
| 222 | 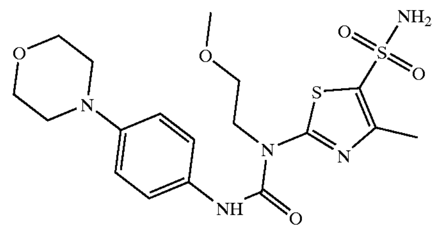 | 201 | | | | | |
| 223 | 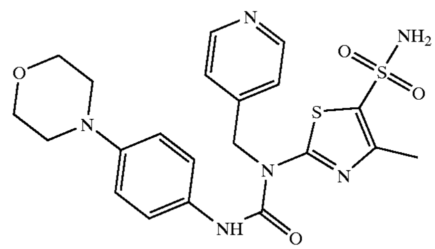 | 186 | | | | | |
| 224 | 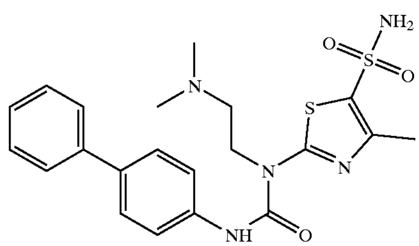 | 138 | | | | | |
| 225 | 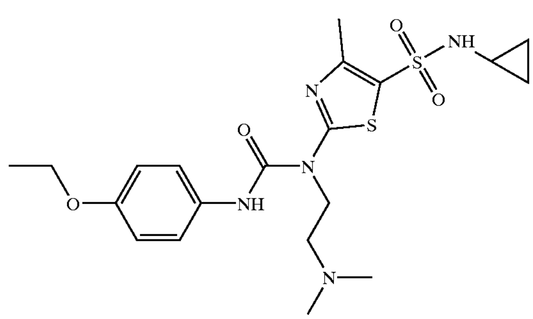 | 168 | | | | | |
| 226 | 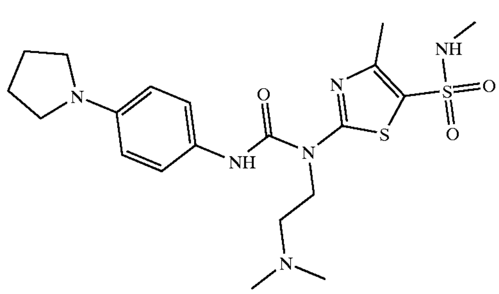 | 188 | | | | | |

-continued

| Ex. No. | Structure | m.p. [° C.] | LC/MS method | Retention time | MS (M + H) | Molecular weight | Rf |
|---|---|---|---|---|---|---|---|
| 227 | 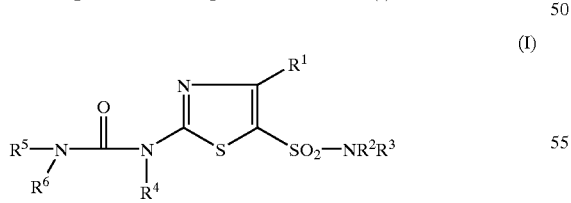 | | | | | | 0.75 (EE) |

In the above table, the Rf means the retention index in the thin-layer chromatography on silica gel with the following mobile phases:
EE: ethyl acetate
EP1: ethyl acetate/petroleum ether (ratio 1:1 by volume),
EP2: ethyl acetate/petroleum ether (ratio 2:1 by volume), SMKL-N1-1 refers to the following LC-MS method:
Method: SMKL-N1-1 Low Vol HCl

| MS apparatus type: | Finnigan MAT 900S | |
|---|---|---|
| | Ionization: | ESI positive |
| HPLC apparatus type: | TSP: P4000,AS3000,UV3000HR | |
| Pump head: | low volume | |
| Column: | Symmetry C 18 | |
| | 150 mm × 2.1 mm 5 μm | |
| Supplier: | Waters | |

| UV-Detector DAD: | 210 nm | | | | |
|---|---|---|---|---|---|
| Oven temp.: | 40° C. | | | | |
| Gradient: Time | A:% | B:% | C:% | D:% | Flow |
| 0 | 10.0 | 45 | 45 | — | 0.6 |
| 4 | 90 | 5 | 5 | — | 0.6 |
| 9 | 90 | 5 | 5 | — | 0.6 |
| 9.5 | 10.0 | 45 | 45 | — | 0.8 |
| 11.5 | 10.0 | 45 | 45 | — | 0.8 |
| 12 | 10.0 | 45 | 45 | — | 0.6 |
| A: | $CH_3CN$ | | | | |
| B: | HCl 0.01N | | | | |
| C: | $H_2O$ | | | | |
| D: | — | | | | |

What is claimed is:

1. A compound of the general formula (I),

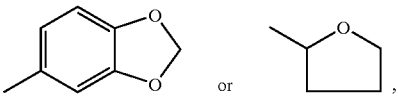

in which
R$^1$ represents hydrogen, halogen, ($C_1$–$C_6$)-alkyl, ($C_1$–$C_6$)-alkoxy, amino($C_1$–$C_6$)alkyl or halogeno($C_1$–$C_6$)alkyl,
R$^2$ and R$^3$ are identical or different and represent hydrogen, ($C_3$–$C_8$)-cycloalkyl or biphenylylaminocarbonyl, or
represent ($C_1$–$C_6$)-alkyl which is optionally substituted by 1 to 3 substituents selected from the group consisting of ($C_3$–$C_6$)-cycloalkyl, ($C_1$–$C_6$)-alkoxy, halogen, hydroxyl, radicals of the formula a 5- to 6-membered aromatic heterocycle with up to 3 heteroatoms from the series S, N and/or O, it also being possible for a nitrogen-containing heterocycle to be bonded via the nitrogen atom,
a 3- to 8-membered saturated or unsaturated, nonaromatic heterocycle which has up to 3 heteroatoms from the series S, N and/or O and is optionally bonded via a nitrogen atom, and ($C_6$–$C_{10}$)-aryl which in turn may be substituted by hydroxyl or ($C_1$–$C_6$)-alkoxy, or
R$^2$ and R$^3$ form, together with the nitrogen atom, a 5- to 6-membered saturated heterocycle which optionally also has an oxygen atom,
R$^4$ represents hydrogen, ($C_1$–$C_6$)-acyl, ($C_2$–$C_6$)-alkenyl, or
R$^4$ represents ($C_1$–$C_6$)-alkyl which is optionally substituted by 1 to 3 substituents selected from the group consisting of halogen, hydroxyl, ($C_1$–$C_6$)-acyl, ($C_1$–$C_6$)-alkoxy, phenoxy, ($C_6$–$C_{10}$)-aryl and —NR$^7$R$^8$,
in which R$^7$ and R$^8$ are identical or different and denote hydrogen, ($C_1$–$C_6$)-acyl, ($C_1$–$C_6$)-alkyl, carbamoyl, mono- or di($C_1$–$C_6$)-alkylamino($C_1$–$C_6$)alkyl, mono- or di($C_1$–$C_6$)-alkylaminocarbonyl, ($C_6$–$C_{10}$)-aryl or ($C_1$–$C_6$)-alkoxycarbonyl, or
R$^7$ and R$^8$ form, together with the nitrogen atom, a 5- to 6-membered saturated heterocycle which optionally contains another heteroatom from the series S or O or a radical of the formula —NR$^9$ and may be substituted by oxo,
in which R$^9$ denotes hydrogen or ($C_1$–$C_4$)-alkyl, or
R$^4$ represents ($C_1$–$C_6$)-alkyl which is substituted by a 5- to 6-membered aromatic, optionally benzo-fused heterocycle with up to 3 heteroatoms from the series S, N and/or O, it also being possible for a nitrogen-containing heterocycle to be bonded via the nitrogen atom, or is substituted by radicals of the formulae

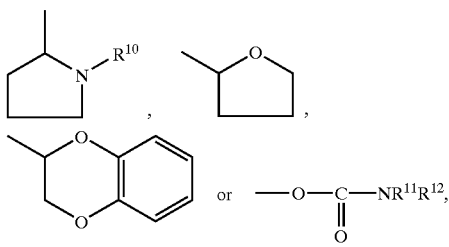

in which
R¹⁰ denotes hydrogen or $(C_1-C_6)$-alkyl,
R¹¹ and R¹² are identical or different and denote hydrogen, $(C_1-C_6)$-alkyl or $(C_6-C_{10})$-aryl, said $(C_1-C_6)$-alkyl and $(C_6-C_{10})$-aryl optionally substituted by 1 to 3 substituents selected from the group consisting of hydroxyl, $(C_1-C_6)$-alkoxy and halogen, R⁵ represents hydrogen or $(C_1-C_6)$-alkyl, R⁶ represents a radical of the formula

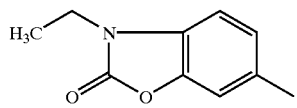

or

R⁶ represents phenyl which is optionally substituted by one to three substituents selected from the group consisting of
halogen, $(C_6-C_{10})$-aryl which is optionally substituted by 1 to 3 substituents selected from $(C_1-C_6)$ alkanoyl, $(C_1-C_6)$-alkoxy, $(C_1-C_6)$-alkyl, halogen, $(C_1-C_6)$alkoxycarbonyl, nitro, halogeno$(C_1-C_6)$ alkyl, halogeno$(C_1-C_6)$alkoxy, amino, $(C_1-C_6)$ alkylthio, hydroxyl, carboxyl, carbamoyl, mono- or di$(C_1-C_6)$alkylaminocarbonyl, mono- or di$(C_1-C_6)$ acylamino, $(C_1-C_6)$alkylsulphinyl, $(C_1-C_6)$ alkylsulphonyl, and/or cyano, or $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy with up to 6 fluorine atoms,
radicals of the formulae

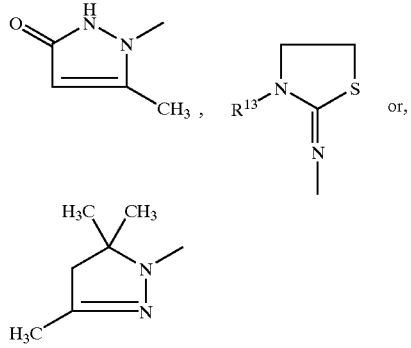

in which R¹³ denotes hydrogen or $(C_1-C_6)$-alkyl, $(C_1-C_6)$-alkyl which is optionally substituted by a radical of the formula a 5- to 6-membered aromatic heterocycle which has up to 3 heteroatoms from the series S, N and/or O, is optionally bonded via a nitrogen atom and is optionally substituted by 1 to 3 substituents selected from $(C_1-C_6)$alkanoyl, $(C_1-C_6)$-alkoxy, $(C_1-C_6)$-alkyl, halogen, $(C_1-C_6)$alkoxycarbonyl, nitro, halogeno $(C_1-C_6)$alkyl, halogeno$(C_1-C_6)$alkoxy, amino, $(C_1-C_6)$alkylthio, hydroxyl, carboxyl, carbamoyl, mono- or di$(C_1-C_6)$alkylaminocarbonyl, mono- or di$(C_1-C_6)$acylamino, $(C_1-C_6)$alkylsulphinyl, $(C_1-C_6)$alkylsulphonyl, and cyano, a 3- to 8-membered saturated or unsaturated, nonaromatic mono- or bicyclic heterocycle which has up to 3 heteroatoms from the series S, N and/or O, is optionally bonded via a nitrogen atom and is optionally substituted by 1 to 3 substituents selected from oxo, halogen, hydroxyl, $(C_1-C_6)$-alkoxycarbonyl, $(C_1-C_6)$alkoxycarbonylamino, $(C_1-C_6)$-alkyl, halogeno$(C_1-C_6)$-alkyl and hydroxy$(C_1-C_6)$-alkyl, and groups of the formulae —OR¹⁴, —NR¹⁵R¹⁶ or —CO—NR¹⁷R¹⁸,
in which
R¹⁴ denotes a radical of the formula ![structure]

or denotes phenyl which in turn is optionally substituted by a group of the formula —NR¹⁹R²⁰,
in which
R¹⁹ and R²⁰ are identical or different and denote hydrogen, $(C_1-C_6)$-alkyl or $(C_1-C_6)$-acyl, or
R¹⁴ denotes $(C_1-C_6)$-alkyl which is optionally substituted once to three times by hydroxyl,
R¹⁵ and R¹⁶ are identical or different and denote hydrogen, carbamoyl, mono- or di$(C_1-C_6)$ alkylaminocarbonyl, phenyl, $(C_1-C_6)$-acyl or $(C_1-C_6)$-alkyl,
where $(C_1-C_6)$-alkyl is optionally substituted by $(C_1-C_6)$-alkoxy, $(C_1-C_6)$-acyl, by phenyl or by a 5- to 6-membered aromatic heterocycle with up to 3 heteroatoms from the series S, N and/or O,
where aforementioned phenyl and aforementioned aromatic heterocycle are optionally substituted once to three times, identically or differently, by halogen and/or hydroxyl, and
R¹⁷ and R¹⁸ are identical or different and denote hydrogen or $(C_1-C_6)$-alkyl,
and the salts thereof.

2. A compound of the general formula (I) according to claim 1, in which
R⁶ represents phenyl which is optionally substituted by one to three substituents selected from the group consisting of halogen, $(C_6-C_{10})$-aryl which is optionally substituted by 1 to 3 substituents selected from $(C_1-C_6)$ alkanoyl, $(C_1-C_6)$-alkoxy, $(C_1-C_6)$-alkyl, halogen, $(C_1-C_6)$alkoxycarbonyl, nitro, halogeno$(C_1-C_6)$alkyl, halogeno($C_1$–$C_6$)alkoxy, amino, ($C_1$–$C_6$)alkylthio, hydroxyl, carboxyl, carbamoyl, mono- or di($C_1$–$C_6$) alkylaminocarbonyl, mono- or di($C_1$–$C_6$)acylamino, ($C_1$–$C_6$)alkylsulphinyl, ($C_1$–$C_6$)alkylsulphonyl, and/or cyano, or of ($C_1$–$C_6$)-alkoxy, ($C_1$–$C_6$)-alkoxycarbonyl, ($C_1$–$C_6$)-alkylthio, hydroxyl, carboxyl, partially fluorinated ($C_1$–$C_6$)-alkoxy with up to 6 fluorine atoms, ($C_1$–$C_6$)-alkyl, a 5- to 6-membered aromatic heterocycle which has up to 3 heteroatoms from the series S, N and/or O, is optionally bonded via a nitrogen atom and is optionally substituted by 1 to 3 substituents selected from ($C_1$–$C_6$)alkanoyl, ($C_1$–$C_6$)-alkoxy, ($C_1$–$C_6$)-alkyl, halogen, ($C_1$–$C_6$)alkoxycarbonyl, nitro, halogeno($C_1$–$C_6$)alkyl, halogeno($C_1$–$C_6$)alkoxy, amino, ($C_1$–$C_6$)alkylthio, hydroxyl, carboxyl, carbamoyl, mono- or di($C_1$–$C_6$)alkylaminocarbonyl, mono- or di($C_1$–$C_6$)acylamino, ($C_1$–$C_6$)alkylsulphinyl, ($C_1$–$C_6$)alkylsulphonyl, and/or cyano, or of a 3- to 8-membered saturated or unsaturated, nonaromatic, mono- or bicyclic heterocycle which has up to 3 heteroatoms from the series S, N and/or O, is optionally bonded via a nitrogen atom and is optionally substituted by 1 to 3 substituents selected from oxo, halogen, hydroxyl, ($C_1$–$C_6$)-alkoxycarbonyl, ($C_1$–$C_6$) alkoxycarbonylamino, ($C_1$–$C_6$)-alkyl, halogeno ($C_1$–$C_6$)-alkyl and hydroxy($C_1$–$C_6$)-alkyl, and groups of the formulae —$OR^{14}$, —$NR^{15}R^{16}$ or —CO—$NR^{17}R^{18}$, in which $R^{14}$ is phenyl, which in turn is optionally substituted by a group of the formula —$NR^{19}R^{20}$, in which $R^{19}$ and $R^{20}$ are identical or different and denote hydrogen, ($C_1$–$C_6$)-alkyl or ($C_1$–$C_6$)-acyl, or $R^{14}$ denotes ($C_1$–$C_6$)-alkyl which is optionally substituted once to three times by hydroxyl, $R^{15}$ and $R^{16}$ are identical or different and denote hydrogen, carbamoyl, mono- or di($C_1$–$C_6$) alkylaminocarbonyl, phenyl, ($C_1$–$C_6$)-acyl or ($C_1$–$C_6$)-alkyl, where ($C_1$–$C_6$)-alkyl is optionally substituted by ($C_1$–$C_6$)-alkoxy, ($C_1$–$C_6$)-acyl, by phenyl or by a 5- to 6-membered aromatic heterocycle with up to 3 heteroatoms from the series S, N and/or O, where aforementioned phenyl and aforementioned aromatic heterocycle are optionally substituted once to three times, identically or differently, by halogen and/or hydroxyl, and $R^{17}$ and $R^{18}$ are identical or different and denote hydrogen or ($C_1$–$C_6$)-alkyl, and the salts thereof.

3. A compound of the general formula (I) according to claim 1, in which $R^6$ represents phenyl which is optionally substituted by one to three substituents selected from the group consisting of halogen, ($C_6$–$C_{10}$)-aryl which is optionally substituted by 1 to 3 substituents selected from ($C_1$–$C_6$) alkanoyl, ($C_1$–$C_6$)-alkoxy, ($C_1$–$C_6$)-alkyl, halogen, ($C_1$–$C_6$)alkoxycarbonyl, nitro, halogeno($C_1$–$C_6$)alkyl, halogeno($C_1$–$C_6$)alkoxy, amino, ($C_1$–$C_6$)alkylthio, hydroxyl, carboxyl, carbamoyl, mono- or di($C_1$–$C_6$) alkylaminocarbonyl, mono- or di($C_1$–$C_6$)acylamino, ($C_1$–$C_6$)alkylsulphinyl, ($C_1$–$C_6$)alkylsulphonyl, and/or cyano, or ($C_1$–$C_6$)-alkoxy, ($C_1$–$C_6$)-alkoxycarbonyl, ($C_1$–$C_6$)-alkylthio, hydroxyl, carboxyl, partially fluorinated ($C_1$–$C_6$)-alkoxy with up to 6 fluorine atoms and ($C_1$–$C_6$)-alkyl, and the salts thereof.

4. A compound of the general formula (I) according to claim 1, in which $R^1$ represents hydrogen, halogen or represents ($C_1$–$C_6$)-alkyl, $R^2$ and $R^3$ are identical or different and represent hydrogen or ($C_3$–$C_8$)-cycloalkyl, or represent ($C_1$–$C_6$)-alkyl which is optionally substituted by 1 to 3 substituents selected from the group consisting of ($C_3$–$C_6$)-cycloalkyl, ($C_1$–$C_6$)-alkoxy, halogen, hydroxyl, radicals of the formula

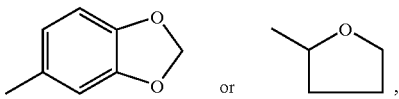

a 5- to 6-membered aromatic heterocycle with up to 3 heteroatoms from the series S, N and/or O, it also being possible for a nitrogen-containing heterocycle to be bonded via the nitrogen atom, and ($C_6$–$C_{10}$)-aryl which in turn can be substituted by hydroxyl or ($C_1$–$C_6$)-alkoxy, or $R^2$ and $R^3$ form, together with the nitrogen atom, a 5- to 6-membered saturated heterocycle which optionally also has an oxygen atom, $R^4$ represents hydrogen, ($C_1$–$C_6$)-acyl, ($C_2$–$C_6$)-alkenyl or $R^4$ represents ($C_1$–$C_6$)-alkyl which is optionally substituted by 1 to 3 substituents selected from the group consisting of halogen, hydroxyl, ($C_1$–$C_6$)-acyl, ($C_1$–$C_6$)-alkoxy, phenoxy, ($C_6$–$C_{10}$)-aryl and —$NR^7R^8$, in which $R^7$ and $R^8$ are identical or different and denote hydrogen, ($C_1$–$C_6$)-acyl, ($C_1$–$C_6$)-alkyl, carbamoyl, mono- or di($C_1$–$C_6$)-alkylaminocarbonyl or ($C_1$–$C_6$)-alkoxycarbonyl, or $R^7$ and $R^8$ form, together with the nitrogen atom, a 5- to 6-membered saturated heterocycle which optionally contains another heteroatom from the series S or O or a radical of the formula —$NR^9$, in which $R^9$ denotes hydrogen or ($C_1$–$C_4$)-alkyl, or $R^4$ represents ($C_1$–$C_6$)-alkyl which is substituted by a 5- to 6-membered aromatic, optionally benzo-fused heterocycle with up to 3 heteroatoms from the series S, N and/or O, it being possible for a nitrogen-containing heterocycle also to be bonded via the nitrogen atom, or is substituted by radicals of the formulae

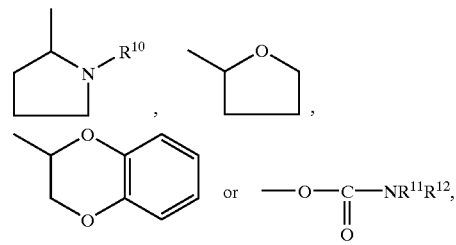

in which $R^{10}$ denotes hydrogen or ($C_1$–$C_6$)-alkyl, $R^{11}$ and $R^{12}$ are identical or different and denote hydrogen, ($C_1$–$C_6$)-alkyl or ($C_6$–$C_{10}$)-aryl, where aforementioned ($C_1$–$C_6$)-alkyl and ($C_6$–$C_{10}$)-aryl is optionally substituted by 1 to 3 substituents selected from the group consisting of hydroxyl, $(C_1-C_6)$-alkoxy and halogen, $R^5$ represents hydrogen or $(C_1-C_6)$-alkyl, $R^6$ represents a radical of the formula

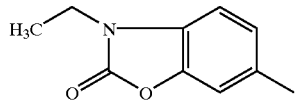

or $R^6$ represents phenyl which is optionally substituted by one to two substituents selected from the group consisting of halogen, $(C_6-C_{10})$-aryl, $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy with up to 6 fluorine atoms, radicals of the formulae

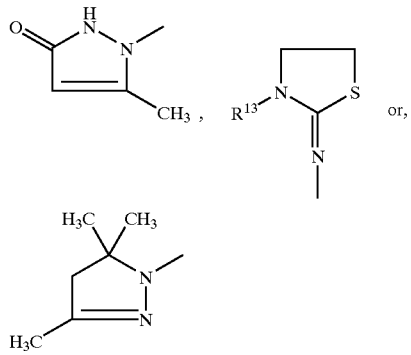

in which $R^{13}$ denotes hydrogen or $(C_1-C_6)$-alkyl, $(C_1-C_6)$-alkyl, which is optionally substituted by a radical of the formula

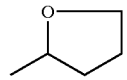

a 5- to 6-membered aromatic heterocycle which has up to 3 heteroatoms from the series S, N and/or O, is optionally bonded via a nitrogen atom and is optionally substituted by one to three halogen atoms, a 3- to 8-membered, saturated or unsaturated, nonaromatic heterocycle which has up to 3 heteroatoms from the series S, N and/or O, is optionally bonded via a nitrogen atom and is optionally substituted by 1 to 3 substituents selected from oxo, halogen, hydroxyl, $(C_1-C_6)$-alkoxycarbonyl, $(C_1-C_6)$-alkyl, halogeno$(C_1-C_6)$-alkyl and hydroxy$(C_1-C_6)$-alkyl, and groups of the formulae —$OR^{14}$, —$NR^{15}R^{16}$ or —CO—$NR^{17}R^{18}$, in which $R^{14}$ denotes a radical of the formula

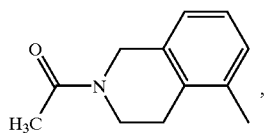

or phenyl which in turn is optionally substituted by a group of the formula —$NR^{19}R^{20}$, in which $R^{19}$ and $R^{20}$ are identical or different and denote hydrogen, $(C_1-C_6)$-alkyl or $(C_1-C_6)$-acyl, or $R^{14}$ denotes $(C_1-C_6)$-alkyl which is optionally substituted once to three times by hydroxyl, $R^{15}$ and $R^{16}$ are identical or different and denote hydrogen, carbamoyl, mono- or di$(C_1-C_6)$ alkylaminocarbonyl, phenyl, $(C_1-C_6)$-acyl or $(C_1-C_6)$-alkyl, where $(C_1-C_6)$-alkyl is optionally substituted by $(C_1-C_6)$-alkoxy, $(C_1-C_6)$-acyl, by phenyl or by a 5- to 6-membered aromatic heterocycle with up to 3 heteroatoms from the series S, N and/or O, where aforementioned phenyl and aforementioned aromatic heterocycle are optionally substituted once to three times, identically or differently, by halogen and/or hydroxyl, and $R^{17}$ and $R^{18}$ are identical or different and denote hydrogen or $(C_1-C_6)$-alkyl, and the salts thereof.

5. A compound of the general formula (I) according to claim 4, in which $R^1$ represents hydrogen, chlorine or represents $(C_1-C_3)$-alkyl, $R^2$ and $R^3$ are identical or different and represent hydrogen or cyclopropyl or cyclopentyl, or represent $(C_1-C_3)$-alkyl which is optionally substituted by 1 to 3 substituents selected from the group consisting of cyclopropyl, cyclopentyl, $(C_1-C_3)$-alkoxy, chlorine, fluorine, hydroxyl, radicals of the formula

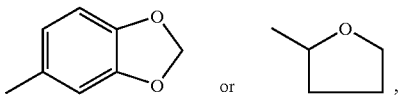

and pyridyl, furyl, thienyl, imidazolyl, N-triazolyl or pyrrolyl, phenyl which in turn may be substituted by hydroxyl or $(C_1-C_3)$-alkoxy, or $R^2$ and $R^3$ form, together with the nitrogen atom, a morpholine, piperidine or pyrrolidine ring, $R^4$ represents hydrogen, $(C_1-C_3)$-acyl, $(C_2-C_3)$-alkenyl, or $R^4$ represents $(C_1-C_6)$-alkyl which is optionally substituted by 1 to 3 substituents selected from the group consisting of chlorine, fluorine, hydroxyl, $(C_1-C_3)$-acyl, $(C_1-C_3)$-alkoxy, phenoxy, phenyl and —$NR^7R^8$, in which $R^7$ and $R^8$ are identical or different and denote hydrogen, $(C_1-C_4)$-acyl, $(C_1-C_4)$-alkyl, carbamoyl, mono- or di$(C_1-C_3)$-alkylaminocarbonyl or $(C_1-C_4)$-alkoxycarbonyl, or $R^7$ and $R^8$ form, together with the nitrogen atom, a morpholino, piperidinyl or pyrrolidinyl ring, or R⁴ represents $(C_1-C_6)$-alkyl which is substituted by a 5- to 6-membered aromatic, optionally benzo-fused heterocycle with up to 3 heteroatoms from the series S, N and/or O, it also being possible for a nitrogen-containing heterocycle to be bonded via the nitrogen atom, or is substituted by radicals of the formulae

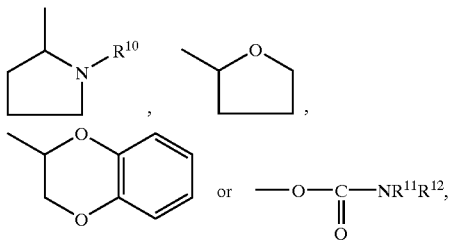

in which
R¹⁰ denotes hydrogen or $(C_1-C_4)$-alkyl,
R¹¹ and R¹² are identical or different and denote hydrogen, $(C_1-C_3)$-alkyl or phenyl, where aforementioned $(C_1-C_3)$-alkyl and phenyl is optionally substituted by 1 to 3 substituents selected from the group consisting of hydroxyl, $(C_1-C_3)$-alkoxy, chlorine and fluorine,
R⁵ represents hydrogen or $(C_1-C_3)$-alkyl,
R⁶ represents phenyl which is optionally substituted by one to two substituents selected from the group consisting of
chlorine, fluorine, phenyl, $(C_1-C_4)$-alkoxy, $(C_1-C_4)$-alkoxycarbonyl, $(C_1-C_3)$-alkylthio, hydroxyl, carboxyl, partially fluorinated $(C_1-C_4)$-alkoxy with up to 5 fluorine atoms,
radicals of the formulae

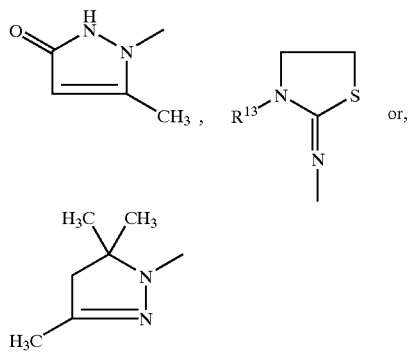

in which R¹³ denotes hydrogen or $(C_1-C_3)$-alkyl,
$(C_1-C_6)$-alkyl which is optionally substituted by a radical of the formula

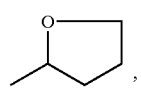

triazolyl,
morpholino, thiomorpholino, piperidinyl, pyrrolidinyl, azacycloheptanyl, azacyclobutanyl, each of which is optionally substituted by 1 to 2 substituents selected from oxo, chlorine, fluorine, hydroxyl, $(C_1-C_4)$-alkoxycarbonyl, $(C_1-C_3)$-alkyl, chloro- or fluoro $(C_1-C_3)$-alkyl and hydroxy$(C_1-C_4)$-alkyl,

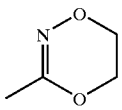

and groups of the formulae —OR⁴, —NR¹⁵R¹⁶ or —CO—NR¹⁷R¹⁸,
in which
R¹⁴ denotes a radical of the formula

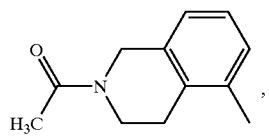

or phenyl which is in turn optionally substituted by a group of the formula —NR¹⁹R²⁰,
in which
R¹⁹ and R²⁰ are identical or different and denote hydrogen, $(C_1-C_3)$-alkyl or $(C_1-C_3)$-acyl,
or
R¹⁴ denotes $(C_1-C_4)$-alkyl which is optionally substituted once to three times by hydroxyl,
R¹⁵ and R¹⁶ are identical or different and denote hydrogen, carbamoyl, mono- or di$(C_1-C_3)$ alkylaminocarbonyl, phenyl, $(C_1-C_3)$-acyl or $(C_1-C_3)$-alkyl, where $(C_1-C_3)$-alkyl is optionally substituted by $(C_1-C_3)$-alkoxy, $(C_1-C_3)$-acyl, by phenyl or pyridyl,
where aforementioned phenyl and aforementioned pyridyl are optionally substituted once to twice, identically or differently, by chlorine, fluorine and/or hydroxyl, and
R¹⁷ and R¹⁸ are identical or different and denote hydrogen or $(C_1-C_4)$-alkyl,
and the salts thereof.

6. A compound of the general formula (I) according to claim 1, in which R⁵ is hydrogen.

7. A compound of the general formula (I) according to claim 1, in which R² and R³ are hydrogen or $(C_1-C_3)$alkyl.

8. A compound of the general formula (I) according to claim 1, in which R⁶ is a para-substituted phenyl group.

9. A compound according to claim 1, which has the following formula:

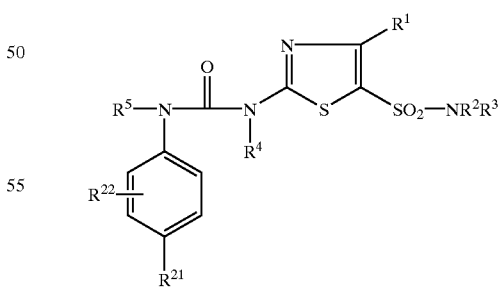

in which
R¹ to R⁵ are as defined above, and R²¹ represents halogen, $(C_6-C_{10})$-aryl which is optionally substituted by 1 to 3 substituents selected from $(C_1-C_6)$ alkanoyl, $(C_1-C_6)$-alkoxy, $(C_1-C_6)$-alkyl, halogen, $(C_1-C_6)$alkoxycarbonyl, nitro, halogeno$(C_1-C_6)$ alkyl, halogeno$(C_1-C_6)$alkoxy, amino, $(C_1-C_6)$ alkylthio, hydroxyl, carboxyl, carbamoyl, mono- or di($C_1$–$C_6$)alkylaminocarbonyl, mono- or di($C_1$–$C_6$)acylamino, ($C_1$–$C_6$)alkylsulphinyl, ($C_1$–$C_6$)alkylsulphonyl, and/or cyano, or ($C_1$–$C_6$)-alkoxy, ($C_1$–$C_6$)-alkoxycarbonyl, ($C_1$–$C_6$)-alkylthio, hydroxyl, carboxyl, partially fluorinated ($C_1$–$C_6$)-alkoxy with up to 6 fluorine atoms, radicals of the formulae

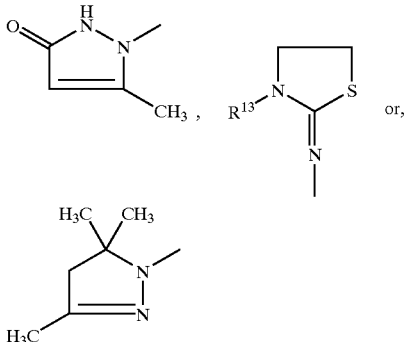

in which $R^{13}$ denotes hydrogen or ($C_1$–$C_6$)-alkyl, ($C_1$–$C_6$)-alkyl which is optionally substituted by a radical of the formula

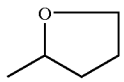

a 5- to 6-membered aromatic heterocycle which has up to 3 heteroatoms from the series S, N and/or O, is optionally bonded via a nitrogen atom and is optionally substituted by 1 to 3 substituents selected from ($C_1$–$C_6$)alkanoyl, ($C_1$–$C_6$)-alkoxy, ($C_1$–$C_6$)-alkyl, halogen, ($C_1$–$C_6$)alkoxycarbonyl, nitro, halogeno($C_1$–$C_6$)alkyl, halogeno($C_1$–$C_6$)alkoxy, amino, ($C_1$–$C_6$)alkylthio, hydroxyl, carboxyl, carbamoyl, mono- or di($C_1$–$C_6$)alkylaminocarbonyl, mono- or di($C_1$–$C_6$)acylamino, ($C_1$–$C_6$)alkylsulphinyl, ($C_1$–$C_6$)alkylsulphonyl, and/or cyano, a 3- to 8-membered saturated or unsaturated, nonaromatic mono- or bicyclic heterocycle which has up to 3 heteroatoms from the series S, N and/or O, is optionally bonded via a nitrogen atom and is optionally substituted by 1 to 3 substituents selected from oxo, halogen, hydroxyl, ($C_1$–$C_6$)-alkoxycarbonyl, ($C_1$–$C_6$)-alkoxycarbonylamino, ($C_1$–$C_6$)-alkyl, halogeno($C_1$–$C_6$)-alkyl and hydroxy($C_1$–$C_6$)-alkyl, and groups of the formulae —$OR^{14}$, —$NR^{15}R^{16}$ or —CO—$NR^{17}R^{18}$, in which $R^{14}$ denotes a radical of the formula

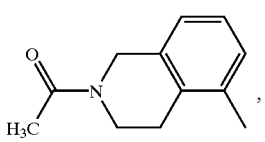

or denotes phenyl which in turn is optionally substituted by a group of the formula —$NR^{19}R^{20}$, in which $R^{19}$ and $R^{20}$ are identical or different and denote hydrogen, ($C_1$–$C_6$)-alkyl or ($C_1$–$C_6$)-acyl, or $R^{14}$ denotes ($C_1$–$C_6$)-alkyl which is optionally substituted once to three times by hydroxyl, $R^{15}$ and $R^{16}$ are identical or different and denote hydrogen, carbamoyl, mono- or di($C_1$–$C_6$)alkylaminocarbonyl, phenyl, ($C_1$–$C_6$)-acyl or ($C_1$–$C_6$)-alkyl, where ($C_1$–$C_6$)-alkyl is optionally substituted by ($C_1$–$C_6$)-alkoxy, ($C_1$–$C_6$)-acyl, by phenyl or by a 5- to 6-membered aromatic heterocycle with up to 3 heteroatoms from the series S, N and/or O, where aforementioned phenyl and aforementioned aromatic heterocycle are optionally substituted once to three times, identically or differently, by halogen and/or hydroxyl, and $R^{17}$ and $R^{18}$ are identical or different and denote hydrogen or ($C_1$–$C_6$)-alkyl, and salts thereof $R^{22}$ may have the above meaning of $R^{21}$ and may be identical to or different from the latter, or $R^{22}$ is hydrogen, and their salts.

10. A compound according to claim 4, which has the following formula:

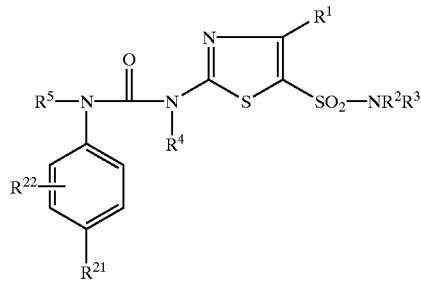

in which $R^1$ to $R^5$ are as defined above, and $R^{21}$ represents halogen, ($C_6$–$C_{10}$)-aryl, ($C_1$–$C_6$)-alkoxy, ($C_1$–$C_6$)-alkoxycarbonyl, ($C_1$–$C_6$)-alkylthio, hydroxyl, carboxyl, partially fluorinated ($C_1$–$C_6$)-alkoxy with up to 6 fluorine atoms, radicals of the formulae

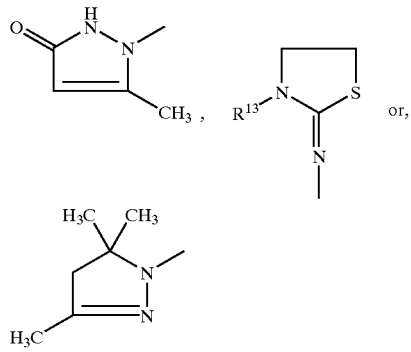

in which $R^{13}$ denotes hydrogen or ($C_1$–$C_6$)-alkyl, ($C_1$–$C_6$)-alkyl which is optionally substituted by a radical of the formula

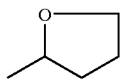

a 5- to 6-membered aromatic heterocycle which has up to 3 heteroatoms from the series S, N and/or O, is optionally bonded via a nitrogen atom and is optionally substituted by one to three halogen atoms, a 3- to 8-membered saturated or unsaturated, nonaromatic heterocycle which has up to 3 heteroatoms from the series S, N and/or O, is optionally bonded via a nitrogen atom and is optionally substituted by 1 to 3 substituents selected from oxo, halogen, hydroxyl, $(C_1-C_6)$-alkoxycarbonyl, $(C_1-C_6)$-alkyl, halogeno$(C_1-C_6)$-alkyl and hydroxy$(C_1-C_6)$-alkyl, or represents groups of the formulae —$OR^{14}$, —$NR^{15}R^{16}$ or —CO—$NR^{17}R^{18}$, in which $R^{14}$ denotes a radical of the formula

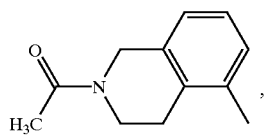

or denotes phenyl which in turn is optionally substituted by a group of the formula —$NR^{19}R^{20}$, in which $R^{19}$ and $R^{20}$ are identical or different and denote hydrogen, $(C_1-C_6)$-alkyl or $(C_1-C_6)$-acyl, or $R^{14}$ denotes $(C_1-C_6)$-alkyl which is optionally substituted once to three times by hydroxyl, $R^{15}$ and $R^{16}$ are identical or different and denote hydrogen, carbamoyl, mono- or di$(C_1-C_6)$ alkylaminocarbonyl, phenyl, $(C_1-C_6)$-acyl or $(C_1-C_6)$-alkyl, where $(C_1-C_6)$-alkyl is optionally substituted by $(C_1-C_6)$-alkoxy, $(C_1-C_6)$-acyl, by phenyl or by a 5- to 6-membered aromatic heterocycle with up to 3 heteroatoms from the series S, N and/or O, where aforementioned phenyl and aforementioned aromatic heterocycle are optionally substituted once to three times, identically or differently, by halogen and/or hydroxyl, and $R^{17}$ and $R^{18}$ are identical or different and denote hydrogen or $(C_1-C_6)$-alkyl, and $R^{22}$ may have the above meaning of $R^{21}$ and may be identical to or different from the latter, or $R^{22}$ is hydrogen.

11. A compound according to claim 9, in which $R^{22}$ is hydrogen.

12. A compound according to claim 10, in which $R^{21}$ represents phenyl, $(C_1-C_4)$-alkoxy or a 3- to 8-membered saturated or unsaturated, nonaromatic heterocycle which has up to 3 heteroatoms from the series S, N and/or O, is optionally bound via a nitrogen atom and may optionally be substituted by 1 to 3 substituents selected from oxo, halogen, hydroxyl, $(C_1-C_6)$-alkoxycarbonyl, $(C_1-C_6)$-alkyl, halogeno$(C_1-C_6)$alkyl and hydroxy$(C_1-C_6)$-alkyl.

13. A compound of the general formula (II)

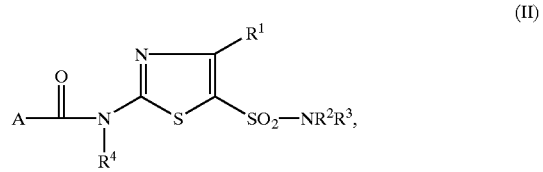

(II)

in which $R^1$ represents hydrogen, halogen, $(C_1-C_6)$-alkyl, $(C_1-C_6)$-alkoxy, amino$(C_1-C_6)$alkyl or halogeno$(C_1-C_6)$alkyl, $R^2$ and $R^3$ are identical or different and represent hydrogen, $(C_3-C_8)$-cycloalkyl or biphenylylaminocarbonyl, or represent $(C_1-C_6)$-alkyl which is optionally substituted by 1 to 3 substituents selected from the group consisting of $(C_3-C_6)$-cycloalkyl, $(C_1-C_6)$-alkoxy, halogen, hydroxyl, radicals of the formula

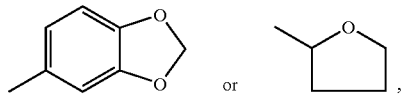

a 5- to 6-membered aromatic heterocycle with up to 3 heteroatoms from the series S, N and/or O, it also being possible for a nitrogen-containing heterocycle to be bonded via the nitrogen atom, a 3- to 8-membered saturated or unsaturated, nonaromatic heterocycle which has up to 3 heteroatoms from the series S, N and/or O and is optionally bonded via a nitrogen atom, and $(C_6-C_{10})$-aryl which in turn may be substituted by hydroxyl or $(C_1-C_6)$-alkoxy, or $R^2$ and $R^3$ form, together with the nitrogen atom, a 5- to 6-membered saturated heterocycle which optionally also has an oxygen atom, $R^4$ represents hydrogen, $(C_1-C_6)$-acyl, $(C_2-C_6)$-alkenyl, or $R^4$ represents $(C_1-C_6)$-alkyl which is optionally substituted by 1 to 3 substituents selected from the group consisting of halogen, hydroxyl, $(C_1-C_6)$-acyl, $(C_1-C_6)$-alkoxy, phenoxy, $(C_6-C_{10})$-aryl and —$NR^7R^8$, in which $R^7$ and $R^8$ are identical or different and denote hydrogen, $(C_1-C_6)$-acyl, $(C_1-C_6)$-alkyl, carbamoyl, mono- or di$(C_1-C_6)$-alkylamino$(C_1-C_6)$alkyl, mono- or di$(C_1-C_6)$-alkylaminocarbonyl, $(C_6-C_{10})$-aryl or $(C_1-C_6)$-alkoxycarbonyl, or $R^7$ and $R^8$ form, together with the nitrogen atom, a 5- to 6-membered saturated heterocycle which optionally contains another heteroatom from the series S or O or a radical of the formula —$NR^9$ and may be substituted by oxo, in which $R^9$ denotes hydrogen or $(C_1-C_4)$-alkyl, or $R^4$ represents $(C_1-C_6)$-alkyl which is substituted by a 5- to 6-membered aromatic, optionally benzo-fused heterocycle with up to 3 heteroatoms from the series S, N and/or O, it also being possible for a nitrogen-containing heterocycle to be bonded via the nitrogen atom, or is substituted by radicals of the formulae

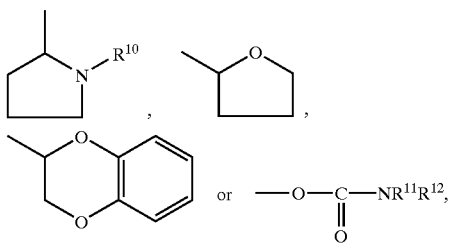

or , in which
R[10] denotes hydrogen or $(C_1-C_6)$-alkyl,
R[11] and R[12] are identical or different and denote hydrogen, $(C_1-C_6)$-alkyl or $(C_6-C_{10})$-aryl, said $(C_1-C_6)$-alkyl and $(C_6-C_{10})$-aryl optionally substituted by 1 to 3 substituents selected from the group consisting of hydroxyl, $(C_1-C_6)$-alkoxy and halogen,
and A represents a halogen atom.

14. A process for preparing the compounds of the general formula (I) according to claim 1, characterized in that
   [A] compounds of the general formula (II)

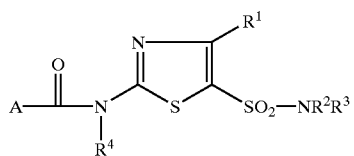     (II)

in which
R[1], R[2], R[3] and R[4] have the meaning indicated in claim 1, and
A represents halogen,
are reacted with amines of the general formula (III)

HNR[5]R[6]     (III)

in which

R[5] and R[6] have the meaning indicated in claim 1,
in inert solvents, where appropriate in the presence of a base and/or aid, or
   [B] isocyanates of the general formula (IV)

R[6]—NCO     (IV)

in which
R[6] has the meaning indicated in claim 1,
are reacted with thiazolylamines of the general formula (V)

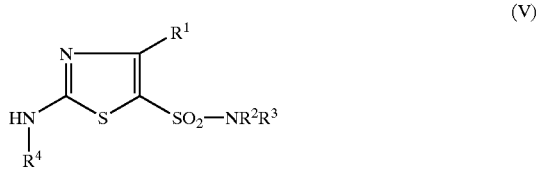     (V)

in which
R[1], R[2], R[3] and R[4] have the meaning indicated in claim 1,
in inert solvents and, in the case where R[5] is different from hydrogen, an alkylation is carried out by conventional processes.

15. A pharmaceutical composition which comprises a compound of the general formula (I) according to claim 1 mixed with a pharmaceutically acceptable carrier or excipient.

16. A method of treating a viral infection, comprising administering to a mammal an effective amount of a compound of the general formula (I) according to claim 1.

17. The method of claim 16, wherein said viral infection is herpes virus infection.

18. The method of claim 17, wherein said herpes virus infection is herpes simplex virus infection.

* * * * *